(12) United States Patent
Oleson et al.

(10) Patent No.: US 9,759,738 B2
(45) Date of Patent: Sep. 12, 2017

(54) SPORTS ELECTRONIC TRAINING SYSTEM, AND APPLICATIONS THEREOF

(71) Applicant: adidas International Marketing B.V., Amsterdam (NL)

(72) Inventors: Mark Arthur Oleson, Portland, OR (US); Christian Dibenedetto, North Plains, OR (US); Scott Tomlinson, Portland, OR (US); Allen W. Van Noy, Portland, OR (US); Amy Jones Vaterlaus, Portland, OR (US); Stephen Michael Vincent, Portland, OR (US)

(73) Assignee: adidas International Marketing B.V., Amsterdam (NL)

( * ) Notice: Subject to any disclaimer, the term of this patent is extended or adjusted under 35 U.S.C. 154(b) by 17 days.

(21) Appl. No.: 15/145,522

(22) Filed: May 3, 2016

(65) Prior Publication Data

US 2016/0245840 A1    Aug. 25, 2016

Related U.S. Application Data

(63) Continuation of application No. 14/734,808, filed on Jun. 9, 2015, now Pat. No. 9,645,165, which is a (Continued)

(51) Int. Cl.
*G01P 15/00*      (2006.01)
*A43B 13/00*      (2006.01)
(Continued)

(52) U.S. Cl.
CPC ............ *G01P 15/00* (2013.01); *A43B 3/0005* (2013.01); *A43B 5/00* (2013.01); *A43B 5/06* (2013.01);
(Continued)

(58) Field of Classification Search
CPC .... A43B 3/0005; A61B 5/103; G01C 22/006; G06F 17/40
See application file for complete search history.

(56) References Cited

U.S. PATENT DOCUMENTS 2,801,629 A    8/1957   Edmark, Jr.
3,473,526 A    10/1969  Herman et al.
(Continued)

FOREIGN PATENT DOCUMENTS

CN    1588275    3/2005
CN    1601447    3/2005
(Continued)

OTHER PUBLICATIONS

AboutGolf Driving Technology, at http://www.aboutgolf.com, 10 pages, posted Feb. 24, 2005.
(Continued)

*Primary Examiner* — Daniel S Larkin
(74) *Attorney, Agent, or Firm* — Stern, Kessler, Goldstein & Fox P.L.L.C.

(57) ABSTRACT

A sports electronic training system, and applications thereof, are disclosed. In an embodiment, the system comprises at least one monitor and an electronic processing device for receiving data from the at least one monitor and providing feedback to an individual based on the received data. The monitor can be a motion monitor that measures an individual's performance such as, for example, speed, pace and distance for a runner.

20 Claims, 63 Drawing Sheets

Related U.S. Application Data continuation of application No. 13/740,966, filed on Jan. 14, 2013, now Pat. No. 9,087,159, which is a continuation of application No. 11/889,978, filed on Aug. 17, 2007, now Pat. No. 8,360,904.

(51) Int. Cl.

| | |
|---|---|
| G09B 19/00 | (2006.01) |
| H04B 1/3827 | (2015.01) |
| A63B 24/00 | (2006.01) |
| A63B 43/00 | (2006.01) |
| G06F 17/40 | (2006.01) |
| A43B 3/00 | (2006.01) |
| A43B 5/00 | (2006.01) |
| G06F 1/16 | (2006.01) |
| A43B 5/06 | (2006.01) |
| A61B 5/11 | (2006.01) |
| G01S 19/19 | (2010.01) |
| G06F 19/00 | (2011.01) |
| A63B 71/06 | (2006.01) |
| A63B 102/32 | (2015.01) |
| A63B 102/02 | (2015.01) |
| A63B 102/18 | (2015.01) |
| A63B 22/00 | (2006.01) |
| A63B 22/02 | (2006.01) |
| A63B 22/06 | (2006.01) |
| H04M 1/725 | (2006.01) |

(52) U.S. Cl.
CPC ............ *A43B 13/00* (2013.01); *A61B 5/1118* (2013.01); *A63B 24/0006* (2013.01); *A63B 24/0062* (2013.01); *A63B 24/0075* (2013.01); *A63B 24/0084* (2013.01); *A63B 24/0087* (2013.01); *A63B 43/00* (2013.01); *A63B 43/004* (2013.01); *A63B 71/0622* (2013.01); *G01S 19/19* (2013.01); *G06F 1/163* (2013.01); *G06F 17/40* (2013.01); *G06F 19/3481* (2013.01); *G09B 19/0038* (2013.01); *H04B 1/3827* (2013.01); *A63B 22/0056* (2013.01); *A63B 22/0076* (2013.01); *A63B 22/02* (2013.01); *A63B 22/0605* (2013.01); *A63B 22/0664* (2013.01); *A63B 2024/0093* (2013.01); *A63B 2024/0096* (2013.01); *A63B 2071/065* (2013.01); *A63B 2071/0625* (2013.01); *A63B 2071/0638* (2013.01); *A63B 2102/02* (2015.10); *A63B 2102/18* (2015.10); *A63B 2102/32* (2015.10); *A63B 2220/12* (2013.01); *A63B 2220/14* (2013.01); *A63B 2220/20* (2013.01); *A63B 2220/22* (2013.01); *A63B 2220/30* (2013.01); *A63B 2220/40* (2013.01); *A63B 2220/70* (2013.01); *A63B 2220/72* (2013.01); *A63B 2220/73* (2013.01); *A63B 2220/803* (2013.01); *A63B 2220/833* (2013.01); *A63B 2220/836* (2013.01); *A63B 2225/20* (2013.01); *A63B 2225/50* (2013.01); *A63B 2230/06* (2013.01); *A63B 2230/207* (2013.01); *A63B 2230/50* (2013.01); *A63B 2243/0025* (2013.01); *A63B 2243/0037* (2013.01); *A63F 2300/69* (2013.01); *H04M 1/72522* (2013.01)

(56) References Cited

U.S. PATENT DOCUMENTS

| | | |
|---|---|---|
| 3,631,994 A | 1/1972 | Mackzum, Jr. |
| 3,742,937 A | 7/1973 | Manuel et al. |
| 3,802,698 A | 4/1974 | Burian et al. |
| 3,838,684 A | 10/1974 | Manuel et al. |
| 3,859,496 A | 1/1975 | Giese |
| 3,935,669 A | 2/1976 | Potrzuski et al. |
| 3,978,849 A | 9/1976 | Geneen |
| 4,027,663 A | 6/1977 | Fischler et al. |
| 4,038,976 A | 8/1977 | Hardy et al. |
| 4,083,481 A | 4/1978 | Selinko |
| 4,120,294 A | 10/1978 | Wolfe |
| 4,120,296 A | 10/1978 | Prinz |
| 4,173,016 A | 10/1979 | Dickson |
| 4,221,223 A | 9/1980 | Linden |
| 4,248,244 A | 2/1981 | Charnitski et al. |
| 4,252,128 A | 2/1981 | Kane |
| 4,299,344 A | 11/1981 | Yamashita et al. |
| 4,371,945 A | 2/1983 | Karr et al. |
| 4,436,096 A | 3/1984 | Dyck et al. |
| 4,534,557 A | 8/1985 | Bigelow et al. |
| 4,577,865 A | 3/1986 | Shishido |
| 4,578,769 A | 3/1986 | Frederick |
| 4,647,217 A | 3/1987 | Havel |
| 4,651,446 A | 3/1987 | Yukawa et al. |
| 4,653,498 A | 3/1987 | New et al. |
| 4,674,743 A | 6/1987 | Hirano |
| 4,703,445 A | 10/1987 | Dassler |
| 4,761,648 A | 8/1988 | Ellis |
| 4,771,394 A | 9/1988 | Cavanagh |
| 4,775,948 A | 10/1988 | Dial et al. |
| 4,788,983 A | 12/1988 | Brink et al. |
| 4,828,257 A | 5/1989 | Dyer et al. |
| 4,830,021 A | 5/1989 | Thornton |
| 4,867,442 A | 9/1989 | Matthews |
| 4,911,005 A | 3/1990 | Heyn et al. |
| 4,938,228 A | 7/1990 | Righter et al. |
| 5,043,736 A | 8/1991 | Darnell et al. |
| 5,063,690 A | 11/1991 | Slenker |
| 5,086,394 A | 2/1992 | Shapira |
| 5,117,444 A | 5/1992 | Sutton et al. |
| 5,137,501 A | 8/1992 | Mertesdorf |
| 5,148,002 A | 9/1992 | Kuo et al. |
| 5,209,483 A | 5/1993 | Gedney et al. |
| 5,215,468 A | 6/1993 | Lauffer et al. |
| 5,241,542 A | 8/1993 | Natarajan et al. |
| 5,283,733 A | 2/1994 | Colley |
| 5,301,678 A | 4/1994 | Watson et al. |
| 5,302,807 A | 4/1994 | Zhao |
| 5,314,389 A | 5/1994 | Dotan |
| 5,334,974 A | 8/1994 | Simms et al. |
| 5,335,188 A | 8/1994 | Brisson |
| 5,430,435 A | 7/1995 | Hoch et al. |
| 5,454,376 A | 10/1995 | Stephens et al. |
| 5,463,537 A | 10/1995 | Trattner et al. |
| 5,465,197 A | 11/1995 | Chien |
| 5,470,233 A | 11/1995 | Fruchterman et al. |
| 5,471,405 A | 11/1995 | Marsh |
| 5,485,402 A | 1/1996 | Smith et al. |
| 5,487,181 A | 1/1996 | Dailey et al. |
| 5,492,514 A | 2/1996 | Daum |
| 5,509,421 A | 4/1996 | Muller et al. |
| 5,524,637 A | 6/1996 | Erickson |
| 5,526,326 A | 6/1996 | Fekete et al. |
| 5,531,601 A | 7/1996 | Amoroso |
| 5,534,917 A | 7/1996 | MacDougall |
| 5,564,698 A | 10/1996 | Honey et al. |
| 5,566,942 A | 10/1996 | Elum |
| 5,568,928 A | 10/1996 | Munson et al. |
| 5,583,776 A | 12/1996 | Levi et al. |
| 5,586,557 A | 12/1996 | Nelson et al. |
| 5,592,401 A | 1/1997 | Kramer |
| 5,598,849 A | 2/1997 | Browne |
| 5,616,078 A | 4/1997 | Oh |
| 5,664,292 A | 9/1997 | Chen |
| 5,720,200 A | 2/1998 | Anderson et al. |
| 5,721,539 A | 2/1998 | Goetzl |
| 5,724,265 A | 3/1998 | Hutchings |
| 5,735,799 A | 4/1998 | Baba et al. |
| 5,742,509 A | 4/1998 | Goldberg et al. |
| 5,745,347 A | 4/1998 | Miller et al. |
| 5,748,103 A | 5/1998 | Flach et al. |

(56) References Cited

U.S. PATENT DOCUMENTS

| | | |
|---|---|---|
| 5,749,365 A | 5/1998 | Magill |
| 5,751,245 A | 5/1998 | Janky et al. |
| 5,757,929 A | 5/1998 | Wang et al. |
| 5,761,096 A | 6/1998 | Zakutin |
| 5,767,795 A | 6/1998 | Schaphorst |
| 5,769,755 A | 6/1998 | Henry et al. |
| 5,775,011 A | 7/1998 | Reitano, Jr. |
| 5,779,576 A | 7/1998 | Smith, III et al. |
| 5,802,492 A | 9/1998 | DeLorme et al. |
| 5,810,685 A | 9/1998 | Willner et al. |
| 5,825,283 A | 10/1998 | Camhi |
| 5,825,327 A | 10/1998 | Krasner |
| 5,835,077 A | 11/1998 | Dao et al. |
| 5,857,066 A | 1/1999 | Wyche et al. |
| 5,857,939 A | 1/1999 | Kaufman |
| 5,883,595 A | 3/1999 | Colley |
| 5,891,042 A | 4/1999 | Sham et al. |
| 5,899,963 A | 5/1999 | Hutchings |
| 5,905,471 A | 5/1999 | Biebl et al. |
| 5,908,464 A | 6/1999 | Kishigami et al. |
| 5,912,864 A | 6/1999 | Maurer |
| 5,913,827 A | 6/1999 | Gorman |
| 5,919,239 A | 7/1999 | Fraker et al. |
| 5,920,287 A | 7/1999 | Belcher et al. |
| 5,925,001 A | 7/1999 | Hoyt et al. |
| 5,928,306 A | 7/1999 | France et al. |
| 5,938,721 A | 8/1999 | Dussell et al. |
| 5,946,643 A | 8/1999 | Zakutin |
| 5,947,824 A | 9/1999 | Minami et al. |
| 5,947,868 A | 9/1999 | Dugan |
| 5,948,040 A | 9/1999 | DeLorme et al. |
| 5,955,667 A | 9/1999 | Fyfe |
| 5,976,083 A | 11/1999 | Richardson et al. |
| 5,986,200 A | 11/1999 | Curtin |
| 5,989,157 A | 11/1999 | Walton |
| 6,002,982 A | 12/1999 | Fry |
| 6,009,138 A | 12/1999 | Slusky |
| 6,011,491 A | 1/2000 | Goetzl |
| 6,013,007 A | 1/2000 | Root et al. |
| 6,018,705 A | 1/2000 | Gaudet et al. |
| 6,027,428 A | 2/2000 | Thomas et al. |
| 6,032,108 A | 2/2000 | Seiple et al. |
| 6,046,689 A | 4/2000 | Newman |
| 6,047,203 A | 4/2000 | Sackner et al. |
| 6,052,654 A | 4/2000 | Gaudet et al. |
| 6,053,844 A | 4/2000 | Clem |
| 6,059,576 A | 5/2000 | Brann |
| 6,073,086 A | 6/2000 | Marinelli |
| 6,080,110 A | 6/2000 | Thorgersen |
| 6,080,111 A | 6/2000 | Pao-Lang |
| 6,088,000 A | 7/2000 | Ho |
| 6,097,345 A | 8/2000 | Walton |
| 6,104,947 A | 8/2000 | Heikkila et al. |
| 6,122,340 A | 9/2000 | Darley et al. |
| 6,122,960 A | 9/2000 | Hutchings et al. |
| 6,133,722 A | 10/2000 | Havel |
| 6,135,951 A | 10/2000 | Richardson et al. |
| 6,145,389 A | 11/2000 | Ebeling et al. |
| 6,145,551 A | 11/2000 | Jayaraman et al. |
| 6,148,262 A | 11/2000 | Fry |
| 6,148,271 A | 11/2000 | Marinelli |
| 6,151,563 A | 11/2000 | Marinelli |
| 6,157,898 A | 12/2000 | Marinelli |
| 6,159,131 A | 12/2000 | Pfeffer |
| 6,163,538 A | 12/2000 | Brown et al. |
| 6,163,718 A | 12/2000 | Fabrizio |
| 6,183,365 B1 | 2/2001 | Tonomura et al. |
| 6,192,230 B1 | 2/2001 | van Bokhorst et al. |
| 6,198,431 B1 | 3/2001 | Gibson |
| 6,204,807 B1 | 3/2001 | Odagiri et al. |
| 6,212,469 B1 | 4/2001 | Knepper et al. |
| 6,213,872 B1 | 4/2001 | Harada et al. |
| 6,230,047 B1 | 5/2001 | McHugh |
| 6,236,674 B1 | 5/2001 | Morelli et al. |
| 6,238,338 B1 | 5/2001 | DeLuca et al. |
| 6,246,362 B1 | 6/2001 | Tsubata et al. |
| 6,246,882 B1 | 6/2001 | Lachance |
| 6,251,048 B1 | 6/2001 | Kaufman |
| 6,266,623 B1 | 7/2001 | Vock et al. |
| 6,298,314 B1 | 10/2001 | Blackadar et al. |
| 6,301,964 B1 | 10/2001 | Fyfe et al. |
| 6,305,221 B1 | 10/2001 | Hutchings |
| 6,336,365 B1 | 1/2002 | Blackadar et al. |
| 6,345,197 B1 | 2/2002 | Fabrizio |
| 6,356,856 B1 | 3/2002 | Damen et al. |
| 6,357,147 B1 | 3/2002 | Darley et al. |
| 6,381,482 B1 | 4/2002 | Jayaraman et al. |
| 6,394,960 B1 | 5/2002 | Shinogi et al. |
| 6,397,151 B1 | 5/2002 | Yamagishi et al. |
| 6,397,153 B1 | 5/2002 | Yamagishi et al. |
| 6,410,835 B2 | 6/2002 | Suzuki et al. |
| 6,420,008 B1 | 7/2002 | Lewis et al. |
| 6,442,479 B1 | 8/2002 | Barton |
| 6,446,080 B1 | 9/2002 | Ryzin et al. |
| 6,463,385 B1 | 10/2002 | Fry |
| 6,471,586 B1 | 10/2002 | Aiki et al. |
| 6,477,542 B1 | 11/2002 | Papaioannou |
| 6,493,652 B1 | 12/2002 | Ohlenbusch et al. |
| 6,499,000 B2 | 12/2002 | Flentov et al. |
| 6,513,381 B2 | 2/2003 | Fyfe et al. |
| 6,513,532 B2 | 2/2003 | Mault et al. |
| 6,522,312 B2 | 2/2003 | Ohshima et al. |
| 6,532,432 B1 | 3/2003 | Nagatsuma et al. |
| 6,536,139 B2 | 3/2003 | Darley et al. |
| 6,539,336 B1 | 3/2003 | Burke et al. |
| 6,545,661 B1 | 4/2003 | Goschy et al. |
| 6,554,706 B2 | 4/2003 | Kim et al. |
| 6,565,449 B2 | 5/2003 | Buhler |
| 6,572,636 B1 | 6/2003 | Hagen et al. |
| 6,574,603 B1 | 6/2003 | Dickson et al. |
| 6,579,209 B1 | 6/2003 | Valette et al. |
| 6,582,330 B1 | 6/2003 | Rehkemper et al. |
| 6,582,342 B2 | 6/2003 | Kaufman |
| 6,585,622 B1 | 7/2003 | Shum et al. |
| 6,590,536 B1 | 7/2003 | Walton |
| 6,601,016 B1 | 7/2003 | Brown et al. |
| 6,605,038 B1 | 8/2003 | Teller et al. |
| 6,606,506 B1 | 8/2003 | Jones |
| 6,607,493 B2 | 8/2003 | Song |
| 6,611,789 B1 | 8/2003 | Darley |
| 6,623,427 B2 | 9/2003 | Mandigo |
| 6,626,799 B2 | 9/2003 | Watterson et al. |
| 6,628,265 B2 | 9/2003 | Hwang |
| 6,642,917 B1 | 11/2003 | Koyama et al. |
| 6,669,563 B1 | 12/2003 | Kitami et al. |
| 6,672,991 B2 | 1/2004 | O'Malley |
| 6,677,917 B2 | 1/2004 | Van Heerden et al. |
| 6,687,523 B1 | 2/2004 | Jayaramen et al. |
| 6,695,694 B2 | 2/2004 | Ishikawa et al. |
| 6,705,972 B1 | 3/2004 | Takeno et al. |
| 6,710,713 B1 | 3/2004 | Russo |
| 6,712,692 B2 | 3/2004 | Basson et al. |
| 6,716,139 B1 | 4/2004 | Hosseinzadeh-Dolkhani et al. |
| 6,727,197 B1 | 4/2004 | Wilson et al. |
| 6,729,025 B2 | 5/2004 | Farrell et al. |
| 6,734,837 B1 | 5/2004 | Havel |
| 6,736,759 B1 | 5/2004 | Stubbs et al. |
| 6,745,011 B1 | 6/2004 | Hendrickson et al. |
| 6,745,069 B2 | 6/2004 | Nissila et al. |
| 6,753,882 B2 | 6/2004 | Nakazawa et al. |
| 6,758,816 B1 | 7/2004 | Tsubata et al. |
| 6,767,282 B2 | 7/2004 | Matsuyama et al. |
| 6,790,178 B1 | 9/2004 | Mault et al. |
| 6,798,378 B1 | 9/2004 | Walters |
| 6,807,869 B2 | 10/2004 | Farringdon et al. |
| 6,808,473 B2 | 10/2004 | Hisano et al. |
| 6,823,036 B1 | 11/2004 | Chen |
| 6,832,109 B2 | 12/2004 | Nissila |
| 6,837,827 B1 | 1/2005 | Lee et al. |
| 6,847,892 B2 | 1/2005 | Zhou et al. |
| 6,853,955 B1 | 2/2005 | Burrell et al. |
| 6,872,077 B2 | 3/2005 | Yeager |
| 6,876,947 B1 | 4/2005 | Darley et al. |
| 6,880,750 B2 | 4/2005 | Pentel |

(56) References Cited

U.S. PATENT DOCUMENTS

| | | |
|---|---|---|
| 6,882,955 B1 | 4/2005 | Ohlenbusch et al. |
| 6,885,971 B2 | 4/2005 | Vock et al. |
| 6,898,550 B1 | 5/2005 | Blackadar et al. |
| 6,909,455 B1 | 6/2005 | Edwards et al. |
| 6,918,858 B2 | 7/2005 | Watterson et al. |
| 6,918,860 B1 | 7/2005 | Nusbaum |
| 6,925,851 B2 | 8/2005 | Reinbold et al. |
| 6,941,775 B2 | 9/2005 | Sharma |
| 6,959,259 B2 | 10/2005 | Vock et al. |
| 6,963,818 B2 | 11/2005 | Flentov et al. |
| 6,970,731 B1 | 11/2005 | Jayaraman et al. |
| 7,003,122 B2 | 2/2006 | Chen |
| 7,005,970 B2 | 2/2006 | Hodsdon et al. |
| 7,030,735 B2 | 4/2006 | Chen |
| 7,054,784 B2 | 5/2006 | Flentov et al. |
| 7,056,267 B2 | 6/2006 | Demas |
| 7,062,225 B2 | 6/2006 | White |
| 7,070,539 B2 | 7/2006 | Brown et al. |
| 7,072,789 B2 | 7/2006 | Vock et al. |
| 7,076,291 B2 | 7/2006 | Pulkkinen et al. |
| 7,085,678 B1 | 8/2006 | Burrell et al. |
| 7,086,990 B2 | 8/2006 | Chuang et al. |
| 7,091,863 B2 | 8/2006 | Ravet |
| 7,092,846 B2 | 8/2006 | Vock et al. |
| 7,097,588 B2 | 8/2006 | Watterson et al. |
| 7,142,107 B2 | 11/2006 | Kates |
| 7,144,830 B2 | 12/2006 | Hill et al. |
| 7,156,773 B2 | 1/2007 | Takai et al. |
| 7,163,489 B1 | 1/2007 | Nelson |
| 7,166,062 B1 | 1/2007 | Watterson et al. |
| 7,171,331 B2 | 1/2007 | Vock et al. |
| 7,173,437 B2 | 2/2007 | Hervieux et al. |
| 7,187,924 B2 | 3/2007 | Ohlenbusch et al. |
| 7,188,439 B2 | 3/2007 | DiBenedetto et al. |
| 7,191,803 B2 | 3/2007 | Orr et al. |
| 7,192,402 B2 | 3/2007 | Amano et al. |
| 7,200,517 B2 | 4/2007 | Darley et al. |
| 7,203,158 B2 | 4/2007 | Oshima et al. |
| 7,206,630 B1 | 4/2007 | Tarler |
| 7,209,771 B2 | 4/2007 | Twitchell, Jr. |
| 7,215,991 B2 | 5/2007 | Besson et al. |
| 7,216,034 B2 | 5/2007 | Vitikainen et al. |
| 7,220,220 B2 | 5/2007 | Stubbs et al. |
| 7,251,454 B2 | 7/2007 | White |
| 7,254,368 B1 | 8/2007 | Okada et al. |
| 7,254,516 B2 | 8/2007 | Case, Jr. et al. |
| 7,273,431 B2 | 9/2007 | DeVall |
| 7,292,867 B2 | 11/2007 | Werner et al. |
| 7,298,327 B2 | 11/2007 | Dupray et al. |
| 7,353,139 B1 | 4/2008 | Burrell et al. |
| 7,357,756 B2 | 4/2008 | Demas |
| 7,383,081 B2 | 6/2008 | Butt et al. |
| 7,398,151 B1 | 7/2008 | Burrell et al. |
| 7,428,472 B2 | 9/2008 | Darley et al. |
| 7,457,724 B2 | 11/2008 | Vock et al. |
| 7,467,060 B2 | 12/2008 | Kulach et al. |
| 7,480,512 B2 | 1/2009 | Graham et al. |
| 7,484,320 B2 | 2/2009 | Butt et al. |
| 7,552,031 B2 | 6/2009 | Vock et al. |
| 7,559,127 B2 | 7/2009 | Rooney et al. |
| 7,607,243 B2 | 10/2009 | Berner et al. |
| 7,670,263 B2 | 3/2010 | Ellis et al. |
| 7,698,101 B2 | 4/2010 | Alten et al. |
| 7,771,320 B2 | 8/2010 | Riley et al. |
| 7,839,382 B2 | 11/2010 | Ueshima et al. |
| 7,891,666 B2 | 2/2011 | Kuenzler et al. |
| 7,893,842 B2 | 2/2011 | Deutsch |
| 7,907,779 B2 | 3/2011 | Kawamoto et al. |
| 8,188,868 B2 | 5/2012 | Case, Jr. |
| 8,360,904 B2 | 1/2013 | Oleson et al. |
| 2001/0003542 A1 | 6/2001 | Kita |
| 2002/0019296 A1 | 2/2002 | Freeman et al. |
| 2002/0021407 A1 | 2/2002 | Elliott |
| 2002/0049535 A1 | 4/2002 | Rigo et al. |
| 2002/0068873 A1 | 6/2002 | Nissila |
| 2002/0077534 A1 | 6/2002 | DuRousseau |
| 2002/0094776 A1 | 7/2002 | Pulver |
| 2002/0102988 A1 | 8/2002 | Myllymaki |
| 2002/0107433 A1 | 8/2002 | Mault |
| 2002/0160883 A1 | 10/2002 | Dugan |
| 2002/0165771 A1 | 11/2002 | Walker et al. |
| 2003/0009308 A1 | 1/2003 | Kirtley |
| 2003/0028377 A1 | 2/2003 | Noyes |
| 2003/0088196 A1 | 5/2003 | Steve |
| 2003/0091964 A1 | 5/2003 | Yeager |
| 2003/0097878 A1 | 5/2003 | Farringdon et al. |
| 2003/0100315 A1 | 5/2003 | Rankin |
| 2003/0108217 A1 | 6/2003 | Tilbury et al. |
| 2003/0109298 A1 | 6/2003 | Oishi et al. |
| 2003/0139254 A1 | 7/2003 | Chang |
| 2003/0149526 A1 | 8/2003 | Zhou et al. |
| 2003/0160732 A1 | 8/2003 | Van Heerden et al. |
| 2003/0163283 A1 | 8/2003 | O'Brien |
| 2003/0163287 A1 | 8/2003 | Vock et al. |
| 2003/0171189 A1 | 9/2003 | Kaufman |
| 2003/0191578 A1 | 10/2003 | Paulauskas et al. |
| 2003/0208409 A1 | 11/2003 | Mault |
| 2003/0216228 A1 | 11/2003 | Rast |
| 2003/0224337 A1 | 12/2003 | Shum et al. |
| 2003/0228934 A1 | 12/2003 | Corzilius et al. |
| 2004/0009731 A1 | 1/2004 | Rabinowicz |
| 2004/0023761 A1 | 2/2004 | Emery |
| 2004/0046692 A1 | 3/2004 | Robson et al. |
| 2004/0063468 A1 | 4/2004 | Frank |
| 2004/0063481 A1 | 4/2004 | Wang |
| 2004/0082414 A1 | 4/2004 | Knox |
| 2004/0102247 A1 | 5/2004 | Smoot et al. |
| 2004/0102931 A1 | 5/2004 | Ellis et al. |
| 2004/0116784 A1 | 6/2004 | Gavish |
| 2004/0116837 A1 | 6/2004 | Yamaguchi et al. |
| 2004/0171956 A1 | 9/2004 | Babashan |
| 2004/0177531 A1 | 9/2004 | DiBenedetto et al. |
| 2004/0199056 A1 | 10/2004 | Husemann et al. |
| 2004/0203789 A1 | 10/2004 | Hammond et al. |
| 2004/0203873 A1 | 10/2004 | Gray |
| 2004/0209600 A1 | 10/2004 | Werner et al. |
| 2005/0010096 A1 | 1/2005 | Blackadar |
| 2005/0046576 A1 | 3/2005 | Julian et al. |
| 2005/0049113 A1 | 3/2005 | Yueh et al. |
| 2005/0054941 A1 | 3/2005 | Ting et al. |
| 2005/0085316 A1 | 4/2005 | Barr |
| 2005/0096933 A1 | 5/2005 | Collins et al. |
| 2005/0121504 A1 | 6/2005 | Sanders et al. |
| 2005/0124463 A1 | 6/2005 | Yeo et al. |
| 2005/0172311 A1 | 8/2005 | Hjelt et al. |
| 2005/0192025 A1 | 9/2005 | Kaplan |
| 2005/0195094 A1 | 9/2005 | White |
| 2005/0197063 A1 | 9/2005 | White |
| 2005/0202905 A1 | 9/2005 | Chesser |
| 2005/0209050 A1 | 9/2005 | Bartels |
| 2005/0227811 A1 | 10/2005 | Shum et al. |
| 2005/0233815 A1 | 10/2005 | McCreary et al. |
| 2005/0240865 A1 | 10/2005 | Atkins et al. |
| 2005/0250458 A1 | 11/2005 | Graham et al. |
| 2005/0256416 A1 | 11/2005 | Chen |
| 2005/0259002 A1 | 11/2005 | Erario et al. |
| 2005/0266961 A1 | 12/2005 | Shum et al. |
| 2005/0287499 A1 | 12/2005 | Yeager |
| 2006/0004265 A1 | 1/2006 | Pulkkinen et al. |
| 2006/0020177 A1 | 1/2006 | Seo et al. |
| 2006/0020421 A1 | 1/2006 | Darley et al. |
| 2006/0025282 A1 | 2/2006 | Redmann |
| 2006/0047208 A1 | 3/2006 | Yoon |
| 2006/0073807 A1 | 4/2006 | Baker |
| 2006/0082472 A1 | 4/2006 | Adachi et al. |
| 2006/0084851 A1 | 4/2006 | Lee et al. |
| 2006/0126861 A1 | 6/2006 | Saliterman |
| 2006/0135297 A1 | 6/2006 | Cruciani |
| 2006/0136173 A1 | 6/2006 | Case, Jr. et al. |
| 2006/0148594 A1 | 7/2006 | Saintoyant et al. |
| 2006/0156356 A1 | 7/2006 | Sato et al. |
| 2006/0169125 A1 | 8/2006 | Ashkenazi et al. |
| 2006/0178235 A1 | 8/2006 | Coughlan et al. |
| 2006/0184427 A1 | 8/2006 | Singh |

(56) References Cited

U.S. PATENT DOCUMENTS

| | | |
|---|---|---|
| 2006/0189360 A1 | 8/2006 | White |
| 2006/0203972 A1 | 9/2006 | Hays |
| 2006/0205564 A1 | 9/2006 | Peterson |
| 2006/0229161 A1 | 10/2006 | Demas |
| 2006/0229163 A1 | 10/2006 | Waters |
| 2006/0230640 A1 | 10/2006 | Chen |
| 2006/0234832 A1 | 10/2006 | Toyama et al. |
| 2006/0240865 A1 | 10/2006 | White |
| 2006/0246869 A1 | 11/2006 | Ohlenbusch et al. |
| 2006/0252600 A1 | 11/2006 | Grogan et al. |
| 2006/0253210 A1 | 11/2006 | Rosenberg |
| 2006/0277067 A1 | 12/2006 | Jang et al. |
| 2007/0006489 A1 | 1/2007 | Case, Jr. et al. |
| 2007/0011919 A1 | 1/2007 | Case, Jr. |
| 2007/0018952 A1 | 1/2007 | Arseneau et al. |
| 2007/0021269 A1 | 1/2007 | Shum |
| 2007/0032318 A1 | 2/2007 | Nishimura et al. |
| 2007/0044346 A1 | 3/2007 | Ungari et al. |
| 2007/0049461 A1 | 3/2007 | Kim et al. |
| 2007/0059675 A1 | 3/2007 | Kuenzler et al. |
| 2007/0060425 A1 | 3/2007 | Kuenzler et al. |
| 2007/0061105 A1 | 3/2007 | Darley et al. |
| 2007/0118043 A1 | 5/2007 | Oliver et al. |
| 2007/0123391 A1 | 5/2007 | Shin et al. |
| 2007/0146116 A1 | 6/2007 | Kimbrell |
| 2007/0149361 A1 | 6/2007 | Jung et al. |
| 2007/0157488 A1 | 7/2007 | Guzman |
| 2007/0159926 A1 | 7/2007 | Prstojevich et al. |
| 2007/0177801 A1 | 8/2007 | Kawamoto et al. |
| 2007/0179816 A1 | 8/2007 | Lemme |
| 2007/0191083 A1 | 8/2007 | Kuenzler et al. |
| 2007/0203665 A1 | 8/2007 | Darley et al. |
| 2007/0208531 A1 | 9/2007 | Darley et al. |
| 2007/0219057 A1 | 9/2007 | Fleishman |
| 2007/0219058 A1 | 9/2007 | Fleishman |
| 2007/0232455 A1 | 10/2007 | Hanoun |
| 2007/0239565 A1 | 10/2007 | Pentel |
| 2007/0247306 A1 | 10/2007 | Case, Jr. |
| 2007/0260421 A1 | 11/2007 | Berner, Jr. et al. |
| 2007/0271065 A1 | 11/2007 | Gupta et al. |
| 2007/0271116 A1 | 11/2007 | Wysocki et al. |
| 2007/0287596 A1 | 12/2007 | Case et al. |
| 2007/0293370 A1 | 12/2007 | Klingler |
| 2008/0002528 A1 | 1/2008 | Andren et al. |
| 2008/0004510 A1 | 1/2008 | Tanzawa et al. |
| 2008/0009275 A1 | 1/2008 | Werner et al. |
| 2008/0051993 A1 | 2/2008 | Graham et al. |
| 2008/0058971 A1 | 3/2008 | Graham et al. |
| 2008/0059064 A1 | 3/2008 | Werner et al. |
| 2008/0065319 A1 | 3/2008 | Graham et al. |
| 2008/0067244 A1 | 3/2008 | Marks |
| 2008/0076637 A1 | 3/2008 | Gilley et al. |
| 2008/0076972 A1 | 3/2008 | Dorogusker et al. |
| 2008/0077489 A1 | 3/2008 | Gilley et al. |
| 2008/0077619 A1 | 3/2008 | Gilley et al. |
| 2008/0077620 A1 | 3/2008 | Gilley et al. |
| 2008/0077881 A1 | 3/2008 | Gilley et al. |
| 2008/0080700 A1 | 4/2008 | Mock et al. |
| 2008/0086318 A1 | 4/2008 | Gilley et al. |
| 2008/0088303 A1 | 4/2008 | Englert |
| 2008/0101161 A1 | 5/2008 | Imai et al. |
| 2008/0103689 A1 | 5/2008 | Graham et al. |
| 2008/0125288 A1 | 5/2008 | Case |
| 2008/0201639 A1 | 8/2008 | Shoman |
| 2008/0258921 A1 | 10/2008 | Woo et al. |
| 2008/0269017 A1 | 10/2008 | Ungari |
| 2008/0319661 A1 | 12/2008 | Werner et al. |
| 2009/0024601 A1 | 1/2009 | Zmolek |
| 2010/0042427 A1 | 2/2010 | Graham et al. |
| 2010/0201352 A1 | 8/2010 | Englert |
| 2011/0119022 A1 | 5/2011 | Kuenzler et al. |
| 2011/0190053 A1 | 8/2011 | Kawamoto et al. |

FOREIGN PATENT DOCUMENTS

| | | |
|---|---|---|
| CN | 101031101 A | 9/2007 |
| DE | 29701308 | 5/1997 |
| DE | 10160528 | 6/2003 |
| DE | 10338620 | 3/2005 |
| DE | 102006013732 | 7/2007 |
| EP | 0472110 A2 | 2/1992 |
| EP | 0908701 | 4/1999 |
| EP | 1062994 | 12/2000 |
| EP | 1128358 A1 | 8/2001 |
| EP | 1253404 | 10/2002 |
| EP | 1457128 A2 | 9/2004 |
| EP | 1707065 * | 10/2006 |
| FR | 2754723 A1 | 4/1998 |
| FR | 2885816 | 11/2006 |
| JP | 9-173645 | 7/1997 |
| JP | 10329452 | 12/1998 |
| JP | H11-052834 A | 2/1999 |
| JP | H11-178967 A | 7/1999 |
| JP | 2001-327472 A | 11/2001 |
| JP | 2003-175139 A | 6/2003 |
| JP | 2003-339908 A | 12/2003 |
| JP | 2004-519058 A | 6/2004 |
| JP | 2004-247954 | 9/2004 |
| JP | 2004-261608 A | 9/2004 |
| JP | 2005-000471 | 1/2005 |
| JP | 2005-323967 A | 11/2005 |
| JP | 2006034717 A | 2/2006 |
| JP | 2007312246 | 11/2007 |
| JP | 2008073209 | 4/2008 |
| WO | WO 96/05766 | 2/1996 |
| WO | WO 96/23561 | 8/1996 |
| WO | WO 98/11528 | 3/1998 |
| WO | WO 98/58236 | 12/1998 |
| WO | WO 99/07153 | 2/1999 |
| WO | WO 99/18480 | 4/1999 |
| WO | WO 99/44016 | 9/1999 |
| WO | WO 99/49279 | 9/1999 |
| WO | WO 00/33031 | 6/2000 |
| WO | WO 02/50652 | 6/2002 |
| WO | WO 02/067449 | 8/2002 |
| WO | WO 2004/015606 A1 | 2/2004 |
| WO | WO 2006/085237 | 8/2006 |
| WO | WO 2006/086487 | 8/2006 |
| WO | WO 2004/042666 | 5/2007 |

OTHER PUBLICATIONS

Adidas Introduces the 1, the Most Advanced Shoe Ever Made, at http://www.press.adidas.com/en/DesktopDefault.aspx/tabid-16/94_read-341/ 1 page, May 10, 2004.

Bramanti, M., "Consider the GPS for Biomedial Applications," IEEE Engineering in Medicine and Biology, Jul./Aug. 1996, pp. 16-17.

Chalk, David, "High-tech ways to battle the bulge," at http://www.canada.com/topics/technology/columnists/story.html?id=45593557-8cb2-40d5-9e7a-fdldbale661d, 2 pages, Jun. 7, 2006.

Dance Dance Revolution, at http://en.wikipedia.org/wiki/Dance_Dance_Revolution, 11 pages, last modified Nov. 17, 2007.

Diamond Multimedia Systems, Inc., "Rio PMP300 User's Guide," 1998.

Ditlea, S., "Real Men Don't Ask Directions," Popular Science, vol. 246, No. 3, Mar. 1995, pp. 86-89, 120-121.

Evans, AL, et al. "Recording accelerations in body movements," Med. & Biol. Eng. & Comput., 1991, 29, pp. 102-104.

EyeToy, at http://en.wikipedia.org/wiki/EyeToy, 5 pages, last modified Nov. 14, 2007.

EyeToy: AntiGrav, at http://en.wikipedia.org/wiki/EyeToy:_AntiGrav, 2 pages, last modified Nov. 13, 2007.

EyeToy: Groove, at http://en.wikipedia.org/wiki/EyeToy:_Groove, 1 page, last modified Nov. 13, 2007.

EyeToy: Play 2, at http://en.wikipedia.org/wiki/EyeToy:_Play_2, 1 page, last modified Nov. 13, 2007.

(56) References Cited

OTHER PUBLICATIONS

EyeToy: Play 3, at http://en.wikipedia.org/wiki/EyeToy:_Play_3, 1 page, last modified Nov. 13, 2007.
EZ2Dancer, at http://en.wikipedia.org/wiki/EZ2Dancer, 3 pages, last modified Nov. 7, 2007.
Garmin Corp., "GPS 40 Personal Navigator, Owner's Manual," Jun. 1994, 67 pgs.
Garmin Corp., "GPS 95 XL Personal Navigator, Owner's Manual," Aug. 1994, 140 pgs.
Garmin International, Inc., Navtalk; Cellular Phones/GPS Receiver; Owner's Manual and Reference Guide; 1999-2000; Garmin Corp., 128 pages.
Garmin LTD; *Navtalk*; Product information, 6 pages. (No Date).
Gouskos, Carrie, "EyeToy: Kinetic Review, EyeToy: Kinetic offers a surprisingly good personal training program but does make hearty demands of your lighting and space requirements." at http://www.gamespot.com/ps2/sports/eyetoykinetic/review.htm 2 pages, Nov. 29, 2005.
GPSII, Garmin Owner's Manual 7 Reference, 108 pgs, Aug. 1996, Garmin Corp., Kansas, USA.
GPSII, Garmin Owner's Manual 7 Reference, 100 pgs, Aug. 1997, Garmin Corp., Kansas, USA.
Hoyt, RW, et al. , "Ambulatory foot contact monitor to estimate metabolic cost of human locomotion," Journal of Applied Physiology, 1994, vol. 76, Issue 4, pp. 1818-1822.
In the Groove (game), at http://en.wikipedia.org/wiki/In_the_Groove_(game), 8 pages, printed Jan. 24, 2006.
In the Groove (video game), at http://en.wikipedia.org/wiki/In_The_Groove_(game), 9 pages, last modified Nov. 15, 2007.
Ion: New Learning Console From Hasbro's Playskool Division Gets Kids Up and Active, at http://www.hasbro.com/media/content/printable.cfm?release=291, 2 pages, Feb. 10, 2005.
Kilowatt—Isometric Home Gym Fitness Equipment from Powergrid Fitness, at www.powergridfitness.com/howItWorks/technology.aspx, 3 pages, printed Jan. 24, 2006.
Kirby Tilt 'n' Tumble, at http://en.wikipedia.org/wiki/Kirby_Tilt_'n'_Tumble, 2 pages, last modified Nov. 13, 2007.
Lodha et al. "Consistent visualization and querying of GIS databases by a location-aware mobile agent," Computer Graphics International, 2003, Proceedings; Jul. 9-11, 2003, pp. 249-253.
Losada et al. , "OISTI (an Oral-Interface System to provide Tourist-Information inside a car)," Information Technology: Coding and Computing, 2001, Proceedings; International Conference on Apr. 2-4, 2001, pp. 373-377.
Magellan GPS, NAVDLX-10 User Guide, 91 pgs, Magellan Systems Corp., 1995.
Magellan GPPS Satellite Navigator Reference Guide Trailblazer XL, 78 pgs, Magellan Systems Corp. (No Date).
Makikawa, M., et al. "Development of an Ambulatory Physical Activity and Behavior Map Monitoring System," 18th Annual International Conference of the IEEE Engineering in Medicine and Biology Society, Amsterdam 1996, pp. 71-72.
Mann, S "'WearCam' (The wearable camera): personal imagin systems for long-term use in wearable tetherless computer-mediated reality and personal photo/videographic memory prosthesis," Wearable Computers, 1998, Digest of Papers; Second International Symposium on, Oct. 19-20, 1998, pp. 124-131.
Mathie, M. J., et al. ,"Classification of basic daily movements using a triaxial accelerometer" Med. Biol Eng. Comput., 2004 42:679-687.
Mehaffey et al. ,"Garmin's Navtalk Cell Phone and Road Map GPS Product Review," Revision 2, Nov. 2, 1999, 5 pgs.
Nelson, RC., "A study to determine the biomechanics of running in skilled trackmen," US Department of Health, Education, and Welfare. Mar. 11, 1970.
Nike+iPod review, at http://jonas.rabbe.com/archives/2007/01/24/nikeipod-review/, 7 pages, Jan. 24, 2007.
On the go with Nike, iPod, at http://www.cnet.com.au/mp3players/accessories/0,239029103,240063171,00.htm, 2 pages, May 24, 2006.
Perrin, O., et al. , "Improvement of walking speed prediction by accelerometry and altimetry, validated by satellite positioning," Med. Biol. Comput., 2000, 38:164-168.
Police 911, at http://en.wikipedia.org/wiki/Police_911, 4 pages, last modified Nov. 13, 2007.
Power Pad, at http://en.wikipedia.org/wiki/Power_Pad, 2 pages, last modified Nov. 8, 2007.
Pump It Up, at http://en.wikipedia.org/wiki/Pump_It_Up, 17 pages, last modified Nov. 14, 2007.
QMotions Active Game Technologies—Motions-Golf, at www.qmotions.com/about_qmotions-golf/how_it_works.aspx, 2 pages, printed Jan. 24, 2006.
QMotions Active Game Technologies—QMotions-Golf, at www.qmotions.com/about_qmotions-golf/what_is_it.aspx, 2 pages, printed Jan. 24, 2006.
QMotions Active Game Technologies—Qmotions-Baseball, at www.qmotions.com/about_qmotions-baseball/BBhow_it_works.aspx, 4 pages, printed Jan. 24, 2006.
Raphael, Glen, "Mocap Boxing" at http://videogameworkout.com/2005/09/mocap-boxing.html, 3 pages, Sep. 15, 2005.
Richtel, M., "Surfing for Music," Popular Science, Sep. 1999, pp. 70-74.
Rojas, Peter, "Adidas 1 review," at http://www.engadget.com/2005/03/22/adidas-1-review/, 9 pages, Mar. 22, 2005.
Roper, Chris, "EyeToy: Kinetic, We never knew playing videogames could get us into shape," at http://ps2.ign.com/articles/669/669004p1.html, 5 pages, Nov. 22, 2005.
Sawhney et al. , "Speaking and listening on the run: Design for wearable audio computing," Speech Interface Group, MIT Laboratory, Oct. 19-20, 1998, Pittburgh, PA.
Silvia, F., et al. , "Homogeneous access to temporal data and interaction in visual interface for databases," User Interfaces to Data Intensive Systems, 1999, Proceedings; Sep. 5-6, 1999, pp. 108-117.
Speer, Justin, "E3 2001 Hands-onPolice 911. Konami's hit motion-sensitive light-gun game gets ready to kick down the door of the PS2.",at http://www.gamespot.com/ps2/action/police911/news.html?sid=2762376, 1 page, May 19, 2001.
StepMania, at http://en.wikipedia.org/wiki/StepMania, 2 pages, last modified Nov. 17, 2007.
Sun, W., et al. , "A self-coherence anti-jamming GPS receiver," Signal Processing, IEEE Transactions on, vol. 53, Issue 10, Part 1, Oct. 2005, pp. 3910-3915.
Technology Manala® GX Video Gesture Control (VGC) System Concept, at http://www.gesturetek.com/gestxtreme/introduction.php, 3 pages, posted Oct. 29, 2005.
Tucker, R., et al. , "A microprocessor-based fitness monitor with analog voice feedback for runners," IEEE Case Studies in Medical Instrument Design, 1991, pp. 163-170.
Extended European Search Report for Application No. EP 08014368.8, Applicant: adidas International, mailed Aug. 24, 2010.
Extended European Search Report for Application No. EP 08014429.8, Applicant: adidas International, mailed Aug. 24, 2010.
Extended European Search Report for Application No. EP 08014499.1, Applicant: adidas International, mailed Dec. 29, 2008.
Office Action issued in European Application No. 08 014 429.8, May 6, 2015.
Office Action issued in Japanese Application No. 2012-257323, dispatched Feb. 24, 2015.
Office Action issued in European Application No. 11168446.0, issued Dec. 12, 2014.

\* cited by examiner

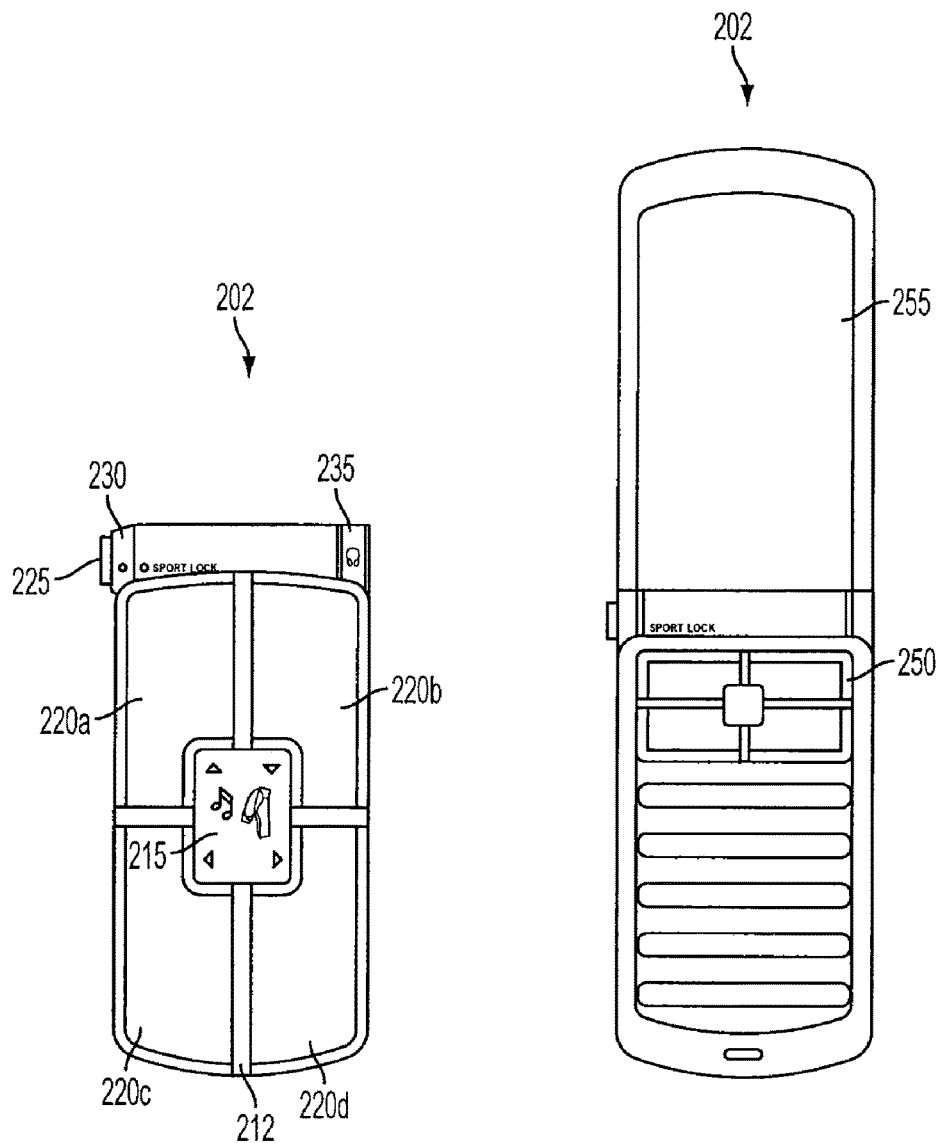

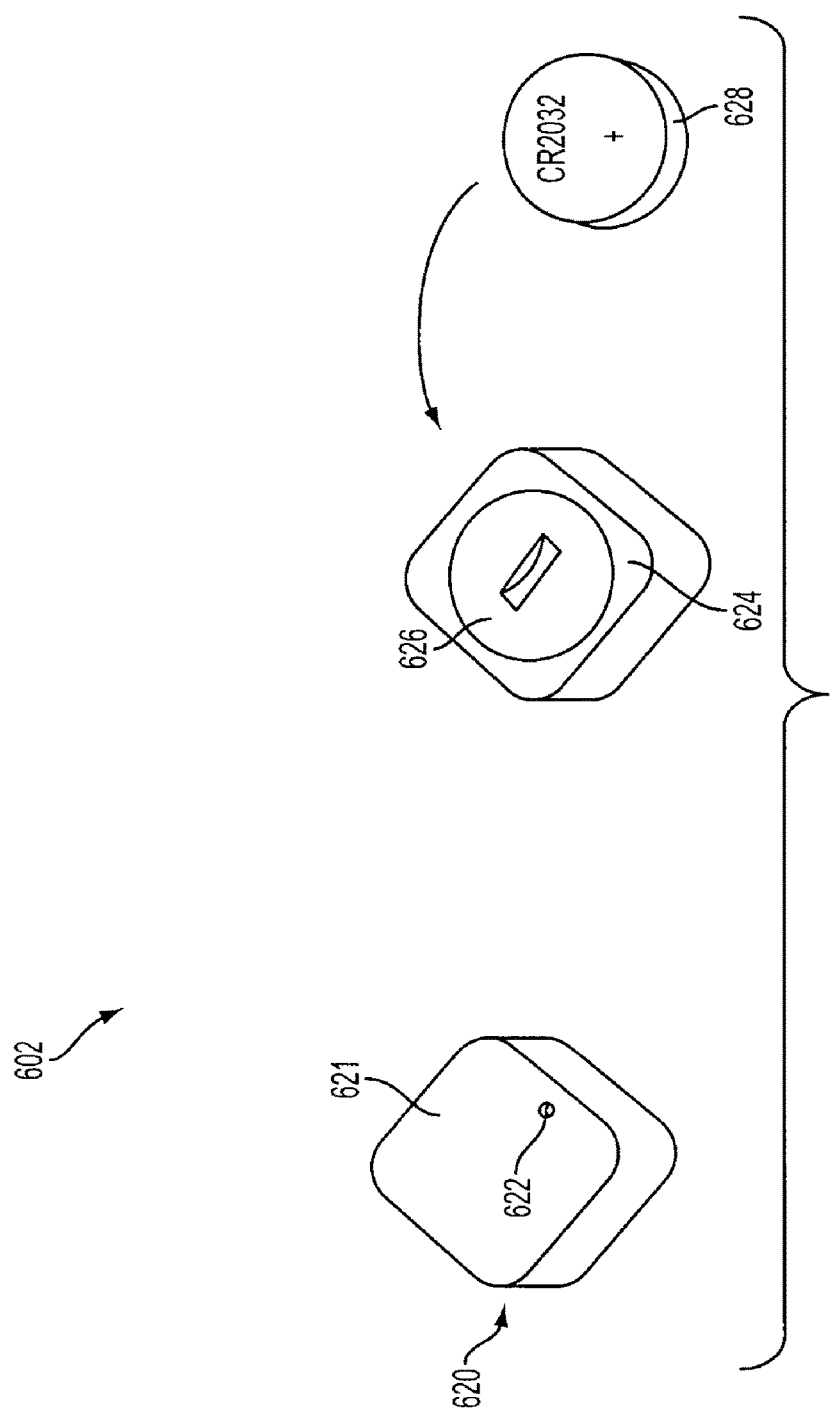

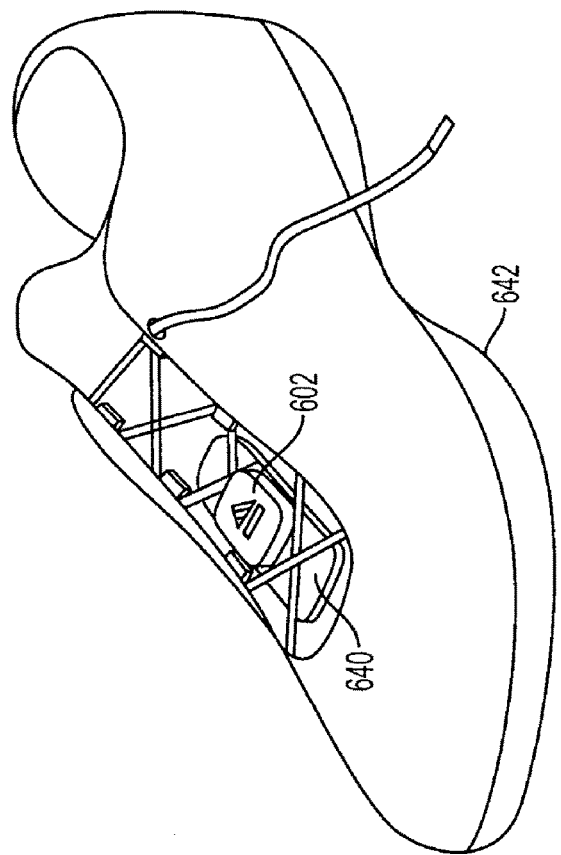
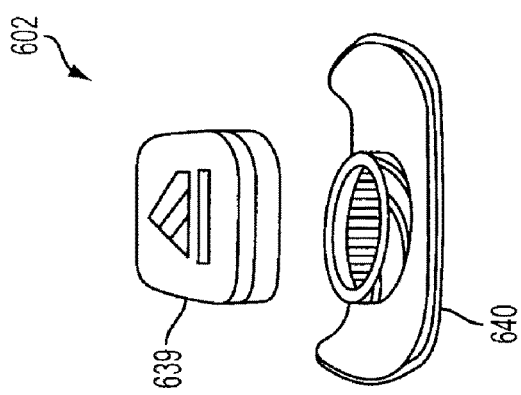
FIG. 6E
FIG. 6F

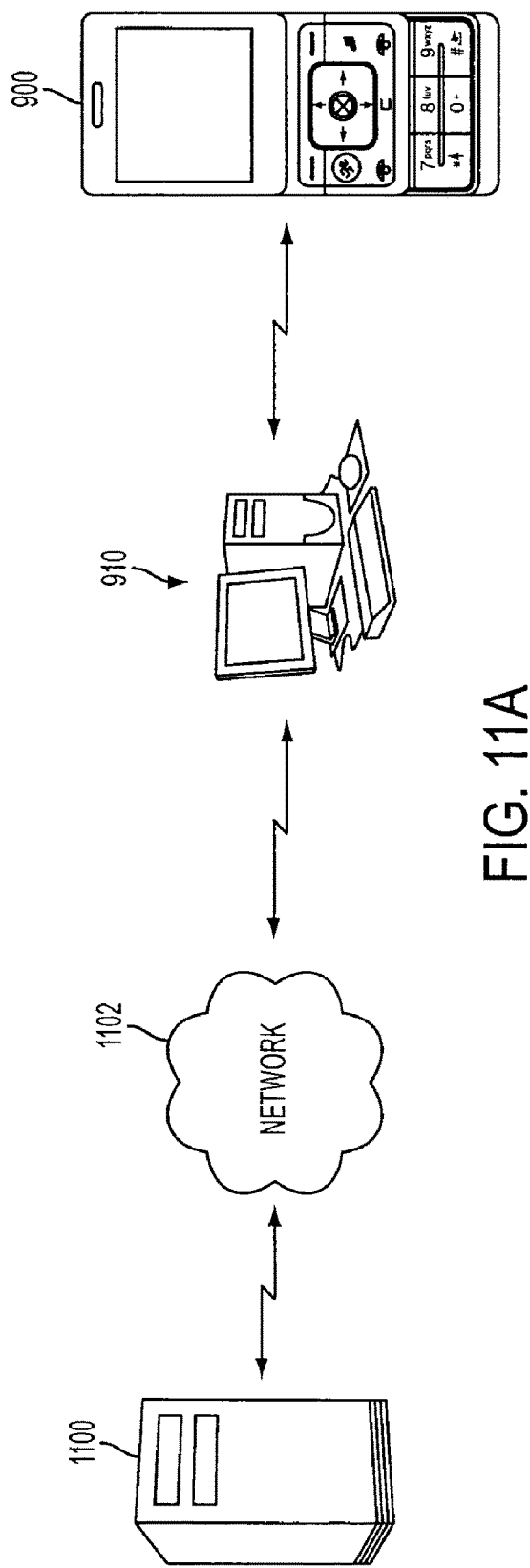

EXAMPLE NARRATION TABLE

| TRIGGER POINT | ACTION | EXAMPLE FEEDBACK | | |
|---|---|---|---|---|
| | | EXAMPLE 1 | EXAMPLE 2 | EXAMPLE 3 |
| START BUTTON | START WORKOUT | BEGIN WORKOUT<br>LET'S GET STARTED | BEGIN WORKOUT<br>LET'S GET STARTED | BEGIN WORKOUT<br>LET'S GET STARTED |
| | SPEED UP TO STRENGTH ZONE | ACCELERATE TO STRENGTH ZONE<br>SPEED UP TO STRENGTH ZONE | ACCELERATE TO YELLOW ZONE<br>SPEED UP TO YELLOW ZONE | ACCELERATE TO __ BPM<br>SPEED UP TO __ BPM |
| | ENTERING STRENGTH ZONE | ENTERING STRENGTH ZONE | ENTERING YELLOW ZONE | APPROACHING __ BPM |
| | ZONE ACHIEVED | STRENGTH ZONE ACHIEVED<br>STRENGTH ZONE | YELLOW ZONE ACHIEVED<br>YELLOW ZONE | __ BPM ACHIEVED<br>__ BPM |
| HEART RATE LOW | INCREASE HEART RATE | ACCELERATE TO STRENGTH ZONE<br>SPEED UP TO STRENGTH ZONE | ACCELERATE TO YELLOW ZONE<br>SPEED UP TO YELLOW ZONE | ACCELERATE TO __ BPM<br>SPEED UP TO __ BPM |
| 5 BEATS BELOW TARGET ZONE<br>REPEAT EVERY 3 MINUTES IF STILL NOT IN ZONE<br>REPEAT IF WAS IN ZONE AND WENT BELOW AGAIN | | | | |
| HEART RATE HIGH | DECREASE HEART RATE | EASE BACK TO STRENGTH ZONE<br>SLOW DOWN TO STRENGTH ZONE | SLOW DOWN TO YELLOW ZONE<br>EASE BACK TO YELLOW ZONE | SLOW DOWN TO __ BPM |
| 5 BEATS ABOVE TARGET ZONE<br>REPEAT EVERY 3 MINUTES IF STILL NOT IN ZONE<br>REPEAT IF WAS IN ZONE AND WENT ABOVE AGAIN | | | | |
| HEART RATE MIDPOINT OF RANGE REACHED | MAINTAIN HEART RATE | MAINTAIN STRENGTH ZONE<br>STRENGTH ZONE<br>STRENGTH ZONE ACHIEVED<br>MAINTAIN STRENGTH ZONE FOR __<br>MAINTAIN SPEED FOR __ | YELLOW ZONE ACHIEVED<br>YELLOW ZONE<br>MAINTAIN YELLOW ZONE FOR __ | __ BPM ACHIEVED<br>__ BPM |

FROM FIG. 14B

| PERCENT OF WORKOUT COMPLETED | UPDATE USER | | | |
|---|---|---|---|---|
| | 25% | ONE QUARTER COMPLETE<br>___ MINUTES LEFT TO GO<br>___ MINUTES OF WORKOUT LEFT | ONE QUARTER COMPLETE<br>___ MINUTES LEFT TO GO<br>___ MINUTES OF WORKOUT LEFT | ONE QUARTER COMPLETE<br>___ MINUTES LEFT TO GO<br>___ MINUTES OF WORKOUT LEFT |
| | 50% | HALFWAY DONE WORKOUT<br>___ MINUTES LEFT TO GO<br>___ MINUTES OF WORKOUT LEFT | HALFWAY DONE WORKOUT<br>___ MINUTES LEFT TO GO<br>___ MINUTES OF WORKOUT LEFT | HALFWAY DONE WORKOUT<br>___ MINUTES LEFT TO GO<br>___ MINUTES OF WORKOUT LEFT |
| | 75% | THREE QUARTERS COMPLETE<br>___ MINUTES LEFT TO GO<br>___ MINUTES OF WORKOUT LEFT | THREE QUARTERS COMPLETE<br>___ MINUTES LEFT TO GO<br>___ MINUTES OF WORKOUT LEFT | THREE QUARTERS COMPLETE<br>___ MINUTES LEFT TO GO<br>___ MINUTES OF WORKOUT LEFT |
| | 90% | ___ MINUTES LEFT TO GO<br>___ MINUTES OF WORKOUT LEFT | ___ MINUTES LEFT TO GO<br>___ MINUTES OF WORKOUT LEFT | ___ MINUTES LEFT TO GO<br>___ MINUTES OF WORKOUT LEFT |
| FINISHED WORKOUT | FINISHED | WORKOUT COMPLETE | WORKOUT COMPLETE | WORKOUT COMPLETE |
| | CONGRATULATIONS | NICE WORK<br>GOOD JOB | NICE WORK<br>GOOD JOB | NICE WORK<br>GOOD JOB |
| | COOLDOWN | ENTERING COOL DOWN<br>PLEASE WALK FOR ___<br>TIME TO COOL DOWN | ENTERING COOL DOWN<br>PLEASE WALK FOR ___<br>TIME TO COOL DOWN | ENTERING COOL DOWN<br>PLEASE WALK FOR ___<br>TIME TO COOL DOWN |

FIG. 14C

TABLE 1A - CALORIES BURNED BY WALKING/RUNNING (IN KCAL/MIN)(BASED ON BODY WEIGHT)

| | | BODY WEIGHT | | | | | | | | | | |
|---|---|---|---|---|---|---|---|---|---|---|---|---|
| | Kg | 50 | 53 | 56 | 59 | 62 | 68 | 71 | 74 | 77 | 80 | 86 |
| | LBS | 110 | 117 | 123 | 130 | 137 | 150 | 157 | 163 | 170 | 176 | 190 |
| WALKING: 2.0 MPH | | 2.2 | 2.3 | 2.5 | 2.6 | 2.7 | 3 | 3.1 | 3.2 | 3.4 | 3.5 | 3.8 |
| 3.0 MPH | | 3.1 | 3.2 | 3.4 | 3.6 | 3.8 | 4.2 | 4.3 | 4.5 | 4.7 | 4.9 | 5.3 |
| 4.0 MPH | | 4.5 | 3.7 | 3.9 | 4.1 | 4.3 | 4.8 | 5 | 5.2 | 5.4 | 5.6 | 6 |
| RUNNING: 5.0 MPH (12 MIN/MILE PACE) | | 7 | 7.4 | 7.8 | 8.3 | 8.7 | 9.5 | 9.9 | 10.4 | 10.8 | 11.2 | 12 |
| 6.0 MPH (10 MIN/MILE PACE) | | 8.8 | 9.3 | 9.8 | 10.3 | 10.9 | 11.9 | 12.4 | 13 | 13.5 | 14 | 15.1 |
| 7.0 MPH (8.5 MIN/MILE PACE) | | 10.1 | 10.7 | 11.3 | 11.9 | 12.5 | 13.7 | 14.3 | 14.9 | 15.5 | 16.1 | 17.3 |
| 8.0 MPH (7.5 MIN/MILE PACE) | | 11.8 | 12.5 | 13.2 | 13.9 | 14.6 | 16.1 | 16.8 | 17.5 | 18.2 | 18.9 | 20.3 |
| 9.0 MPH (6.5 MIN/MILE PACE) | | 13.1 | 13.9 | 14.7 | 15.5 | 16.3 | 17.9 | 18.6 | 19.4 | 20.2 | 21 | 22.6 |
| 10 MPH (6 MIN/MILE PACE) | | 14 | 14.8 | 15.7 | 16.5 | 17.4 | 19 | 19.9 | 20.7 | 21.6 | 22.4 | 24.1 |
| 10.9 MPH (5.5 MIN/MILE PACE) | | 15.8 | 16.7 | 17.6 | 18.6 | 19.5 | 21.4 | 22.4 | 23.3 | 24.3 | 25.2 | 27.1 |

FIG. 15E

TABLE 1B - CALORIES BURNED BY WALKING/RUNNING (IN KCAL/MIN)(BASED ON BODY WEIGHT)

| | | Kg | 89 | 92 | 95 | 98 | 101 | 104 | 107 | 110 | 113 | 116 | 119 |
|---|---|---|---|---|---|---|---|---|---|---|---|---|---|
| | | LBS | 196 | 203 | 209 | 216 | 223 | 229 | 236 | 243 | 249 | 256 | 262 |
| WALKING: | 2.0 MPH | | 3.9 | 4 | 4.2 | 4.3 | 4.4 | 4.6 | 4.7 | 4.8 | 4.9 | 5.1 | 5.2 |
| | 3.0 MPH | | 5.5 | 5.6 | 5.8 | 6 | 6.2 | 6.4 | 6.6 | 6.7 | 6.9 | 7.1 | 7.3 |
| | 4.0 MPH | | 6.2 | 6.4 | 6.7 | 6.9 | 7.1 | 7.3 | 7.5 | 7.7 | 7.9 | 8.1 | 8.3 |
| RUNNING: | 5.0 MPH (12 MIN/MILE PACE) | | 12.5 | 12.9 | 13.3 | 13.7 | 14.1 | 14.6 | 15 | 15.4 | 15.8 | 16.2 | 16.7 |
| | 6.0 MPH (10 MIN/MILE PACE) | | 15.6 | 16.1 | 16.6 | 17.2 | 17.7 | 18.2 | 18.7 | 19.3 | 19.8 | 20.3 | 20.8 |
| | 7.0 MPH (8.5 MIN/MILE PACE) | | 17.9 | 18.5 | 19.1 | 19.7 | 20.3 | 20.9 | 21.5 | 22.1 | 22.7 | 23.3 | 23.9 |
| | 8.0 MPH (7.5 MIN/MILE PACE) | | 21 | 21.7 | 22.4 | 23.2 | 23.9 | 24.6 | 25.3 | 26 | 26.7 | 27.4 | 28.1 |
| | 9.0 MPH (6 MIN/MILE PACE) | | 23.4 | 24.2 | 24.9 | 25.7 | 26.5 | 27.3 | 28.1 | 28.9 | 29.7 | 30.5 | 31.2 |
| | 10 MPH (6 MIN/MILE PACE) | | 24.9 | 25.8 | 26.6 | 27.4 | 28.3 | 29.1 | 30 | 30.8 | 31.6 | 32.5 | 33.3 |
| | 10.9 MPH (5.5 MIN/MILE PACE) | | 28 | 29 | 29.9 | 30.9 | 31.8 | 32.8 | 33.7 | 34.7 | 35.6 | 36.5 | 37.5 |

BODY WEIGHT

FIG. 15F

TABLE 2

| | ORIGINAL METS RANGE | AVERAGE METS | %HR |
|---|---|---|---|
| BEGINNER | | | |
| ENERGY | 3.3-5.0 | 4.15 | 60-70 |
| RECOVERY AFTER FREE RUN | 4.2 | 4.2 | 60-70 |
| ENDURANCE | 5.0-8.0 | 6.5 | 71-80 |
| FREE RUN | 8 | 8 | LESS THAN 90% |
| INTERMEDIATE | | | |
| ENERGY | 7-9 | 8 | 65-75 |
| ENDURANCE | 10-12 | 11 | 75-85 |
| STRENGTH | 12-16 | 14 | 86-92 |
| LEG STRENGTH | 15 | 15 | LESS THAN 90% |
| ADVANCED | | | |
| ENERGY | 7-10 | 8.5 | 65-75 |
| ENDURANCE | 11-12 | 11.5 | 80-85 |
| STRENGTH | 12-14.5 | 13.25 | 85-90 |
| POWER | 15-18 | 16.5 | 90-95 |
| LEG STRENGTH | 15 | 15 | LESS THAN 90% |

FIG. 15G

| FITNESS LEVEL | | | | | | |
|---|---|---|---|---|---|---|
| AGE | BEGIN 1 | BEGIN 2 | INT 1 | INT 2 | INT 3 | ADVAN |
| MALES | | | | | | |
| 20-24 | < 43 | 44-50 | 51-58 | 59-63 | 64-68 | 69+ |
| 25-29 | < 42 | 43-48 | 49-55 | 56-60 | 61-65 | 66+ |
| 30-34 | < 40 | 41-45 | 46-53 | 54-57 | 58-62 | 63+ |
| 35-39 | < 38 | 39-43 | 44-50 | 51-55 | 56-60 | 61+ |
| 40-44 | < 35 | 36-41 | 42-48 | 49-52 | 53-57 | 58+ |
| 45-49 | < 34 | 35-39 | 40-45 | 46-49 | 50-54 | 55+ |
| 50-54 | < 32 | 33-36 | 37-43 | 44-47 | 48-52 | 53+ |
| 55-59 | < 30 | 31-34 | 35-41 | 42-45 | 46-49 | 50+ |
| 60-65 | < 28 | 29-32 | 33-38 | 39-42 | 43-46 | 47+ |
| FEMALES | | | | | | |
| 20-24 | < 36 | 37-41 | 42-46 | 47-51 | 52-57 | 58+ |
| 25-29 | < 35 | 36-40 | 41-44 | 45-49 | 50-55 | 56+ |
| 30-34 | < 33 | 34-37 | 38-42 | 43-46 | 47-52 | 53+ |
| 35-39 | < 31 | 32-35 | 36-40 | 41-44 | 45-50 | 51+ |
| 40-44 | < 29 | 30-33 | 34-37 | 38-41 | 42-47 | 48+ |
| 45-49 | < 27 | 28-31 | 32-35 | 36-38 | 39-44 | 45+ |
| 50-54 | < 25 | 26-29 | 30-32 | 33-36 | 37-42 | 43+ |
| 55-59 | < 23 | 24-27 | 28-30 | 31-33 | 34-39 | 40+ |
| 60-65 | < 21 | 22-24 | 25-27 | 28-30 | 31-36 | 37+ |

FIG. 27

| MUSIC RHYTHM | STRIDES |
|---|---|
| EVERY STEP | |
| 2ND STEP | |
| 3RD STEP | |
| 4TH STEP | |
| 5TH STEP | |

FIG. 36

SPORTS ELECTRONIC TRAINING SYSTEM, AND APPLICATIONS THEREOF

CROSS-REFERENCE TO RELATED APPLICATIONS

This application is a continuation of U.S. patent application Ser. No. 14/734,808, filed Jun. 9, 2015, which is a continuation of U.S. patent application Ser. No. 13/740,966, filed Jan. 14, 2013, now U.S. Pat. No. 9,087,159, which is a continuation of U.S. patent application Ser. No. 11/889,978, filed Aug. 17, 2007, now U.S. Pat. No. 8,360,904. The contents of each of these applications are expressly incorporated herein by reference thereto in their entireties.

This application is also related to commonly owned U.S. patent application Ser. No. 11/892,023, filed Aug. 17, 2007, commonly owned U.S. Pat. No. 8,221,290, issued Jul. 17, 2012, commonly owned U.S. Pat. No. 7,927,253, issued Apr. 19, 2011, and commonly owned U.S. patent application Ser. No. 13/546,458, filed Jul. 11, 2012, the disclosure of each of which is incorporated herein by reference thereto in its entirety.

FIELD OF THE INVENTION

The present invention generally relates to sports electronics. More particularly, the present invention relates to a sports electronic training system, and applications thereof.

BACKGROUND OF THE INVENTION

Exercise is important to maintaining a healthy lifestyle and individual well-being. Accordingly, many individuals want to participate in an exercise program. The most successful exercise programs are ones tailored to a fitness level of an individual and aimed at assisting the individual to achieve one or more specific fitness or exercise goals.

Sports trainers, as well as other exercise and fitness professionals, are available to assist individuals in developing exercise programs appropriate for their individual fitness levels and their specific fitness or exercise goals. Hiring such professionals, however, can be expensive. Furthermore, the busy schedules of many individuals make it difficult for these individuals to set aside time to meet with an exercise and fitness professional on a routine basis. Thus, many individuals forego using the services of exercise and fitness professionals, and they never achieve the benefits that can be obtained from an exercise program tailored, for example, to one's fitness level.

What is needed are new systems and methods that make it easier for individuals to exercise at a level appropriate for their fitness, and which enable individuals to achieve specific fitness or exercise goals.

BRIEF SUMMARY OF THE INVENTION

The present invention provides a sports electronic training system, and applications thereof. In an embodiment, the system comprises at least one monitor and an electronic processing device for receiving data from the at least one monitor and providing feedback to an individual based on the received data. The monitor can be a motion monitor that determines an individual's performance such as, for example, speed, pace and distance for a runner.

It is a feature of the present invention that it can assess a fitness level for an individual. It is also a feature of the present invention that it can provide feedback to an individual, for example, aimed at assisting the individual to achieve one or more specific fitness or exercise goals.

Further embodiments, features, and advantages of the present invention, as well as the structure and operation of the various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIGS. 2B-C are diagrams of an example mobile phone having a sports operating mode according to an embodiment of the present invention.

Figure 2A:
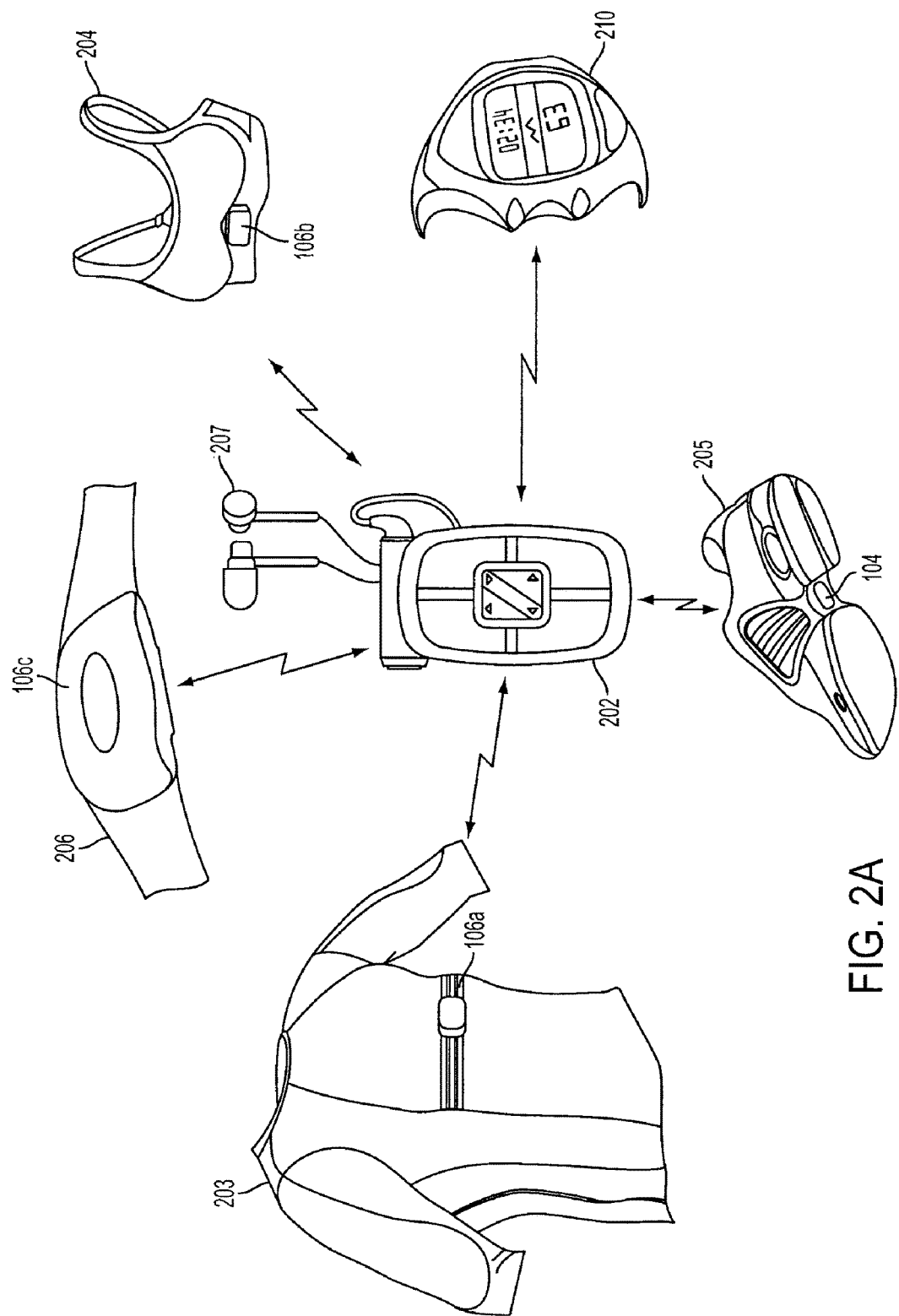
FIG. 2A is a diagram illustrating selected components of a sports electronic training system according to an embodiment of the present invention.
Figure 2F:
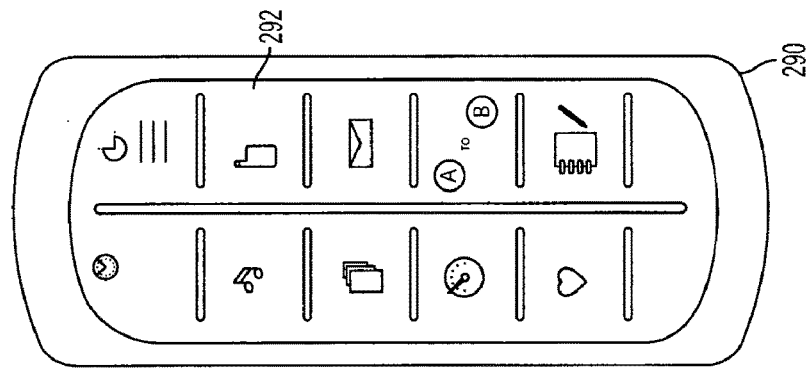
Figure 2E:
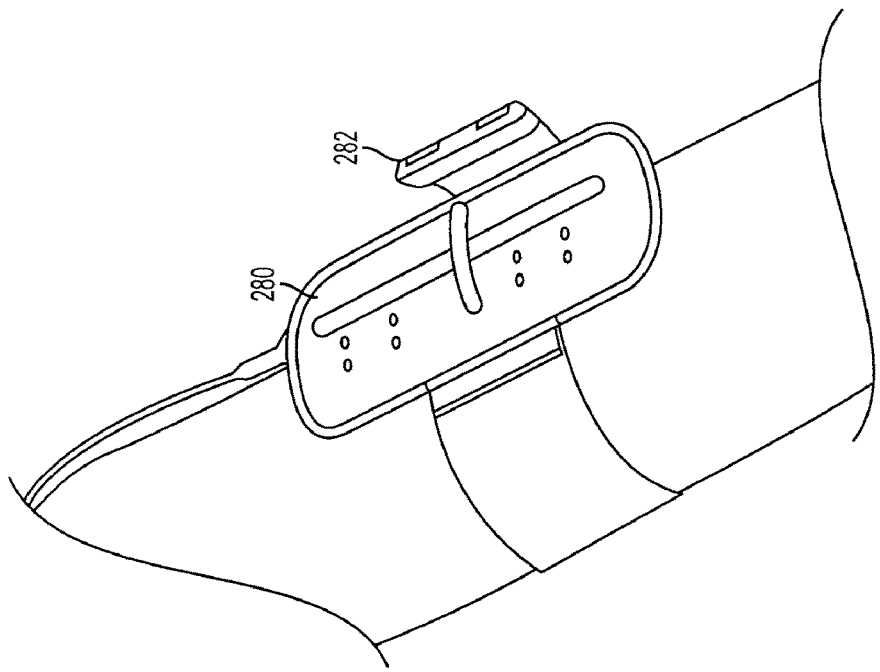
Figure 2D:
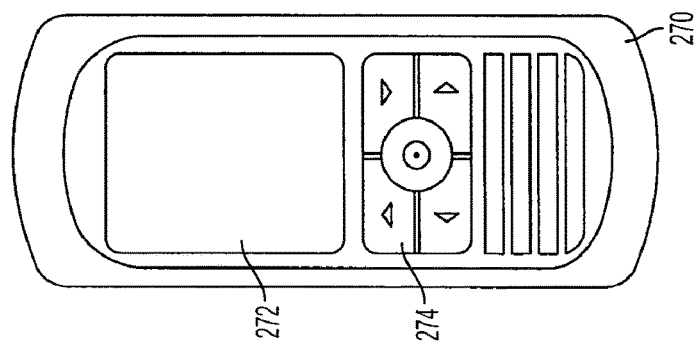

FIGS. 2D-F are diagrams of additional example portable electronic processing devices that have a sports operating mode according to embodiments of the present invention.

Figure 3A:
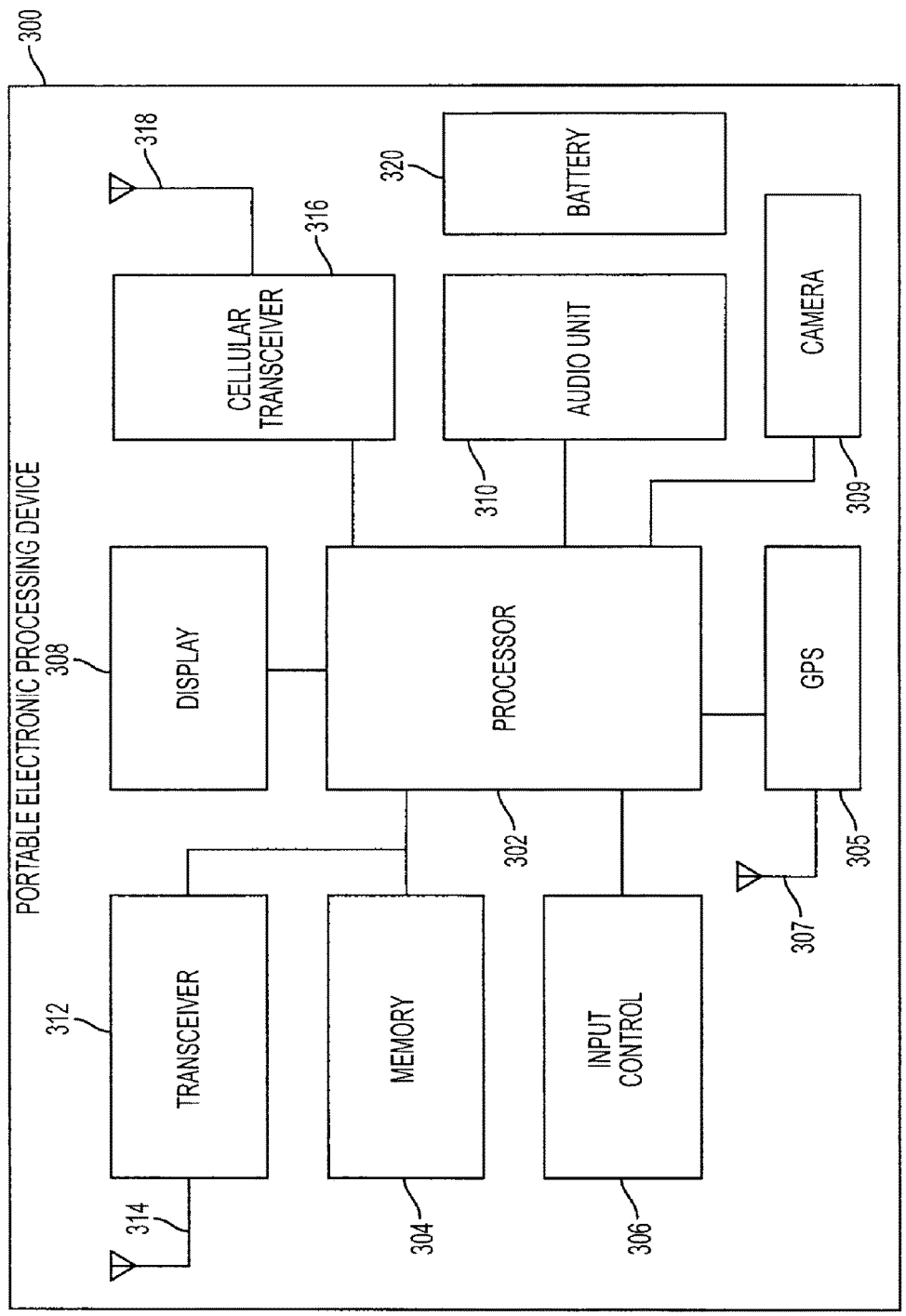

FIG. 3A is a more detailed diagram of a first example portable electronic processing device according to an embodiment of the present invention.

Figure 3B:
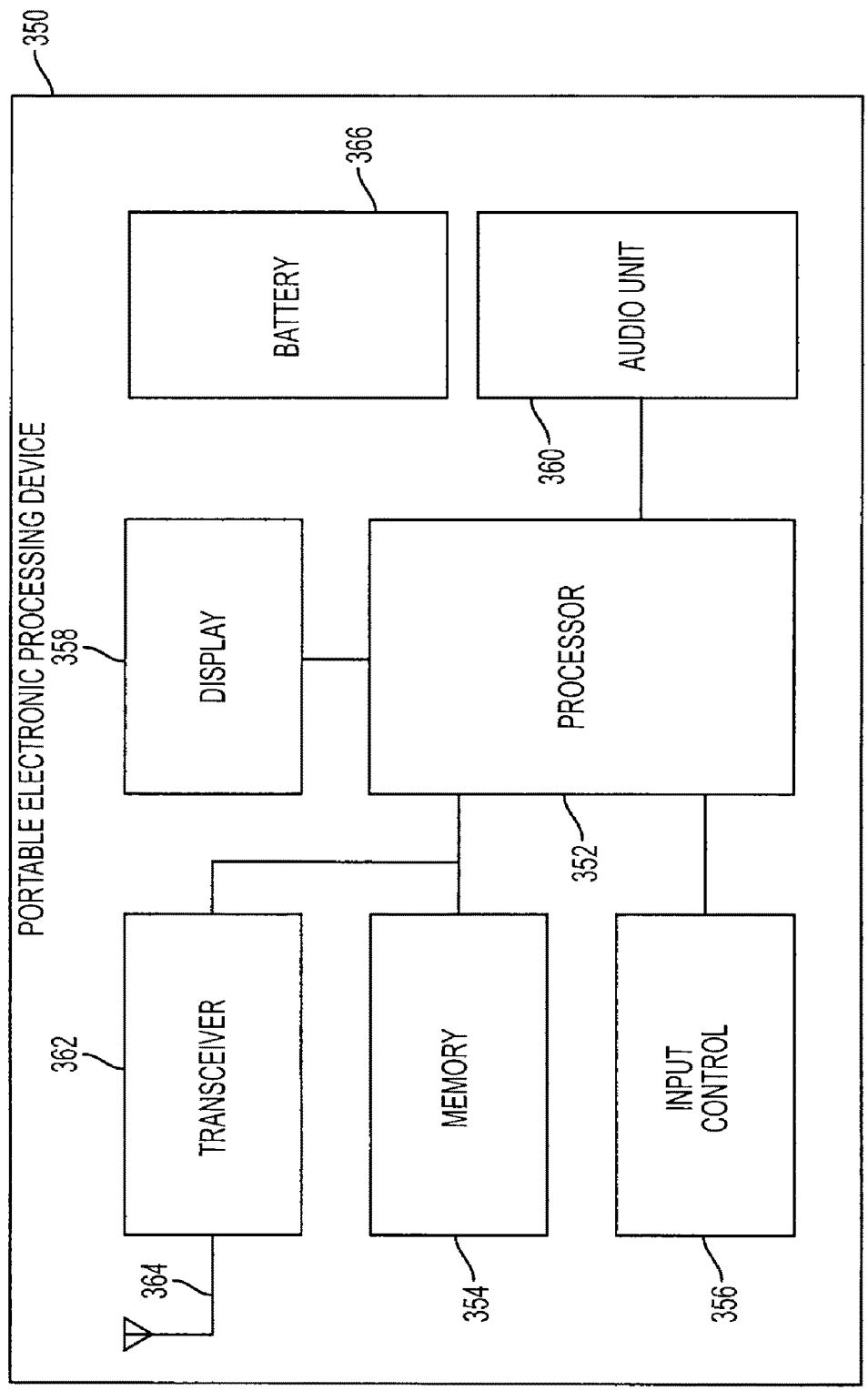

FIG. 3B is a more detailed diagram of a second example portable electronic processing device according to an embodiment of the present invention.

Figure 4A:
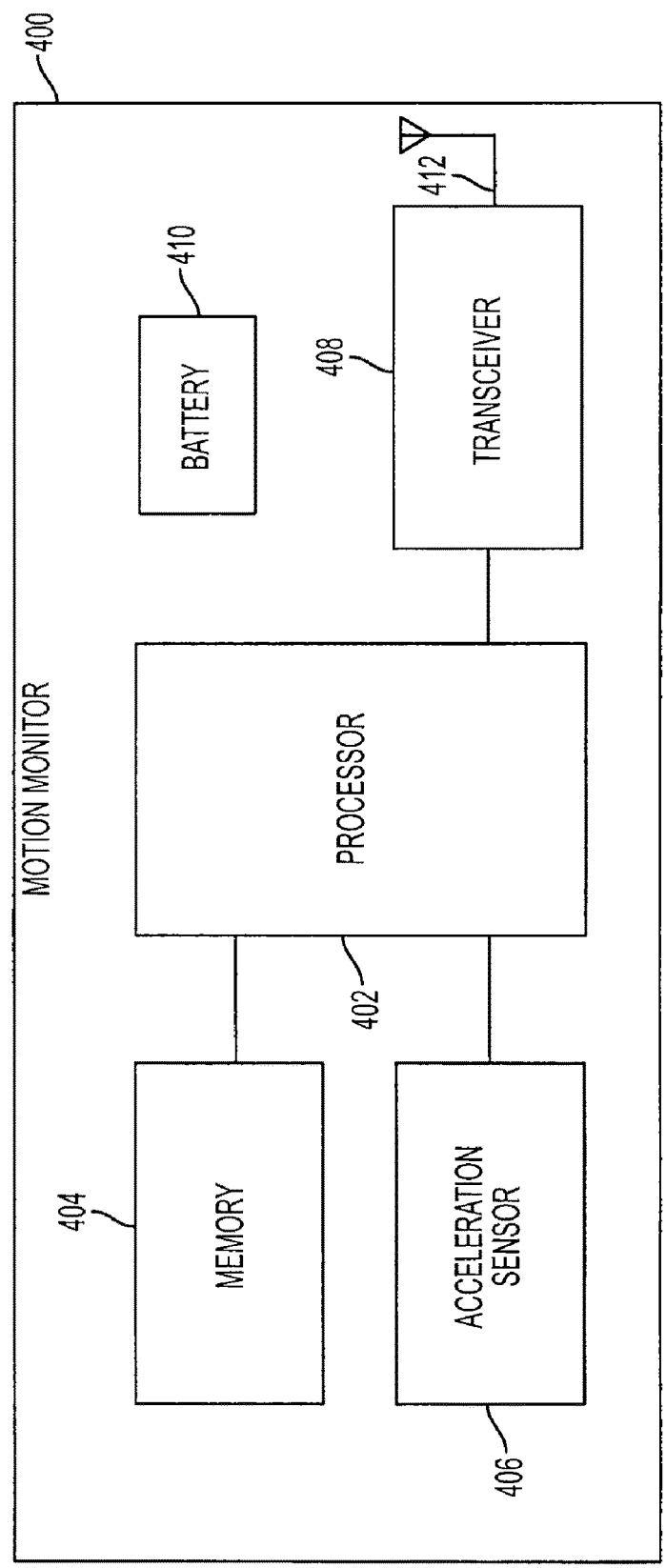

FIG. 4A is a diagram of an example motion monitor according to an embodiment of the present invention.

Figure 4B:
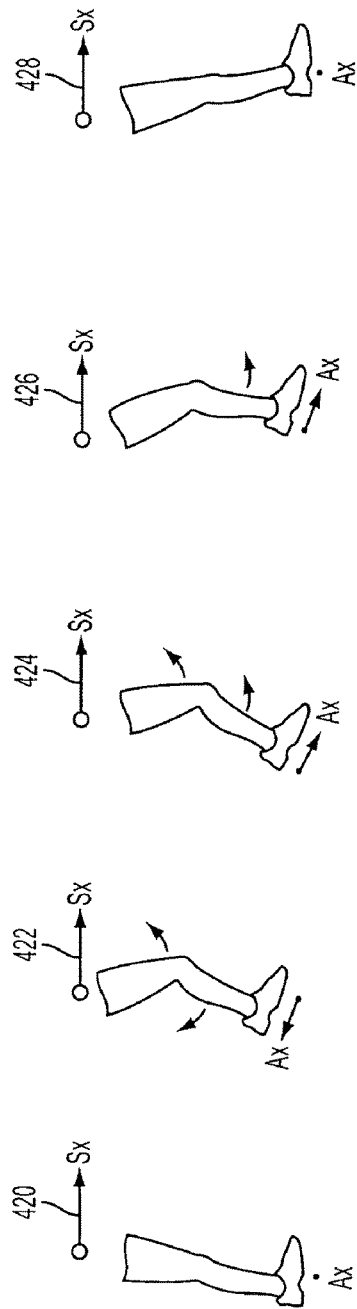

FIG. 4B is a diagram that illustrates how the motion monitor of FIG. 4A operates.

Figure 4C:
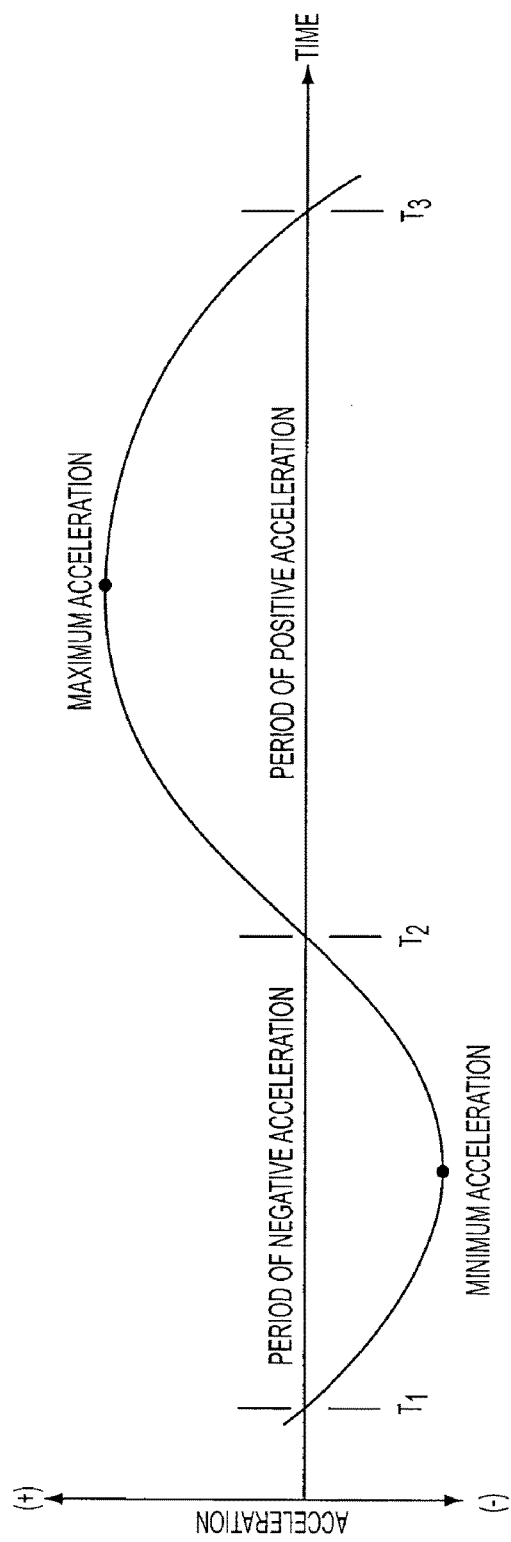

FIG. 4C is a diagram that illustrates how the motion monitor of FIG. 4A operates.

Figure 5:
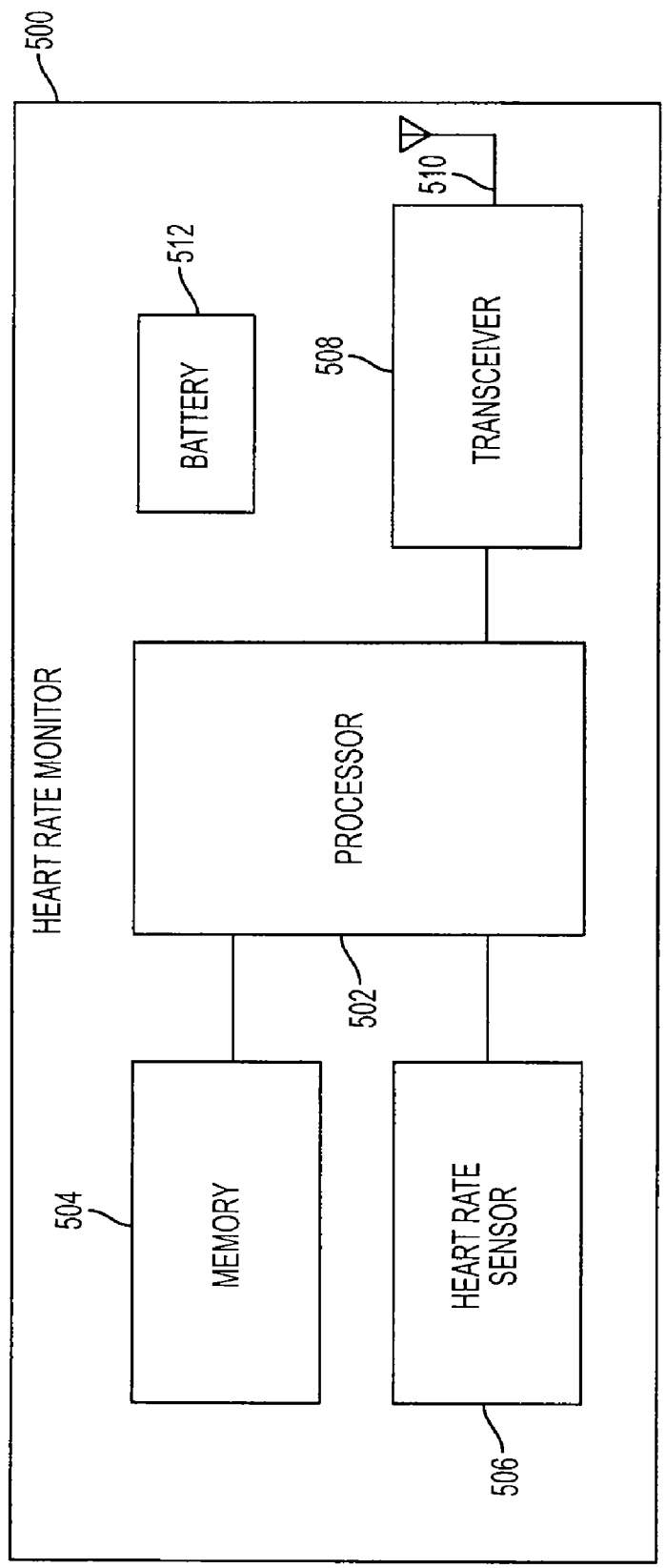

FIG. 5 is a diagram of an example heart rate monitor according to an embodiment of the present invention.

Figure 6A:
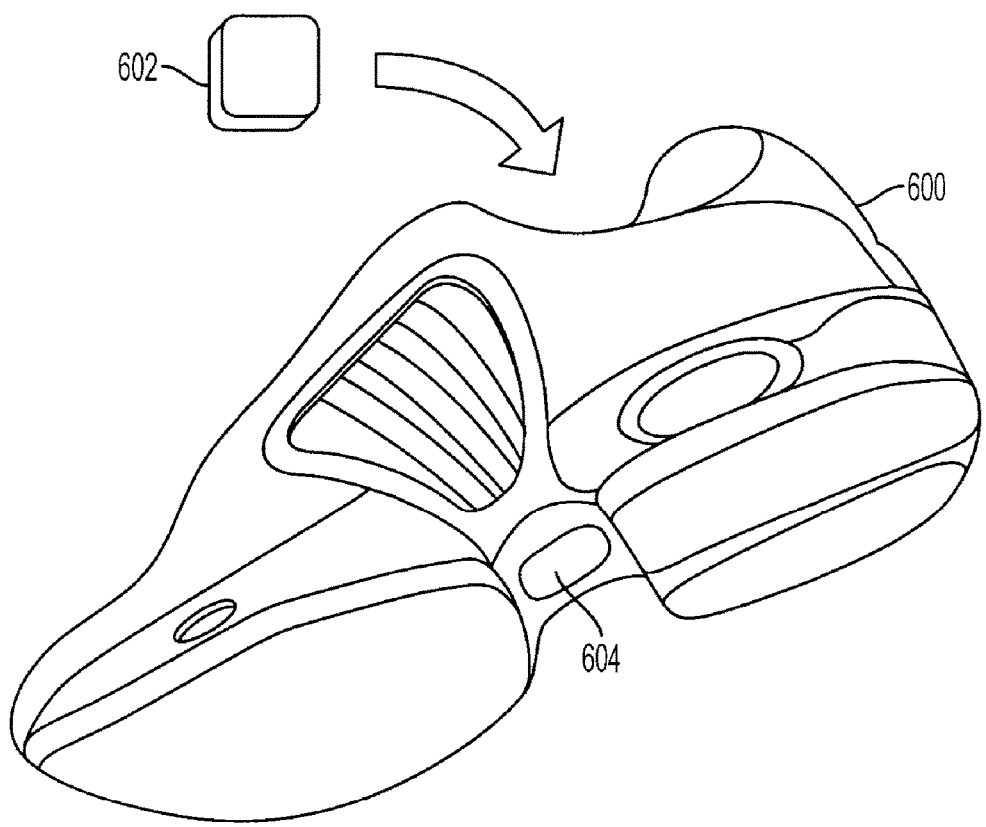

FIG. 6A is a diagram of a shoe having a motion monitor inserted into a recess in the sole of the shoe according to an embodiment of the present invention.

Figure 6B:
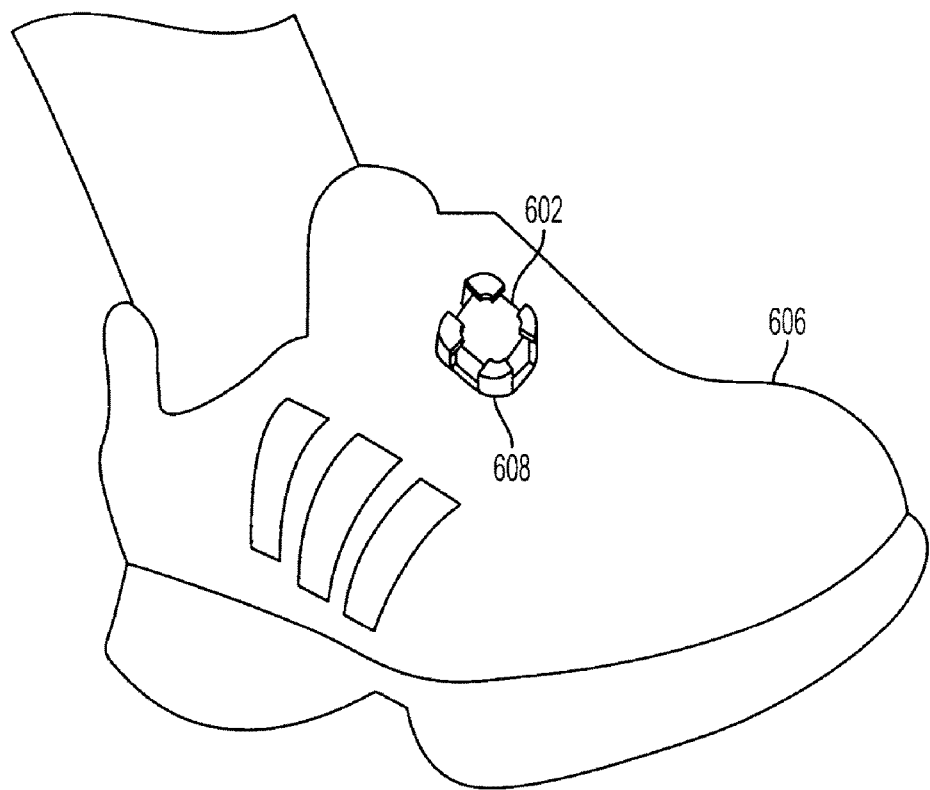

FIG. 6B is a diagram of a shoe having a motion monitor mounted on an external portion of the shoe.

FIG. 6C is a diagram of an example motion monitor according to an embodiment of the present invention.

Figure 6D:
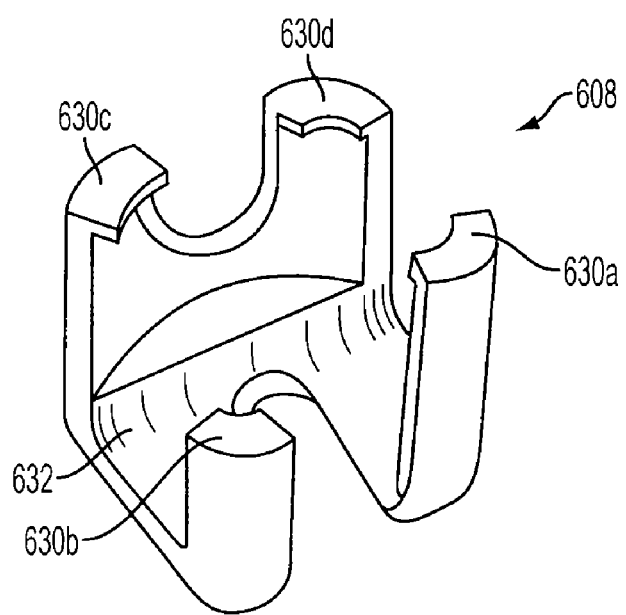

FIG. 6D is a diagram of an example mounting device for a motion monitor according to an embodiment of the present invention.

FIG. 6E is a diagram of a motion monitor that has an example winged-battery cap for mounting the motion monitor on a shoe according to an embodiment of the present invention.

FIG. 6F is a diagram that shows the motion monitor of FIG. 6E mounted on a shoe according to an embodiment of the present invention.

Figure 6G:
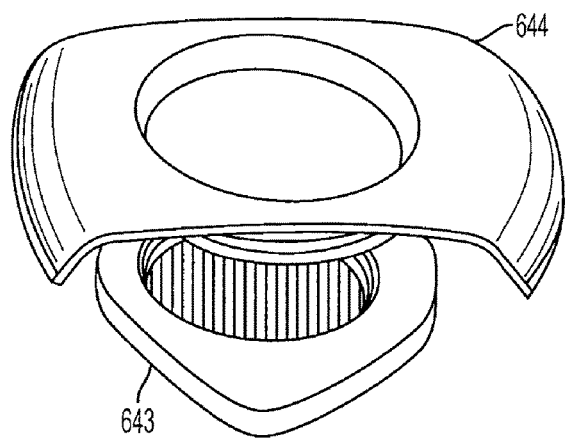

FIG. 6G is a diagram of a motion monitor that has a second example winged-battery cap for mounting the motion monitor on a shoe according to an embodiment of the present invention.

Figure 6H:
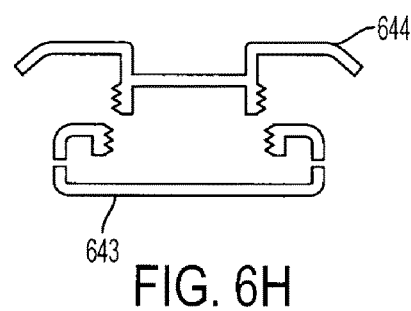

FIG. 6H is a diagram that further illustrates the motion monitor and wing-battery cap of FIG. 6G.

Figure 6I:
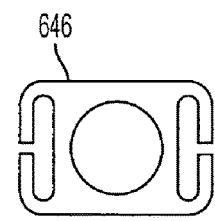

FIG. 6I is a diagram of a third example winged-battery cap for a motion monitor according to an embodiment of the present invention.

Figure 6J:
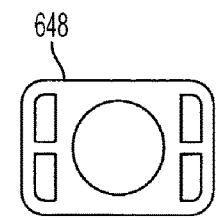

FIG. 6J is a diagram of a fourth example winged-battery cap for a motion monitor according to an embodiment of the present invention.

Figure 7:
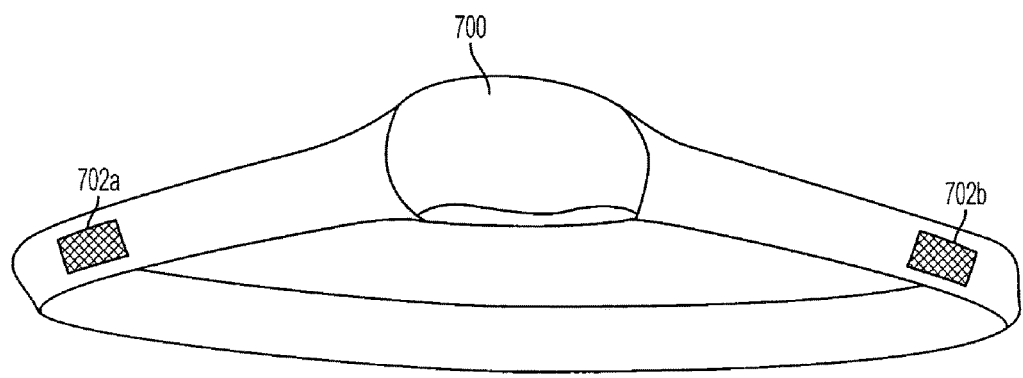

FIG. 7 is a diagram of a heart rate monitor with built in sensors for determining percent body fat according to an embodiment of the present invention.

Figure 8:
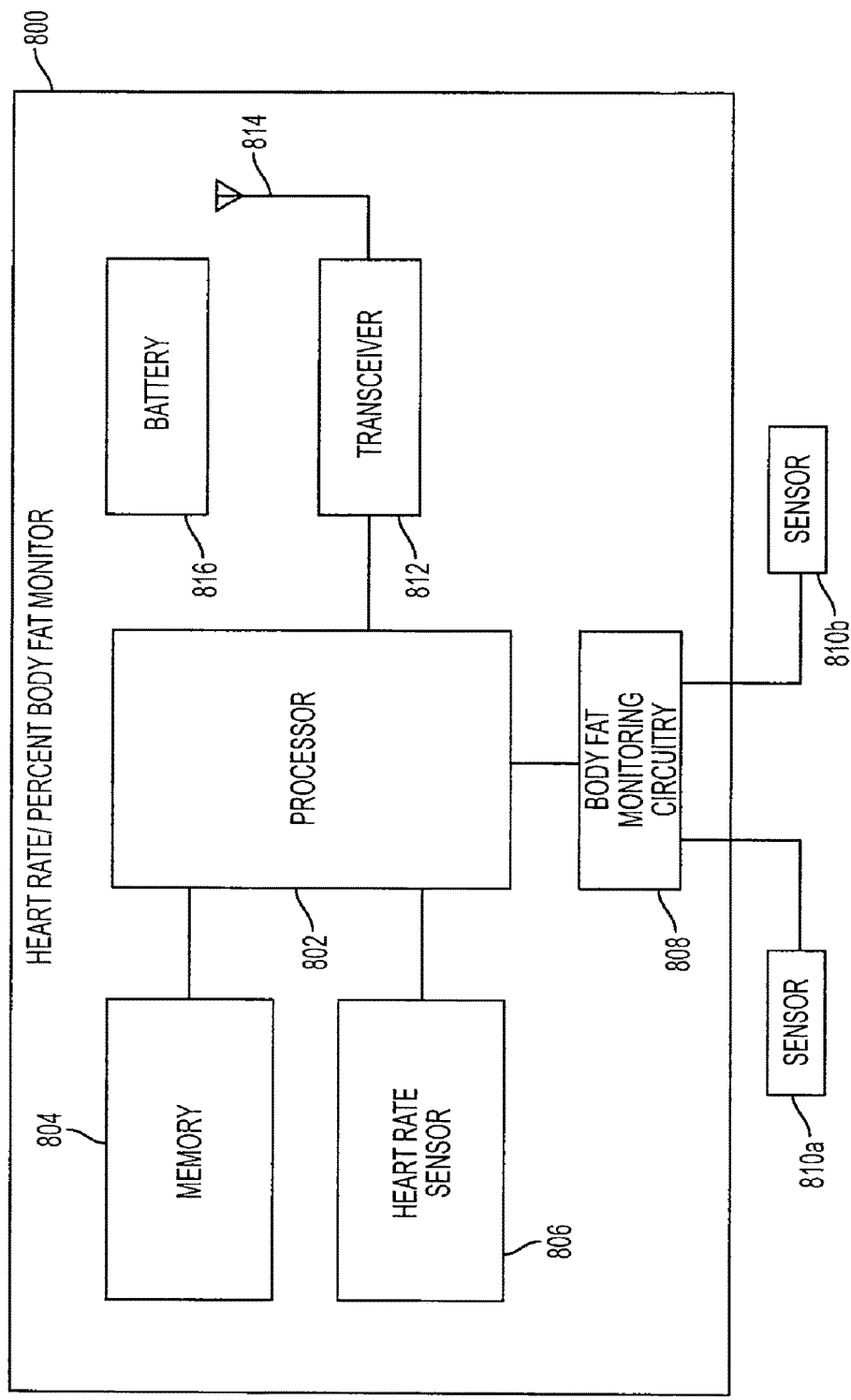

FIG. 8 is a diagram of a heart rate/percent body fat monitor according to an embodiment of the present invention.

Figure 9:
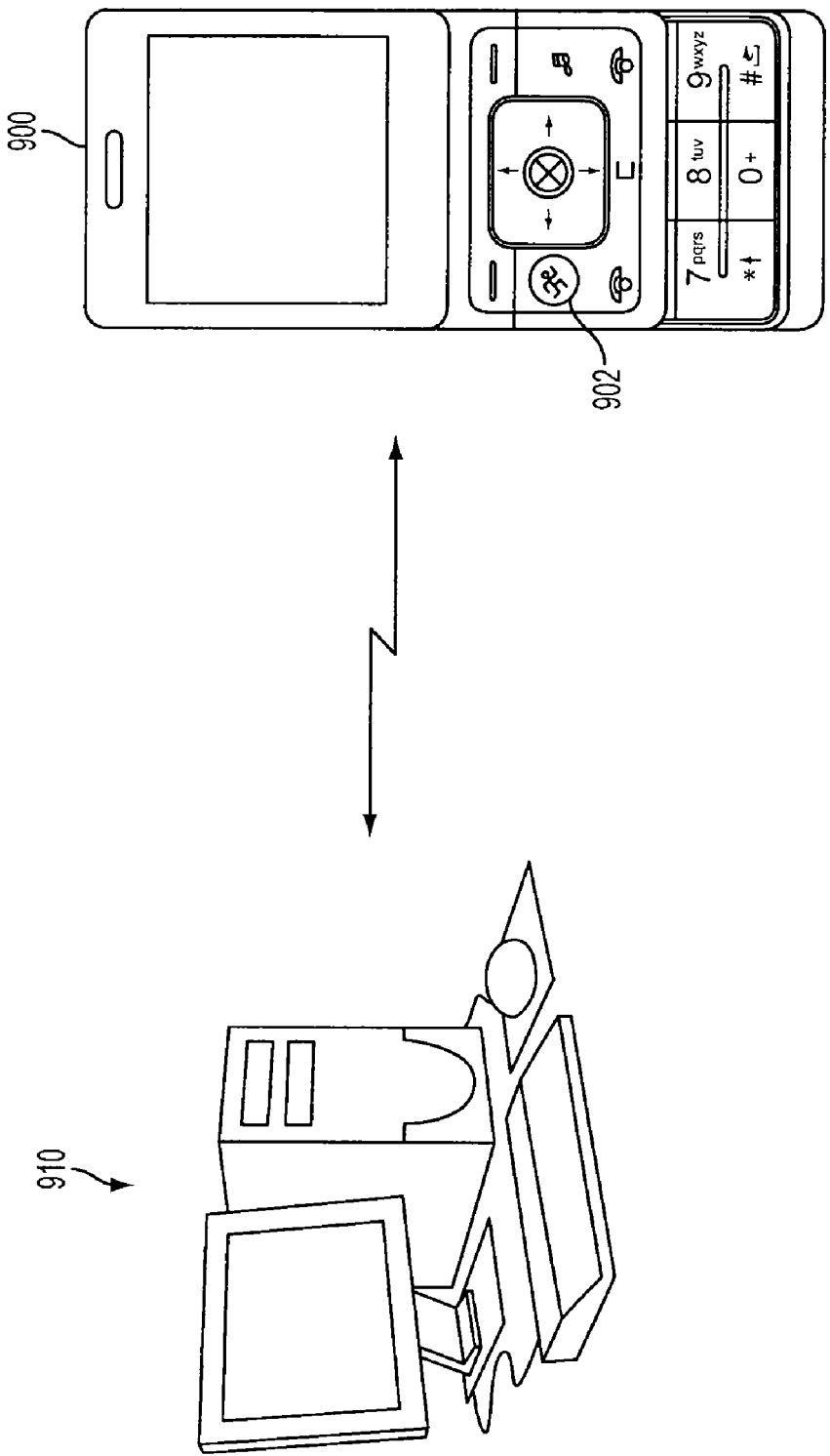

FIG. 9 is a diagram of a first portable electronic processing device interacting with a computer according to an embodiment of the present invention.

Figure 10:
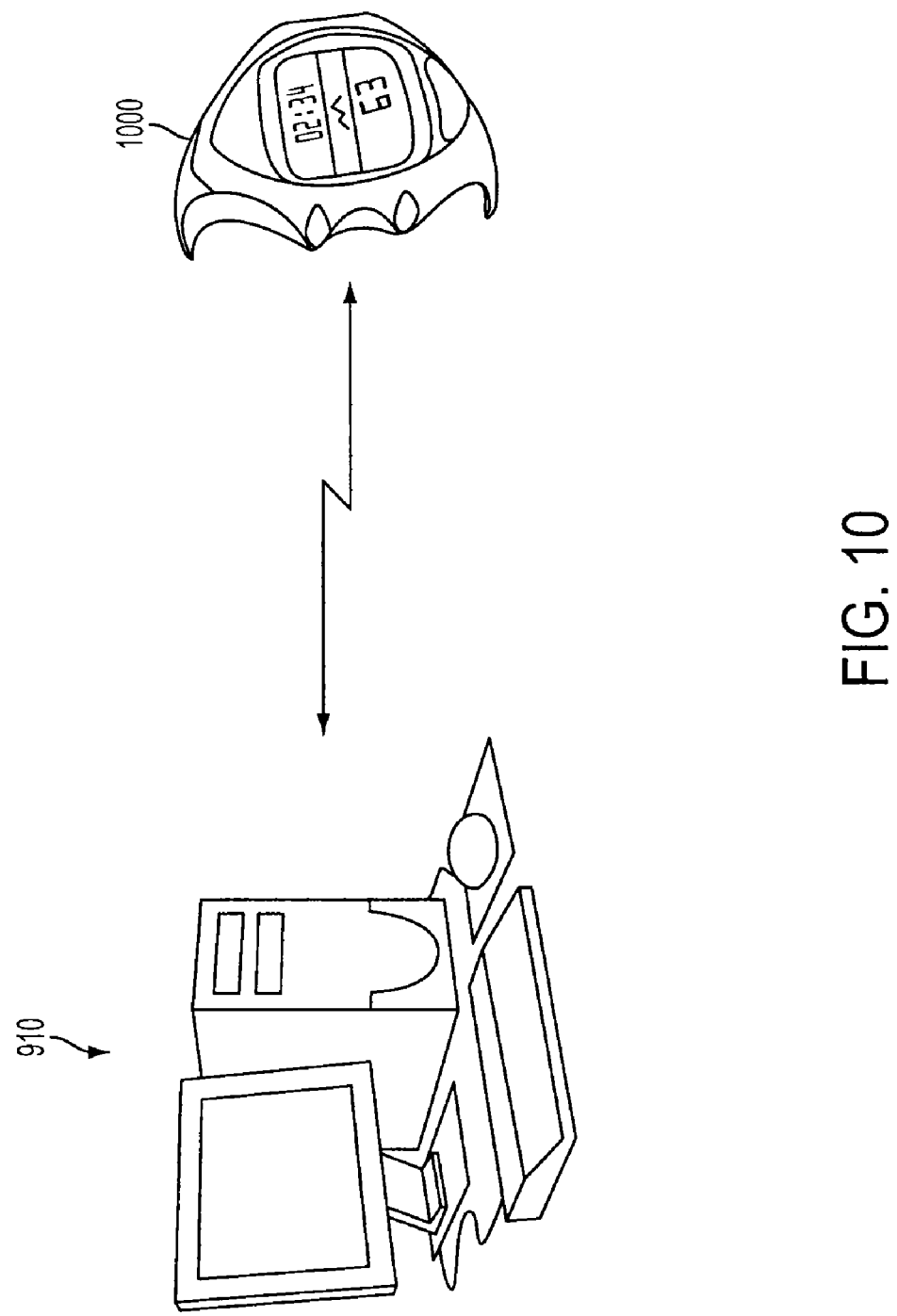

FIG. 10 is a diagram of a second portable electronic processing device interacting with a computer according to an embodiment of the present invention.

FIG. 11A is a diagram of a first portable electronic processing device interacting with a computer and a web server according to an embodiment of the present invention.

Figure 11B:
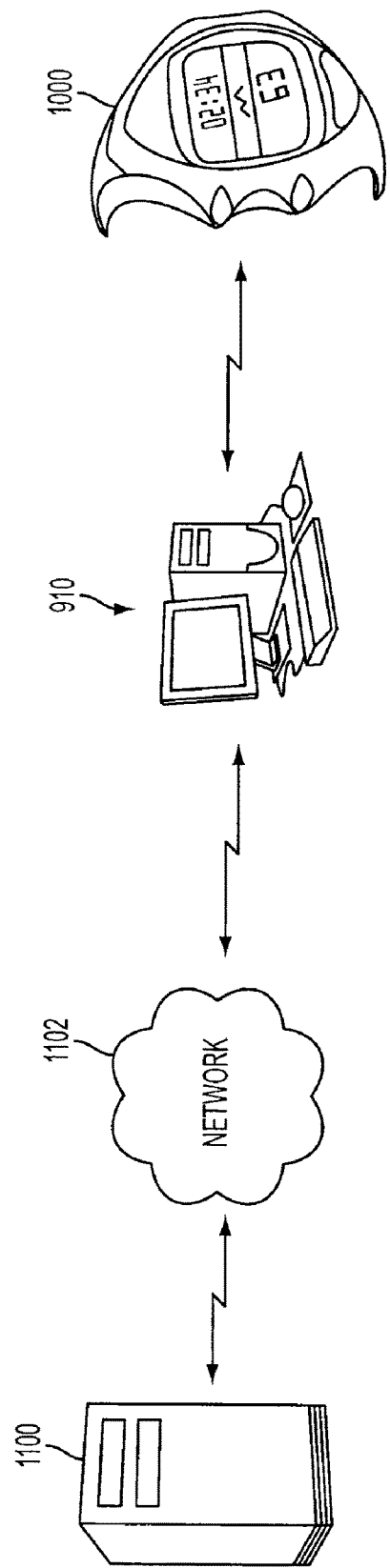

FIG. 11B is a diagram of a second portable electronic processing device interacting with a computer and a web server according to an embodiment of the present invention.

Figure 12:
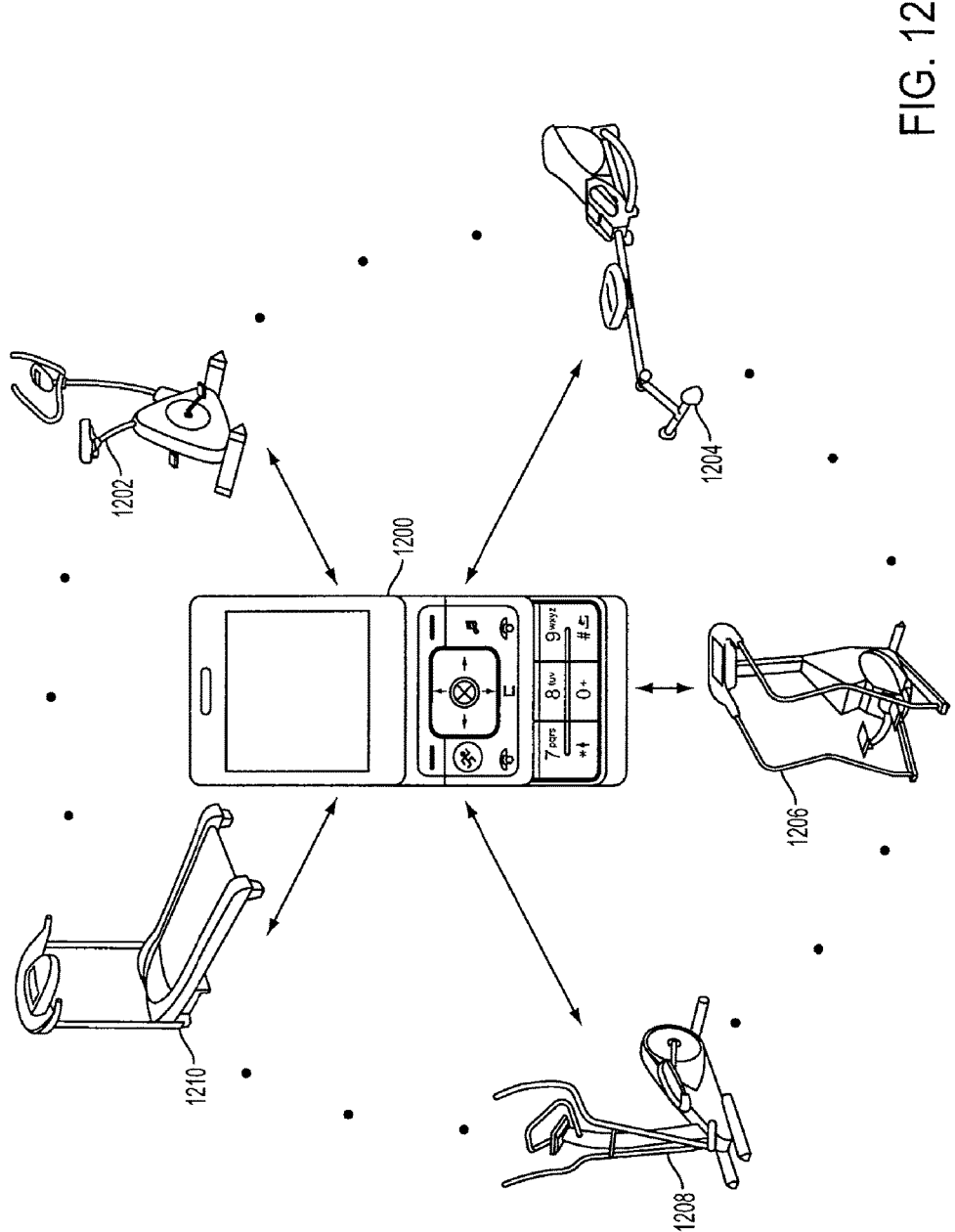

FIG. 12 is a diagram of an example portable electronic processing device interacting with exercise machines according to an embodiment of the present invention.

Figure 13:
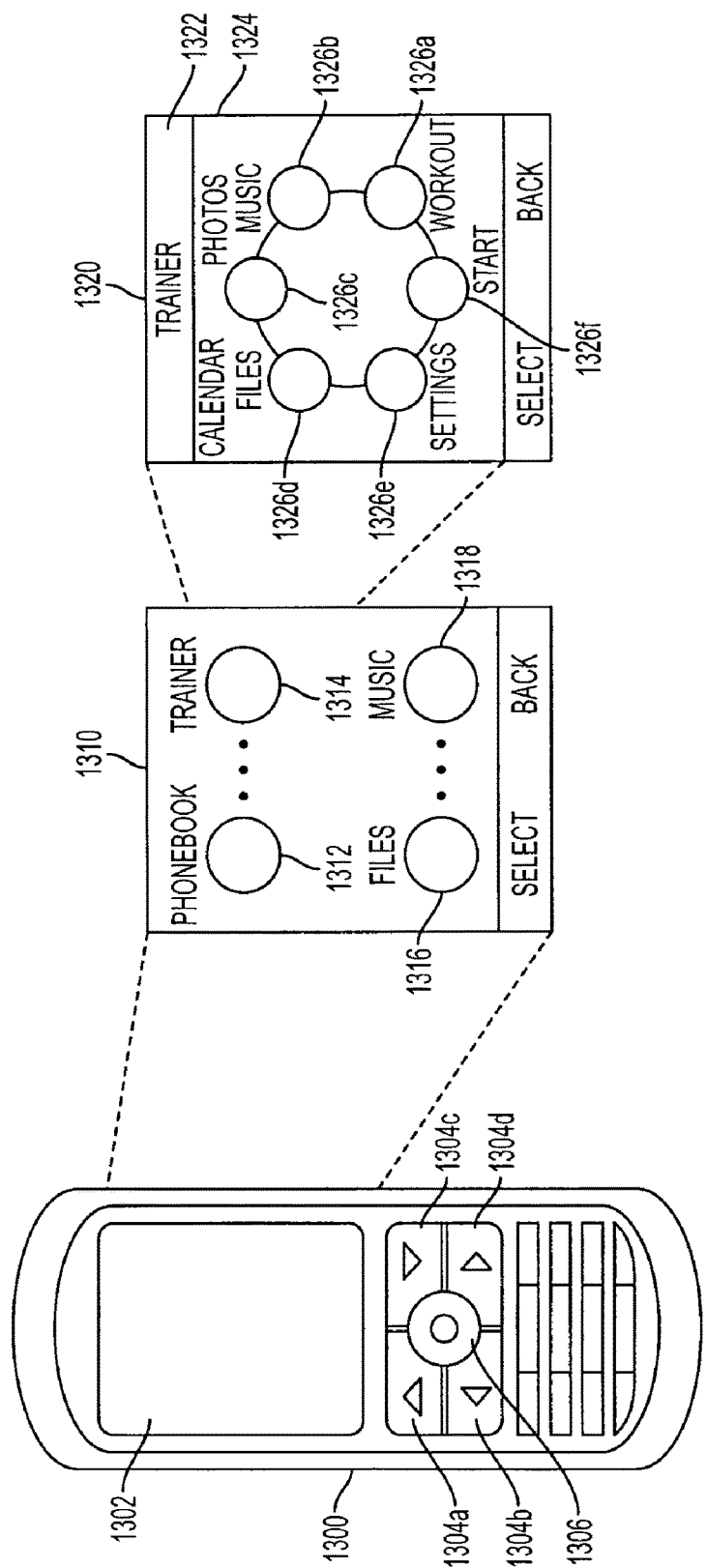

FIG. 13 is a diagram of an example portable electronic processing device that includes virtual trainer functionality according to an embodiment of the present invention.

Figure 14A:
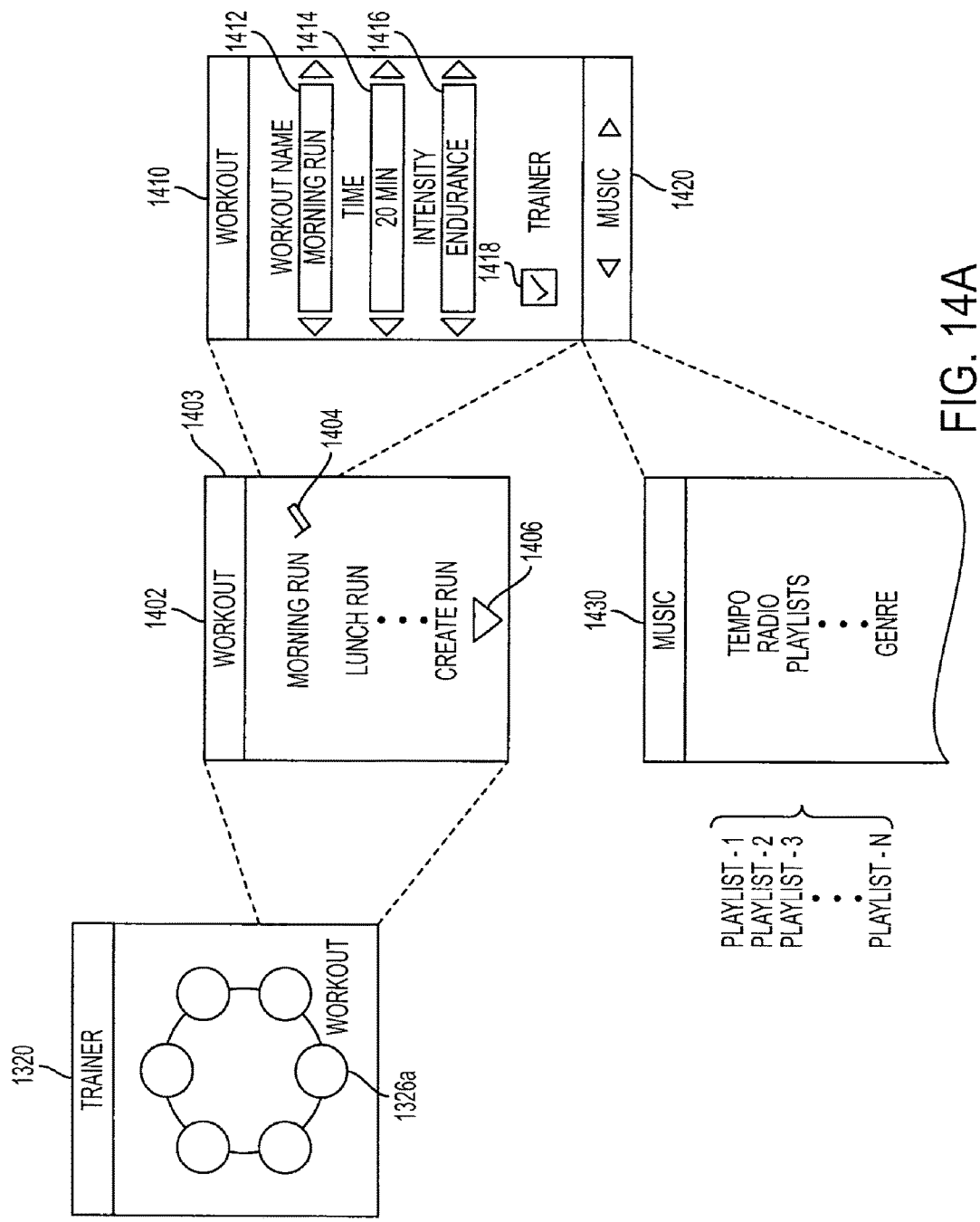

FIG. 14A is a diagram that illustrates workout features of a sports electronic training system according to an embodiment of the present invention.

FIGS. 14B and 14C are a table that illustrates example feedback provided by a sport training system according to an embodiment of the present invention.

Figure 15A:
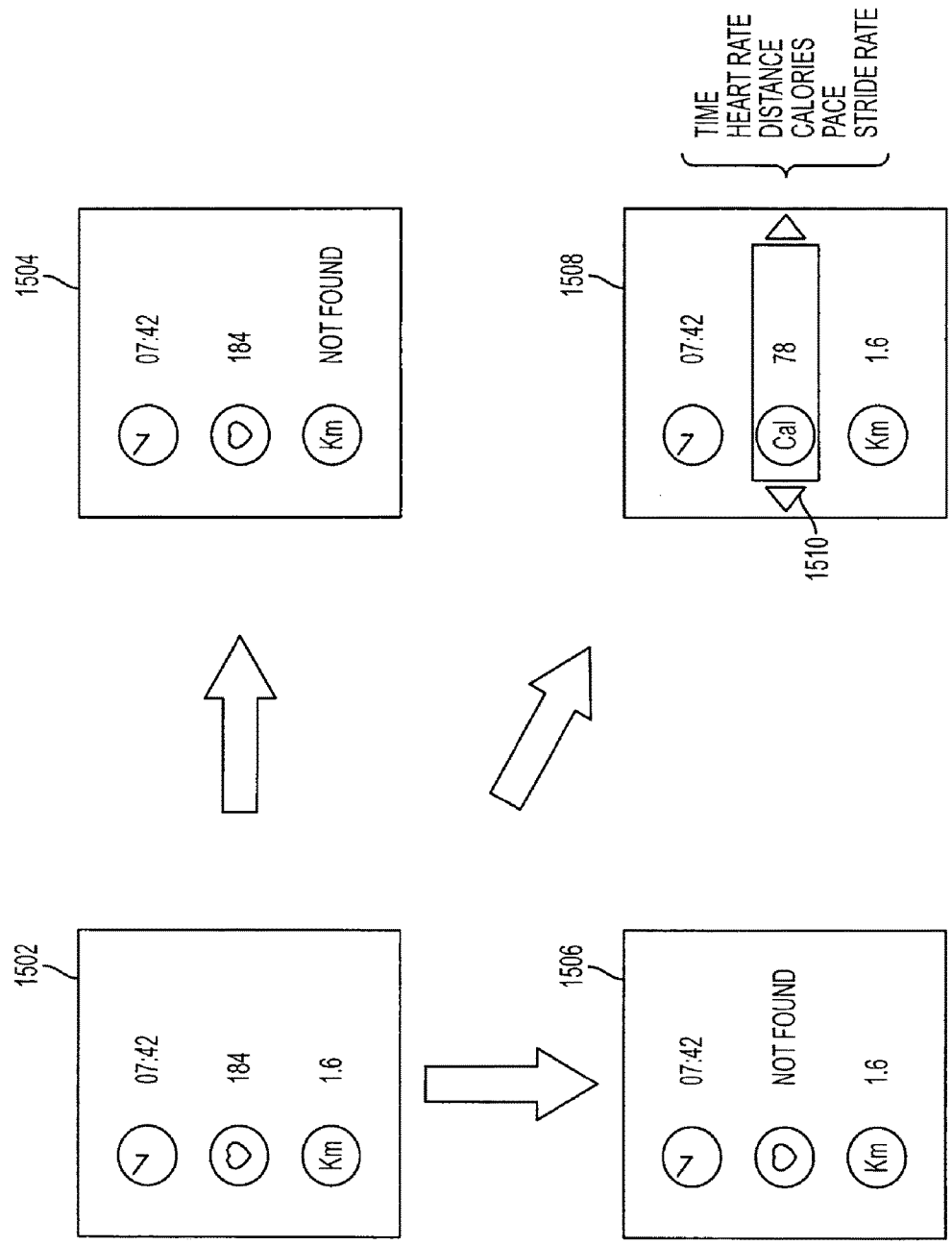

FIG. 15A is a diagram that illustrates example customizable parameter displays for a sports electronic training system according to an embodiments of the present invention.

Figure 15B:
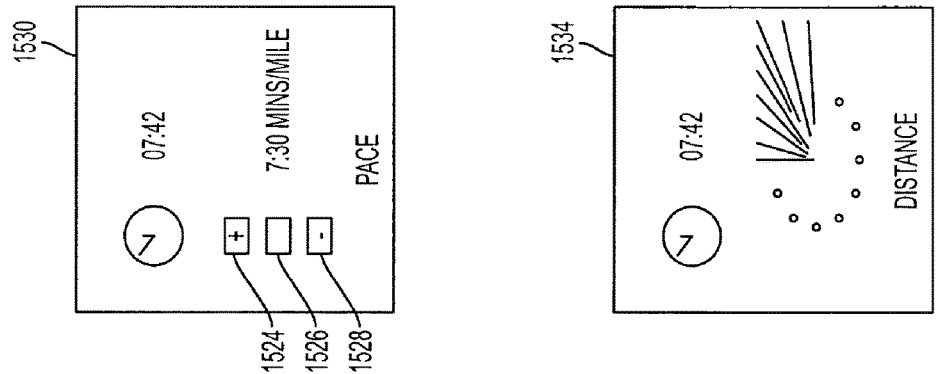
Figure 15B:
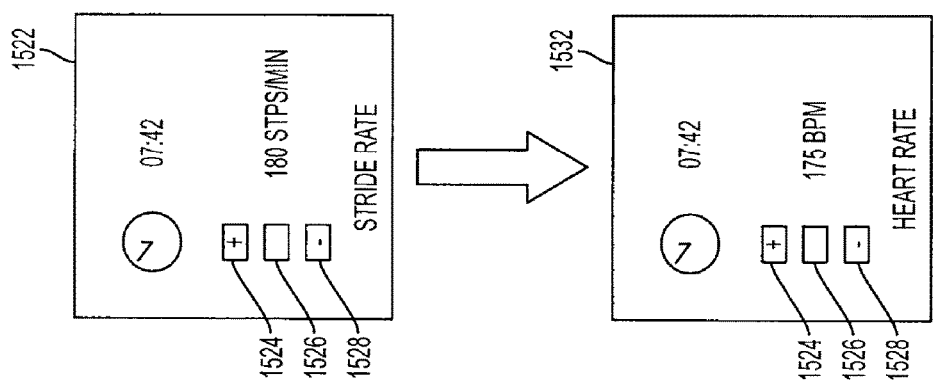

FIG. 15B is a diagram that illustrates example customizable parameter displays for a sports electronic training system according to an embodiment of the present invention.

Figure 15C:
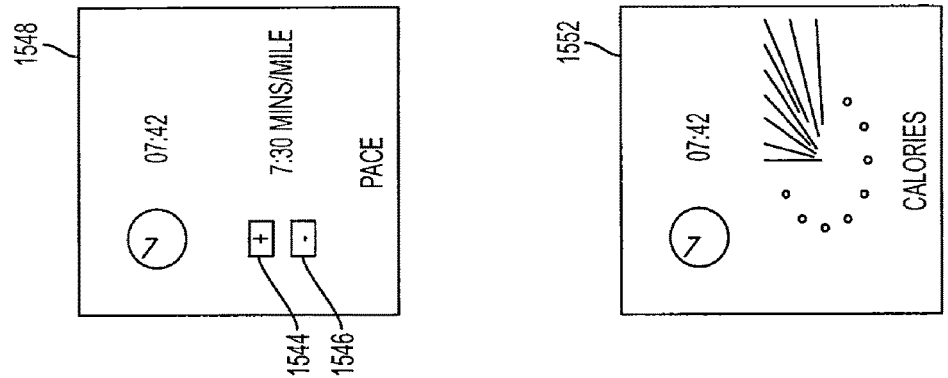
Figure 15C:
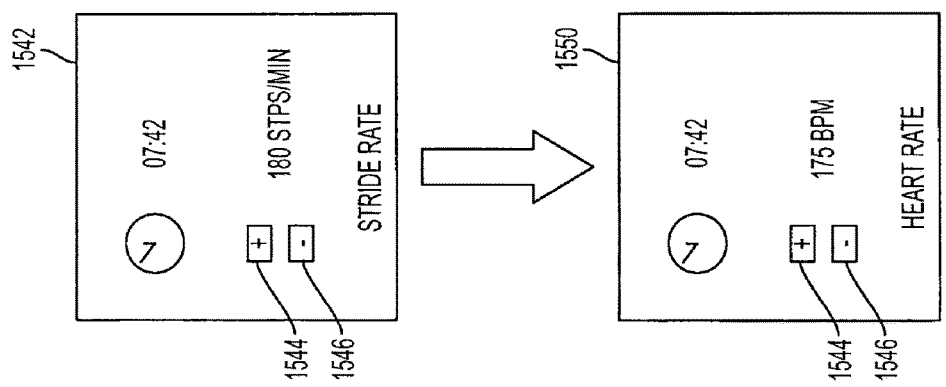

FIG. 15C is a diagram that illustrates example customizable parameter displays for a sports electronic training system according to an embodiment of the present invention.

Figure 15D:
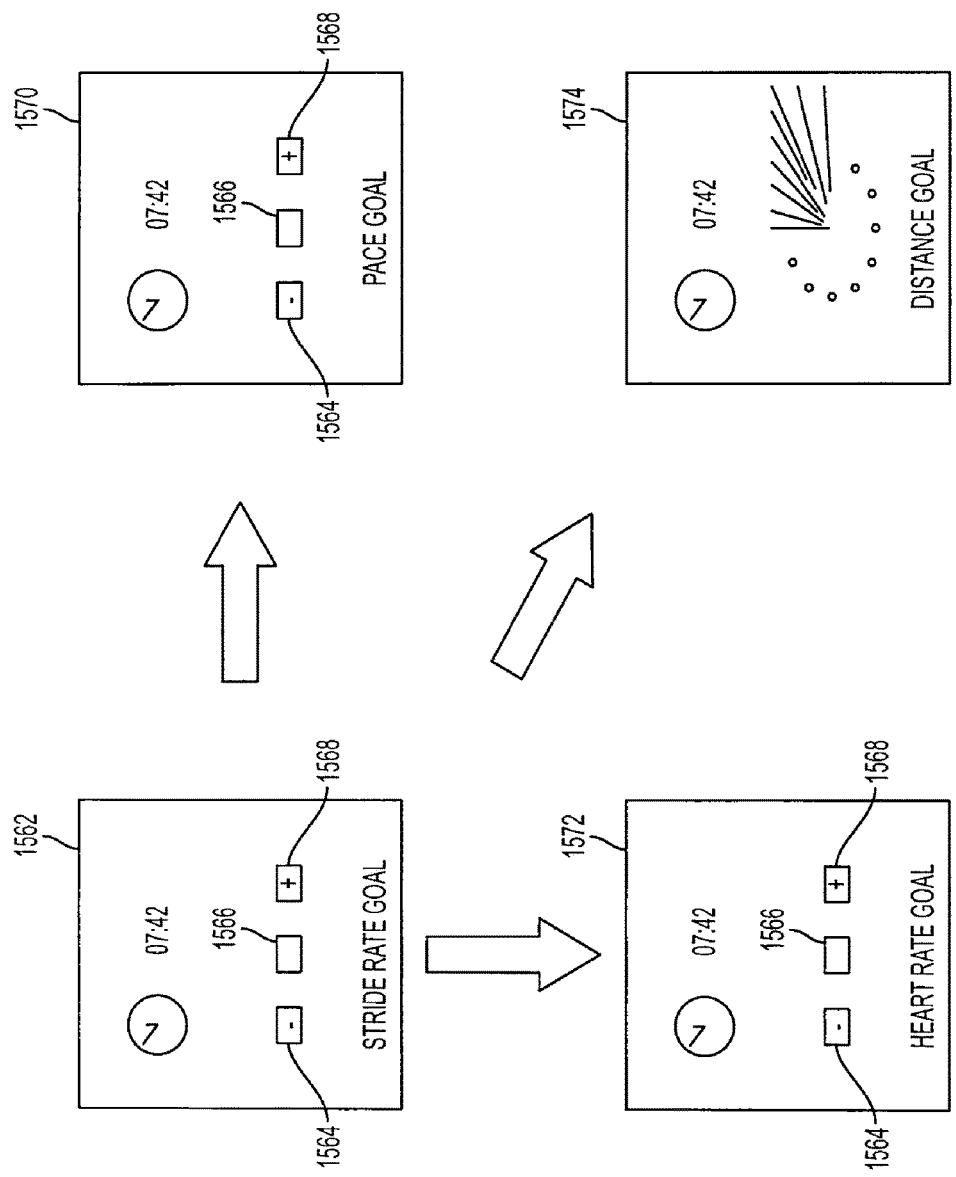

FIG. 15D is a diagram that illustrates example customizable parameter displays for a sports electronic training system according to an embodiment of the present invention.

FIG. 15E is a table that illustrates an example of how to calculate calories burned while exercising according to embodiments of the present invention.

FIG. 15F is a table that illustrates an example of how to calculate calories burned while exercising according to embodiments of the present invention.

FIG. 15G is a table that illustrates an example of how to calculate calories burned while exercising according to embodiments of the present invention.

Figure 16:
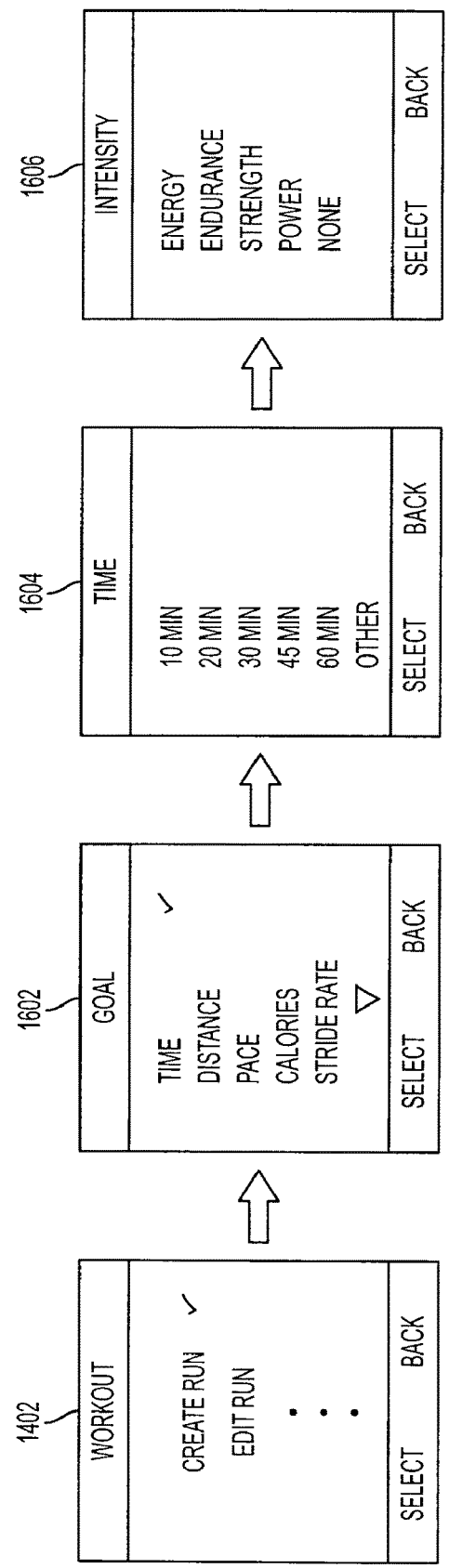

FIG. 16 is a diagram that illustrates a method for creating a workout using a sports electronic training system according to an embodiment of the present invention.

Figure 17:
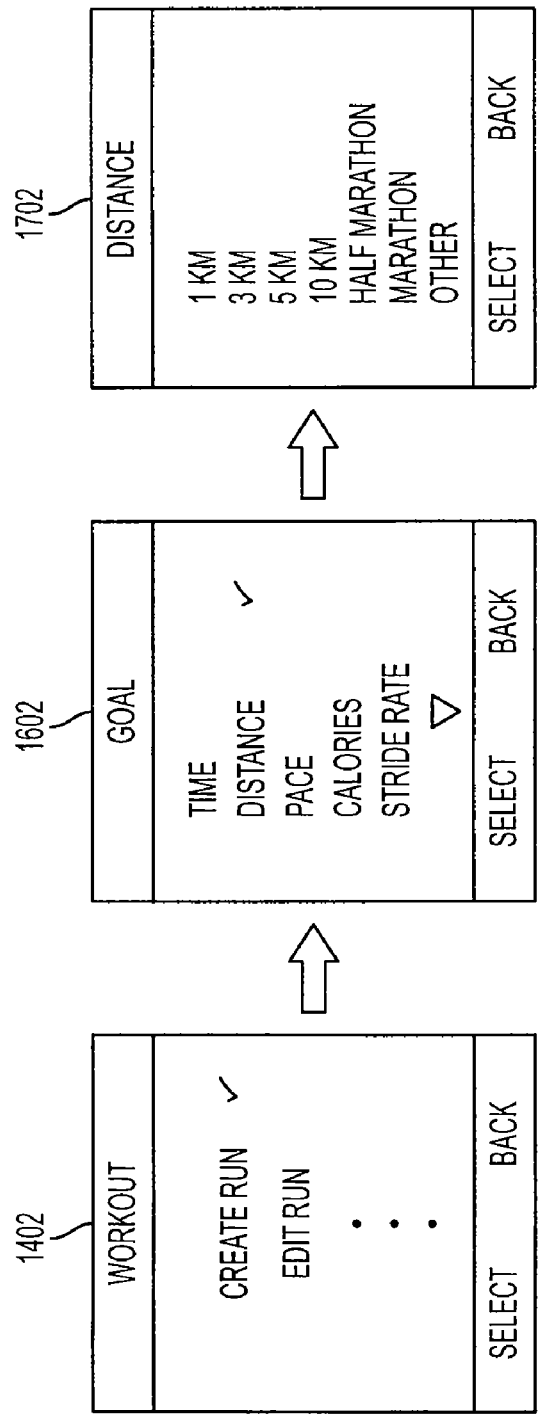

FIG. 17 is a diagram that illustrates a method for creating a workout using a sports electronic training system according to an embodiment of the present invention.

Figure 18:
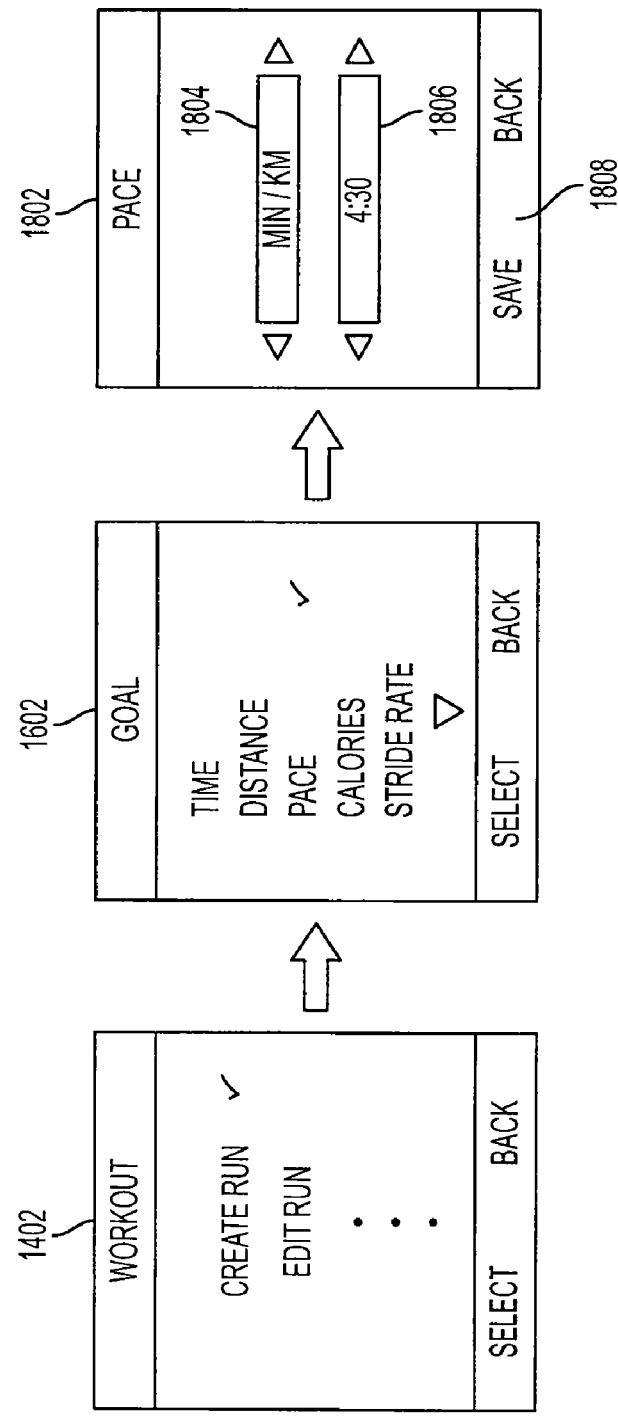

FIG. 18 is a diagram that illustrates a method for creating a workout using a sports electronic training system according to an embodiment of the present invention.

Figure 19:
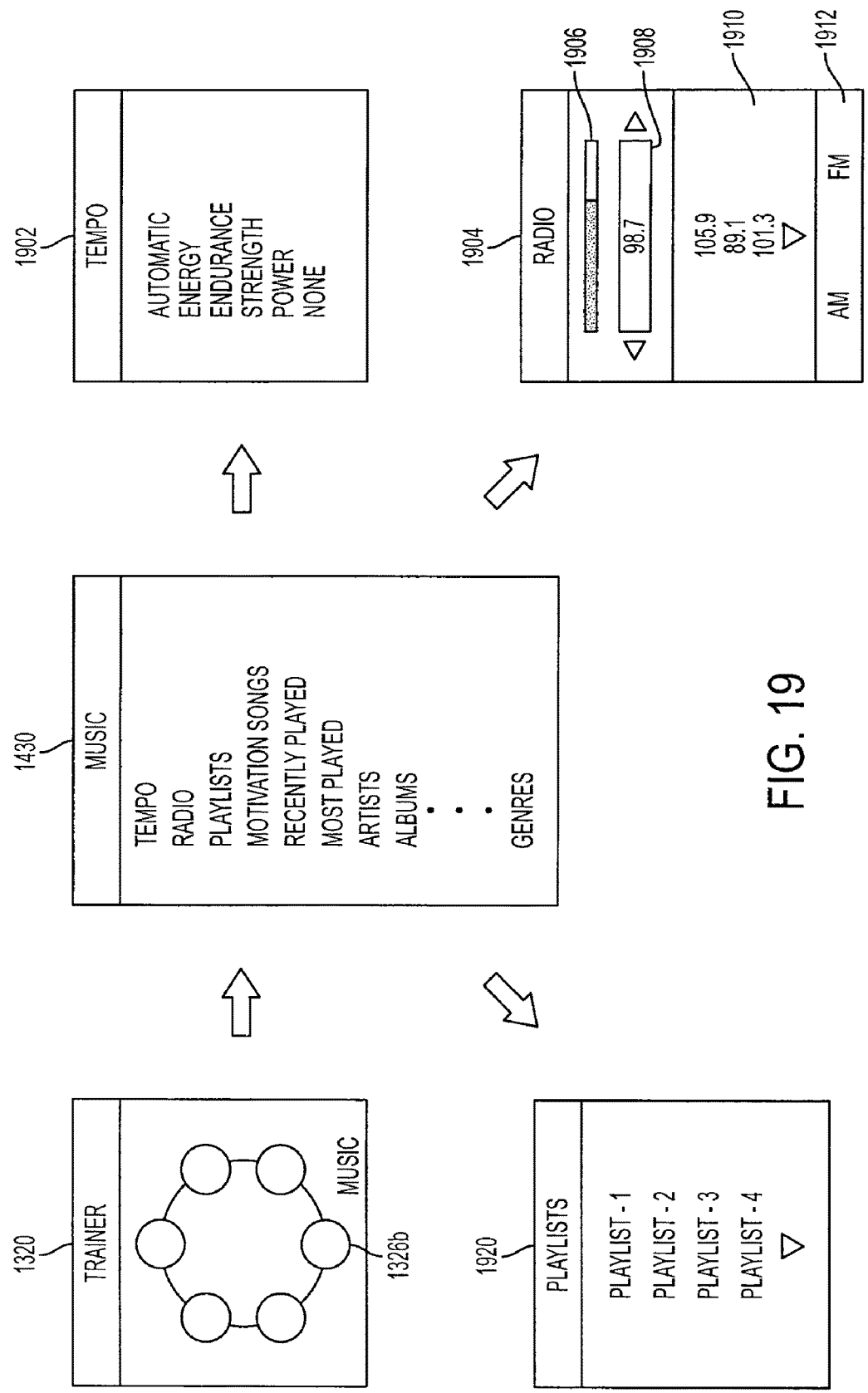

FIG. 19 is a diagram that illustrates music features of a sports electronic training system according to an embodiment of the present invention.

Figure 20:
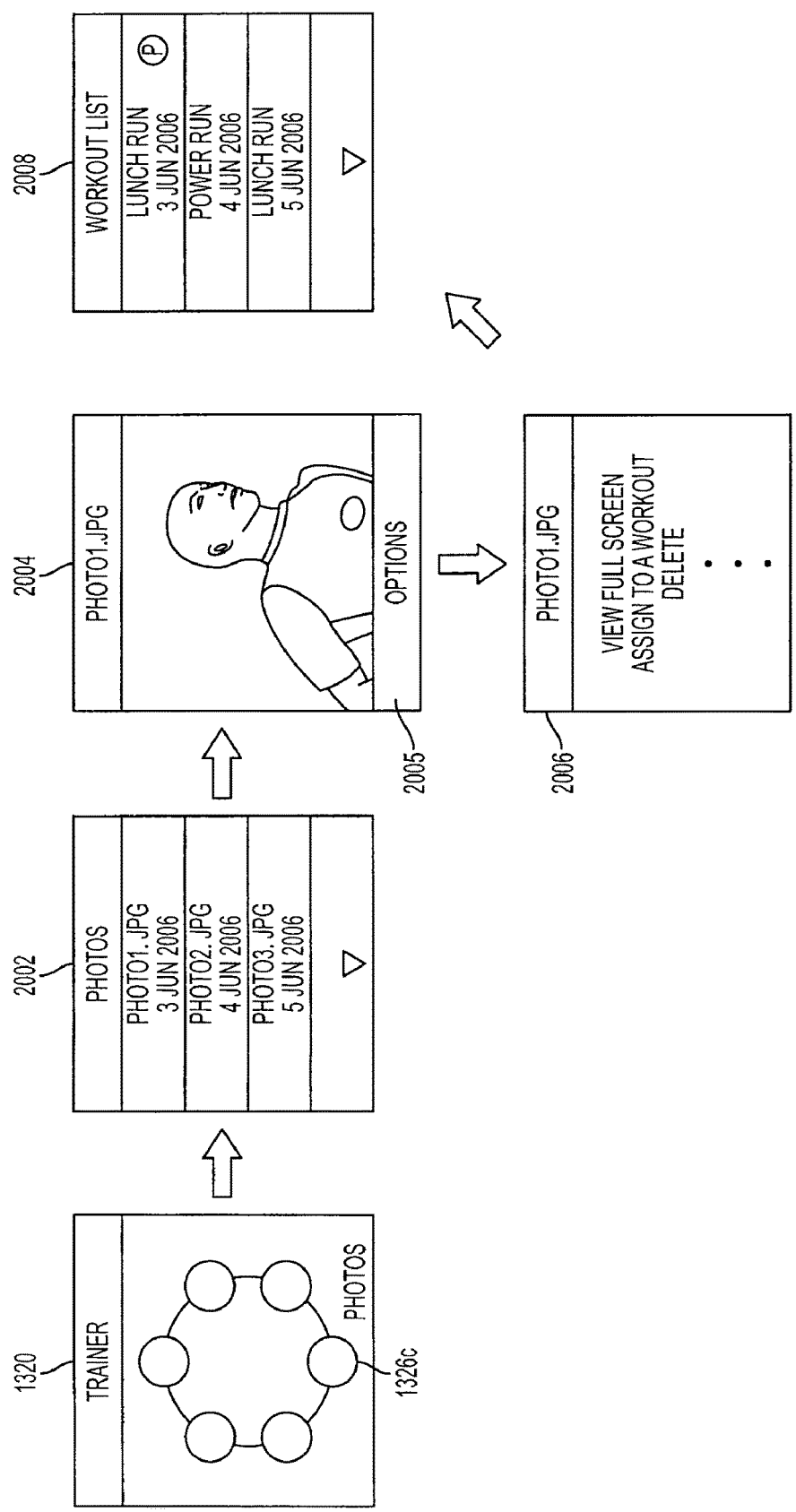

FIG. 20 is a diagram that illustrates photo features of a sports electronic training system according to an embodiment of the present invention.

Figure 21:
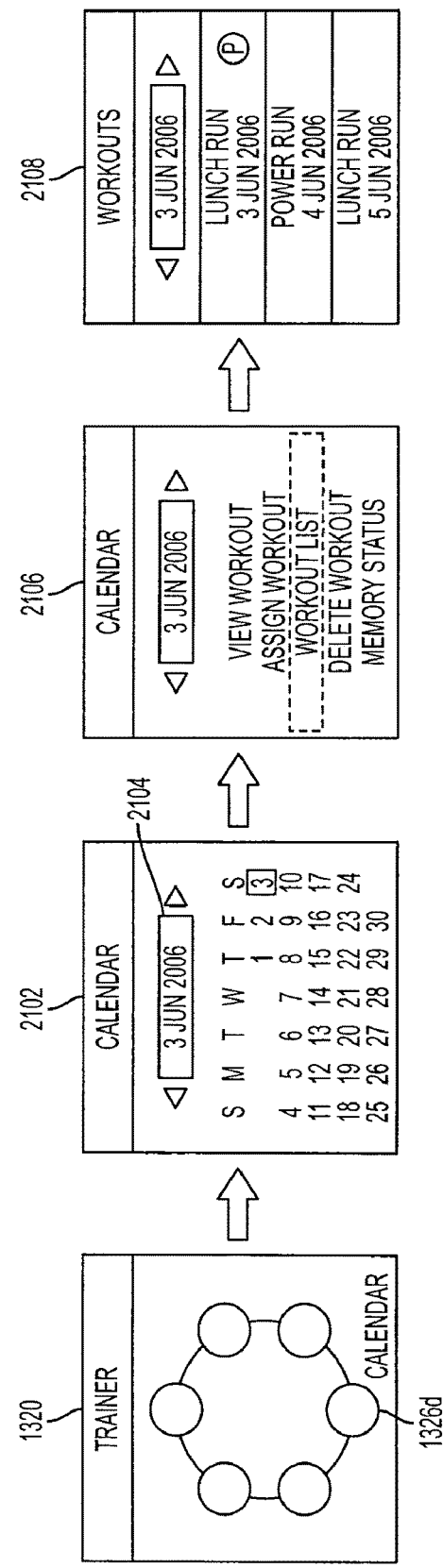

FIG. 21 is a diagram that illustrates calendar features of a sports electronic training system according to an embodiment of the present invention.

Figure 22:
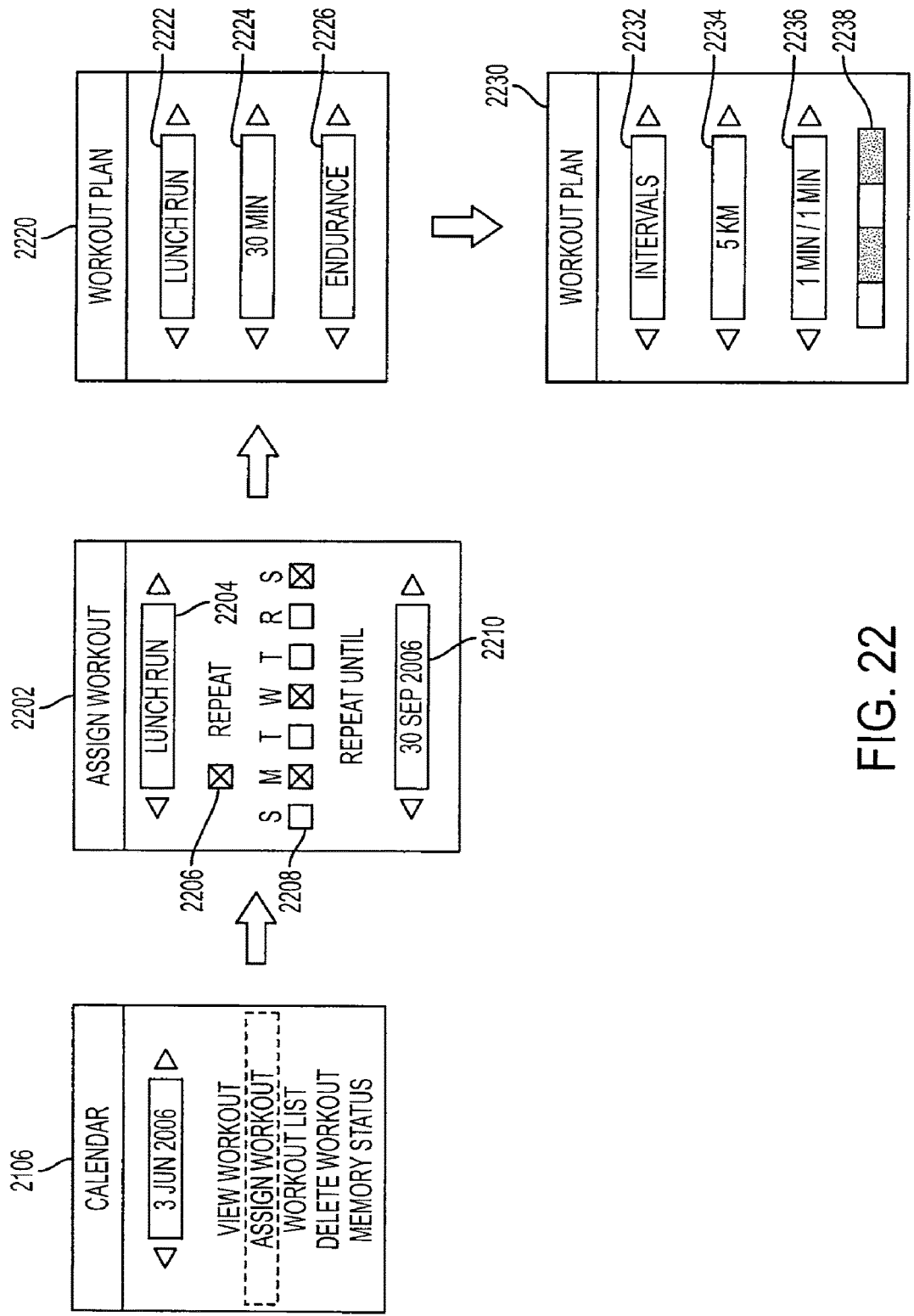

FIG. 22 is a diagram that illustrates an interaction between workout and calendar features of a sports electronic training system according to an embodiment of the present invention.

Figure 23:
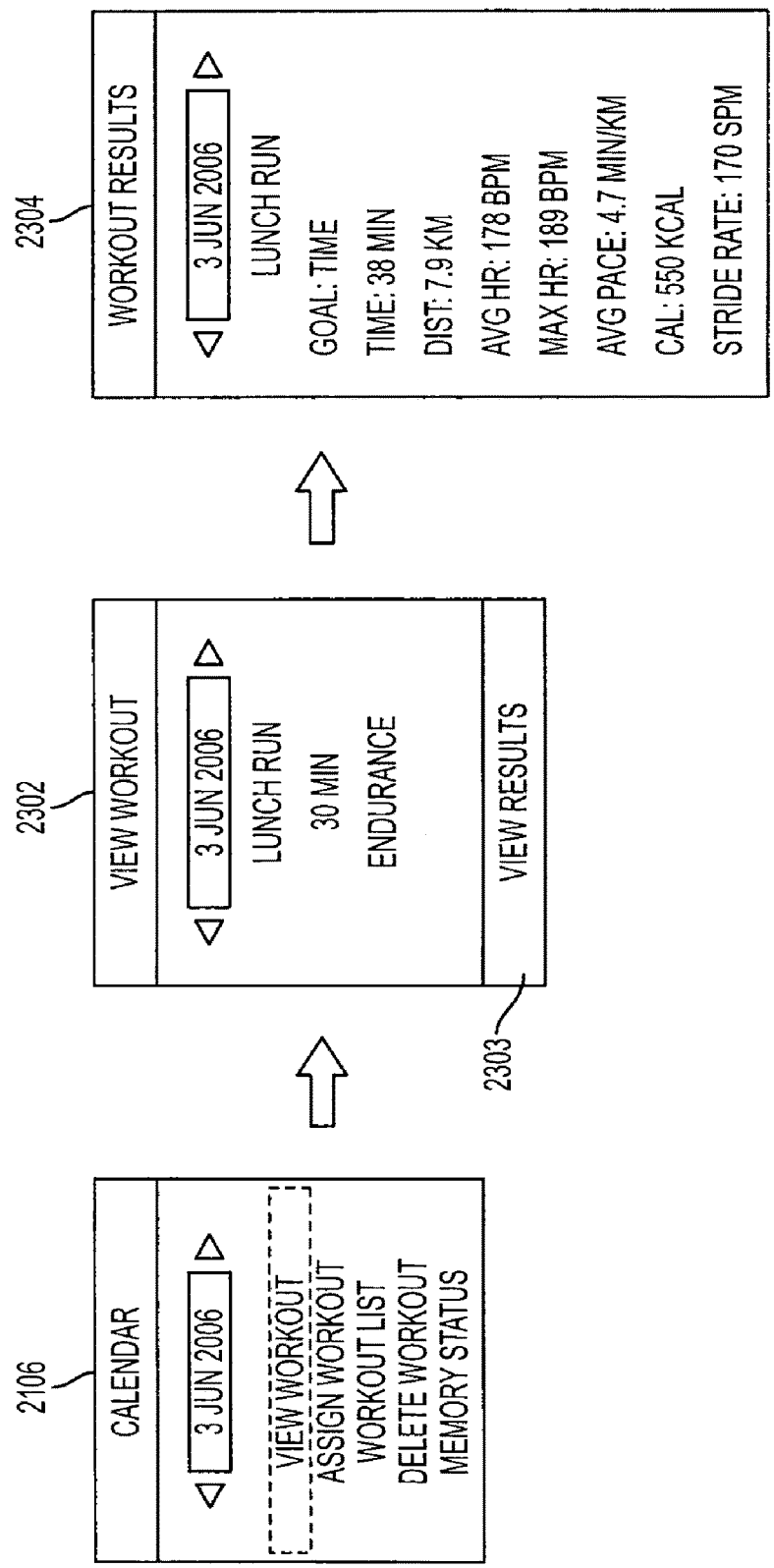

FIG. 23 is a diagram that illustrates an interaction between workout and calendar features of a sports electronic training system according to an embodiment of the present invention.

Figure 24:
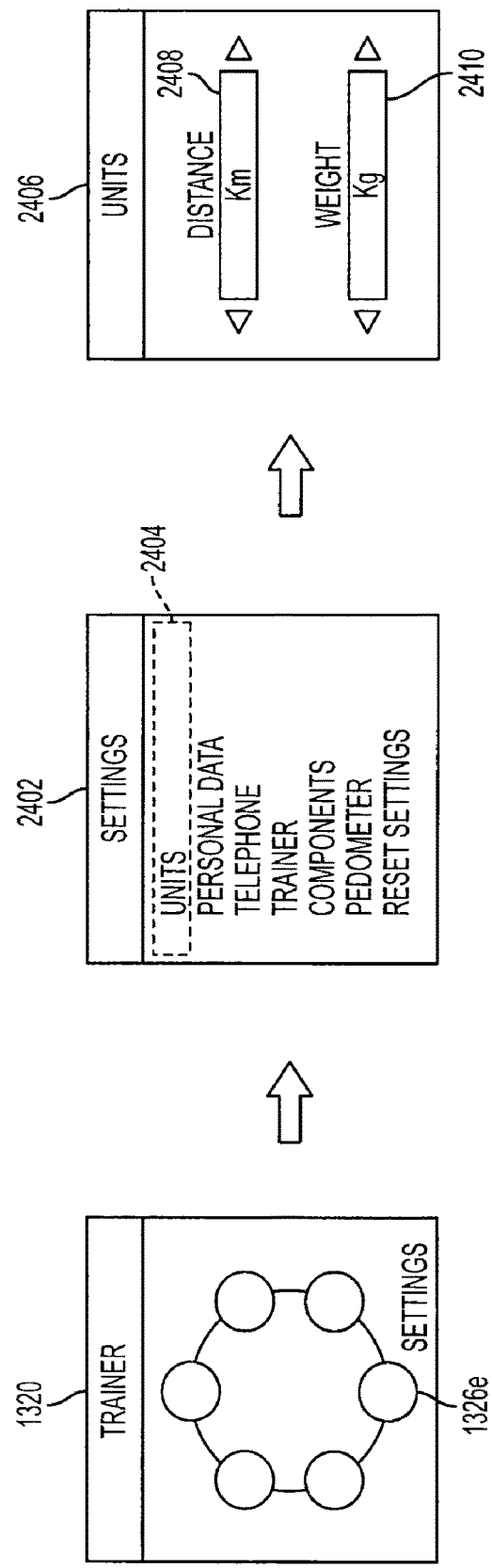

FIG. 24 is a diagram that illustrates the selection of settings for a portable electronic processing device according to an embodiment of the present invention.

Figure 25:
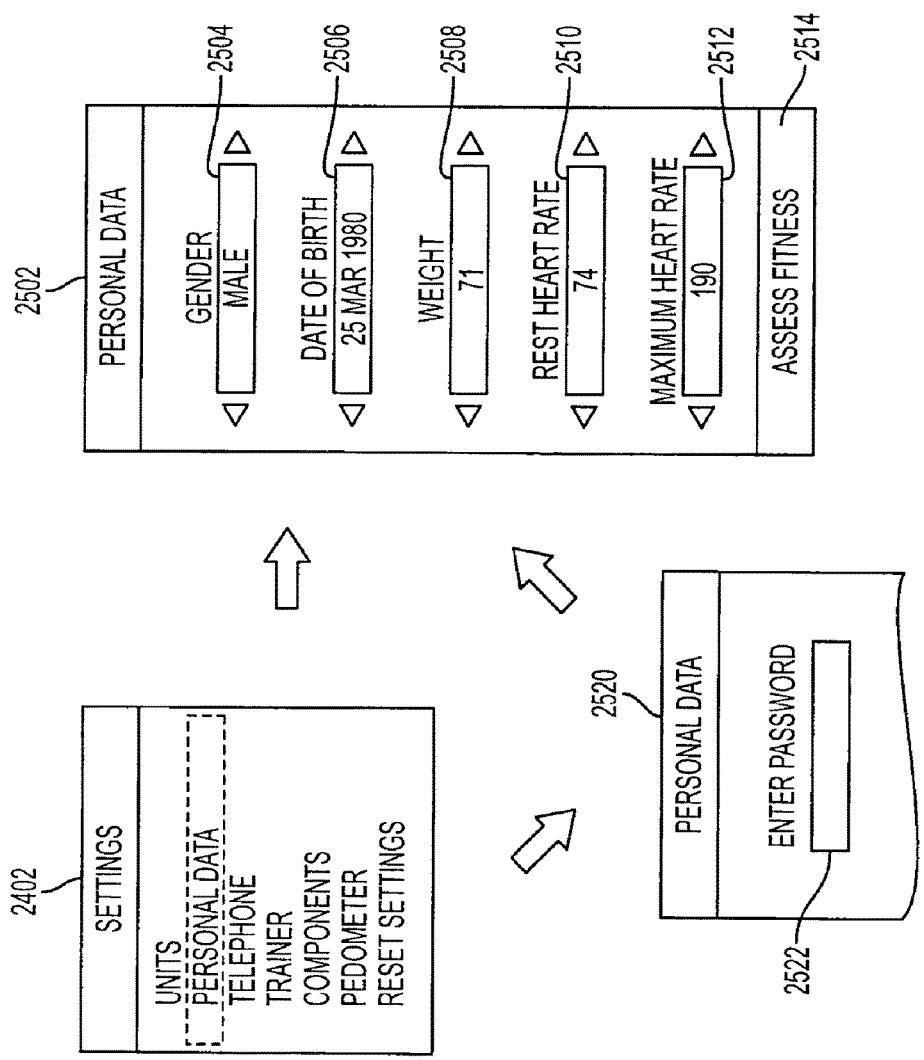

FIG. 25 is a diagram that illustrates one method for inputting and updating personal data for a sports electronic training system according to an embodiment of the present invention.

Figure 26:
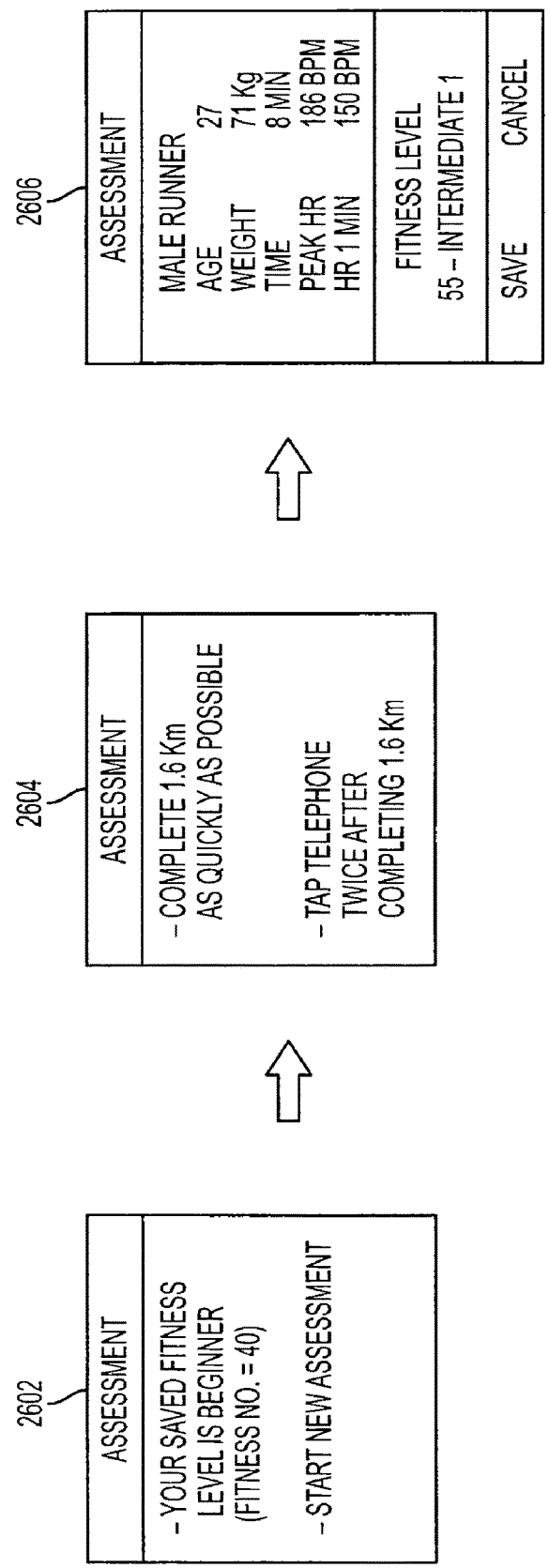

FIG. 26 is a diagram that illustrates one method for assessing a fitness level with a sports electronic training system according to an embodiment of the present invention.

FIG. 27 is a diagram of an example table used to determine a fitness level according to an embodiment of the present invention.

Figure 28:
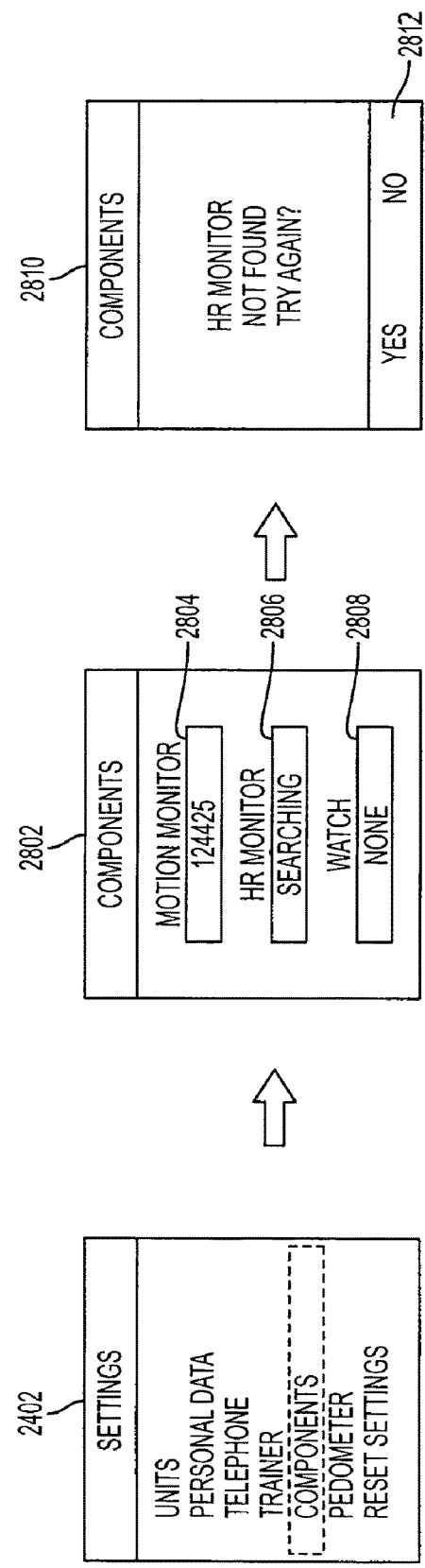

FIG. 28 is a diagram that illustrates component identification features of a sports electronic training system according to an embodiment of the present invention.

Figure 29:
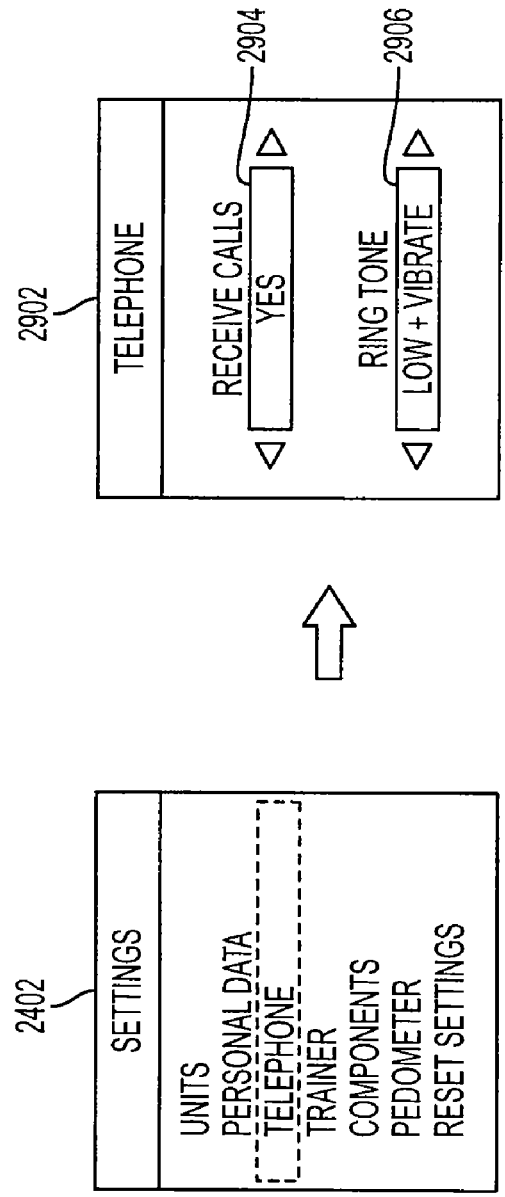

FIG. 29 is a diagram that illustrates setting telephone features of a sports electronic training system according to an embodiment of the present invention.

Figure 30:
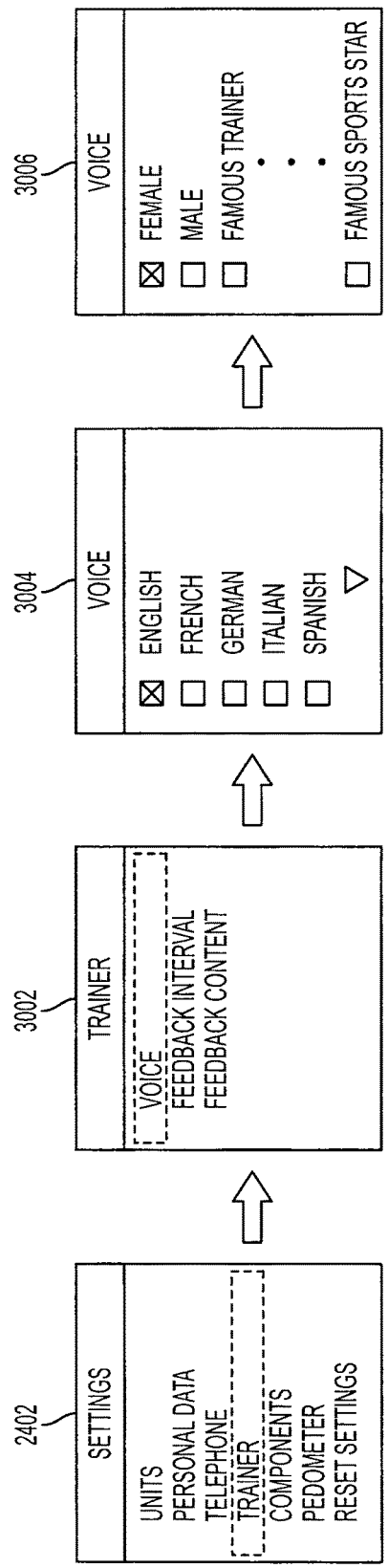

FIG. 30 is a diagram that illustrates setting virtual trainer features of a sports electronic training system according to an embodiment of the present invention.

Figure 31:
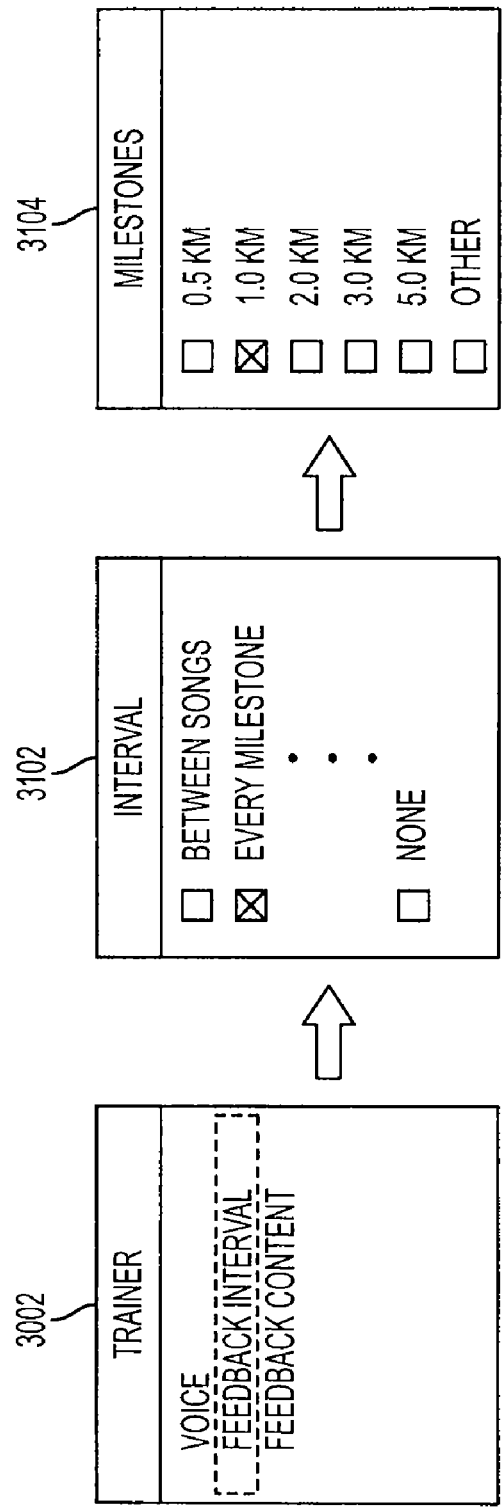

FIG. 31 is a diagram that illustrates setting virtual trainer features of a sports electronic training system according to an embodiment of the present invention.

Figure 32:
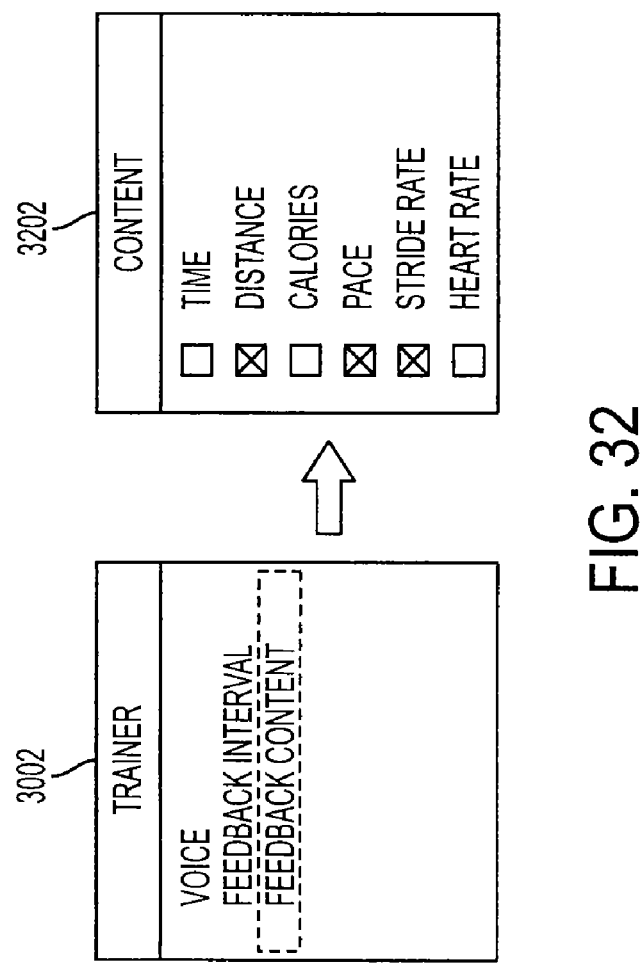

FIG. 32 is a diagram that illustrates setting virtual trainer features of a sports electronic training system according to an embodiment of the present invention.

Figure 33:
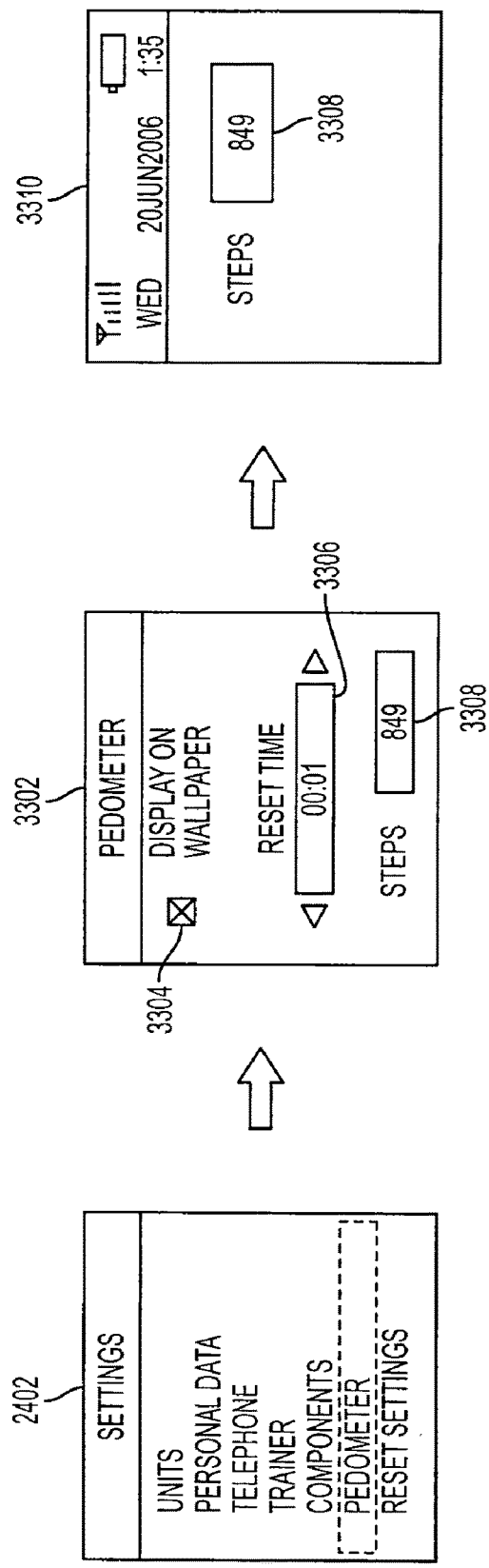

FIG. 33 is a diagram that illustrates pedometer features of a sports electronic training system according to an embodiment of the present invention.

Figure 34:
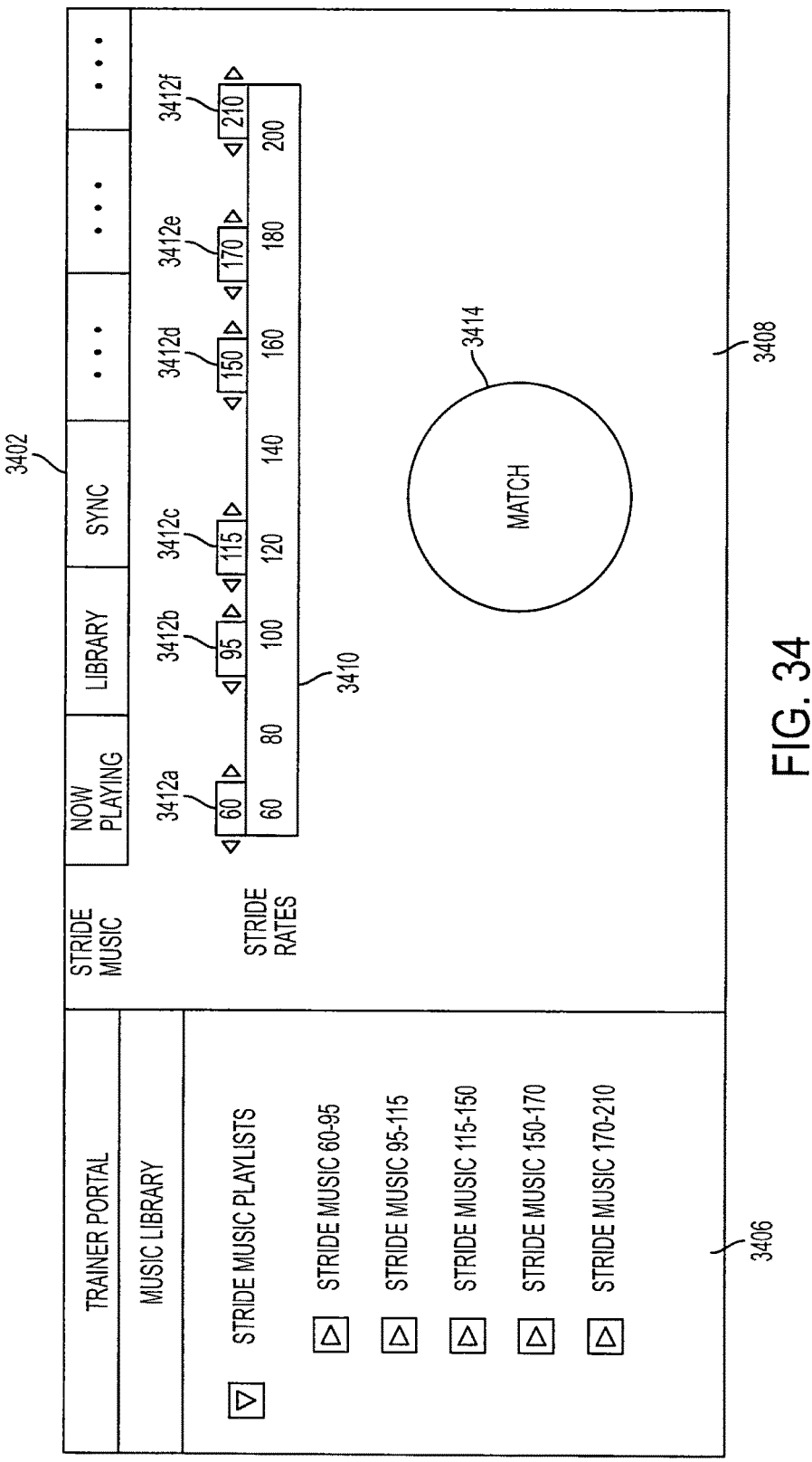

FIG. 34 is a diagram that illustrates music features of a sports electronic training system according to an embodiment of the present invention.

Figure 35:
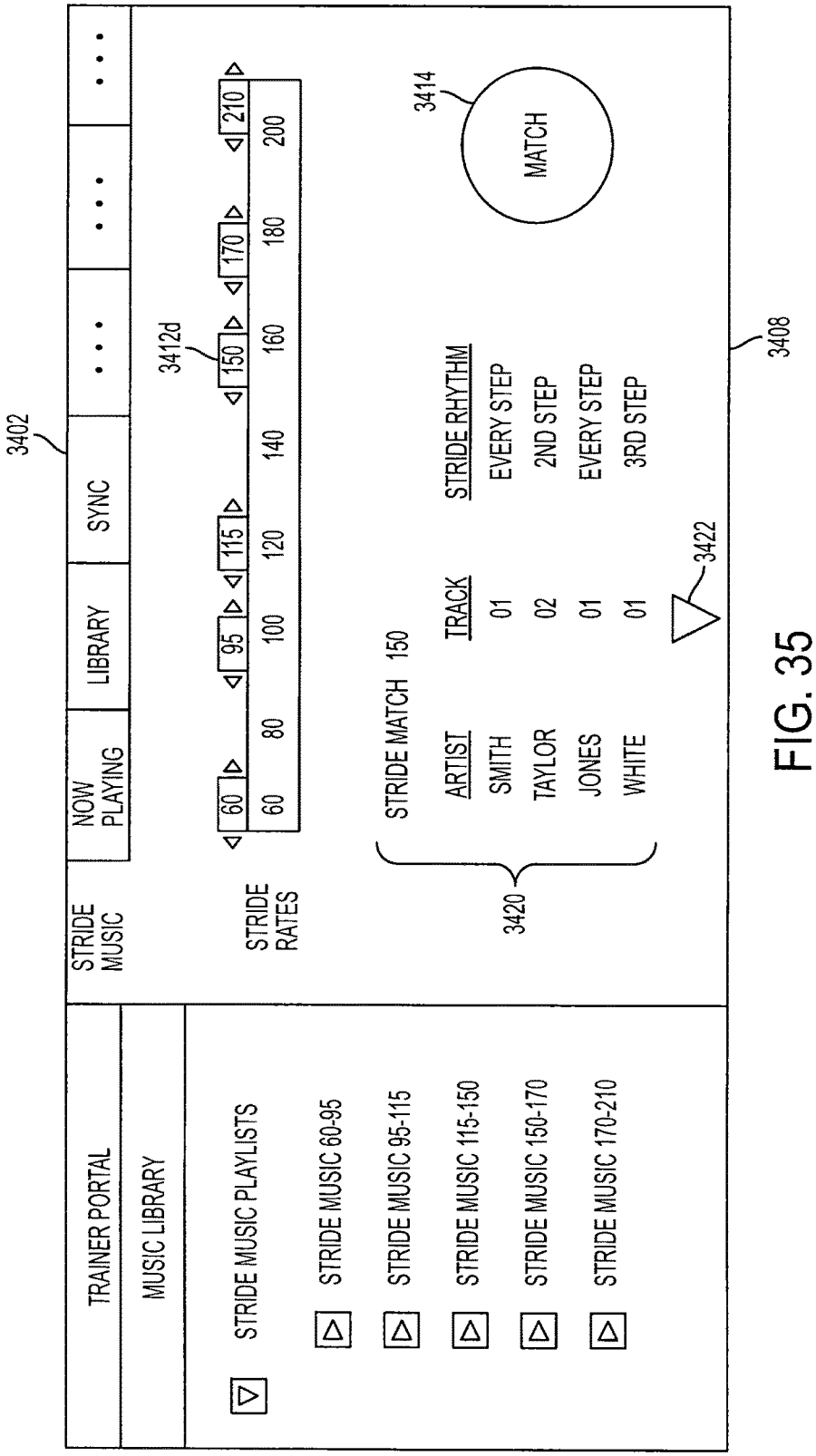

FIG. 35 is a diagram that illustrates music features of a sports electronic training system according to an embodiment of the present invention.

FIG. 36 is a diagram that illustrates music features of a sports electronic training system according to an embodiment of the present invention.

Figure 37:
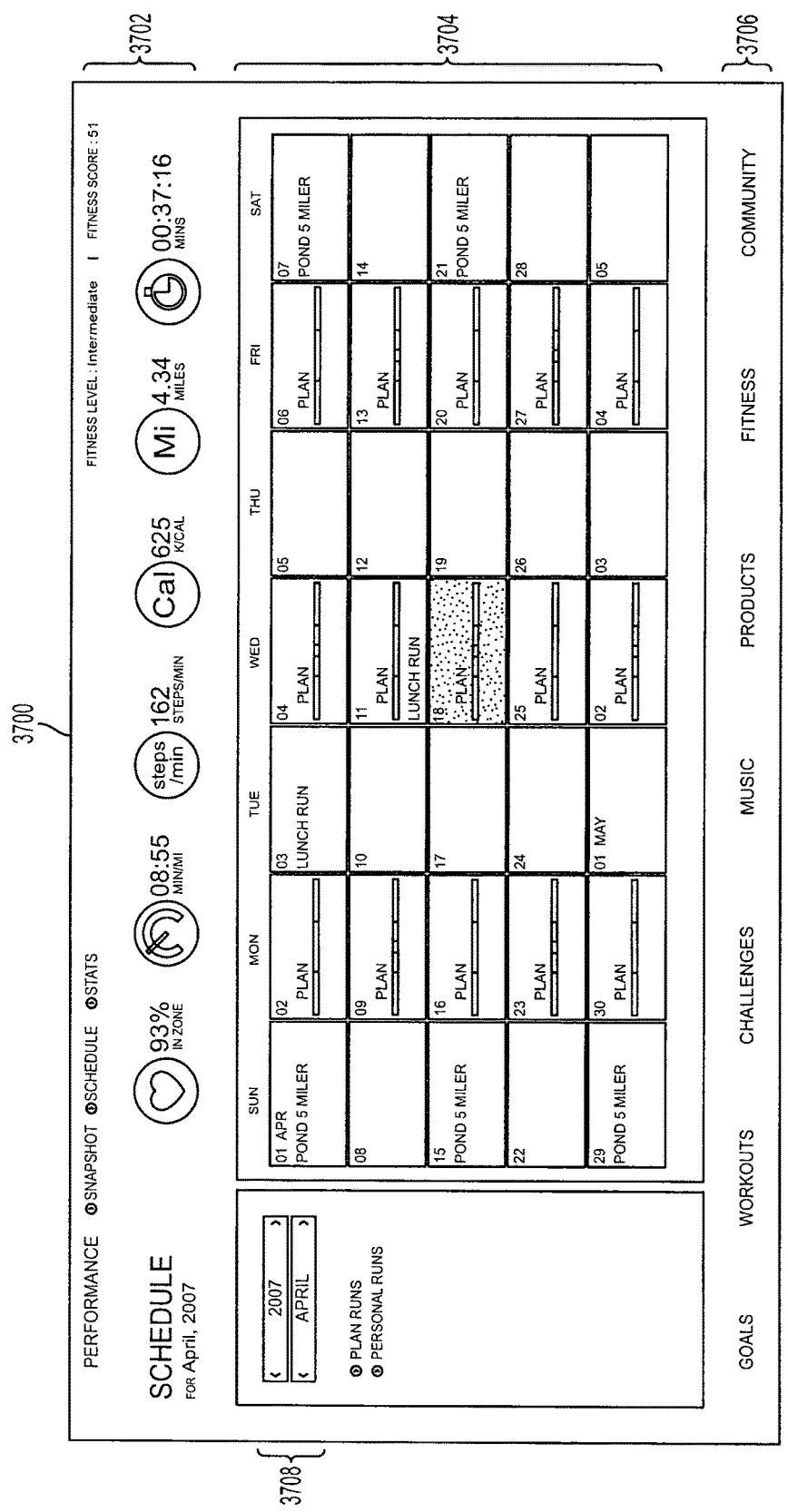

FIG. 37 is a diagram that illustrates virtual training features of a sports electronic training system according to an embodiment of the present invention.

Figure 38:
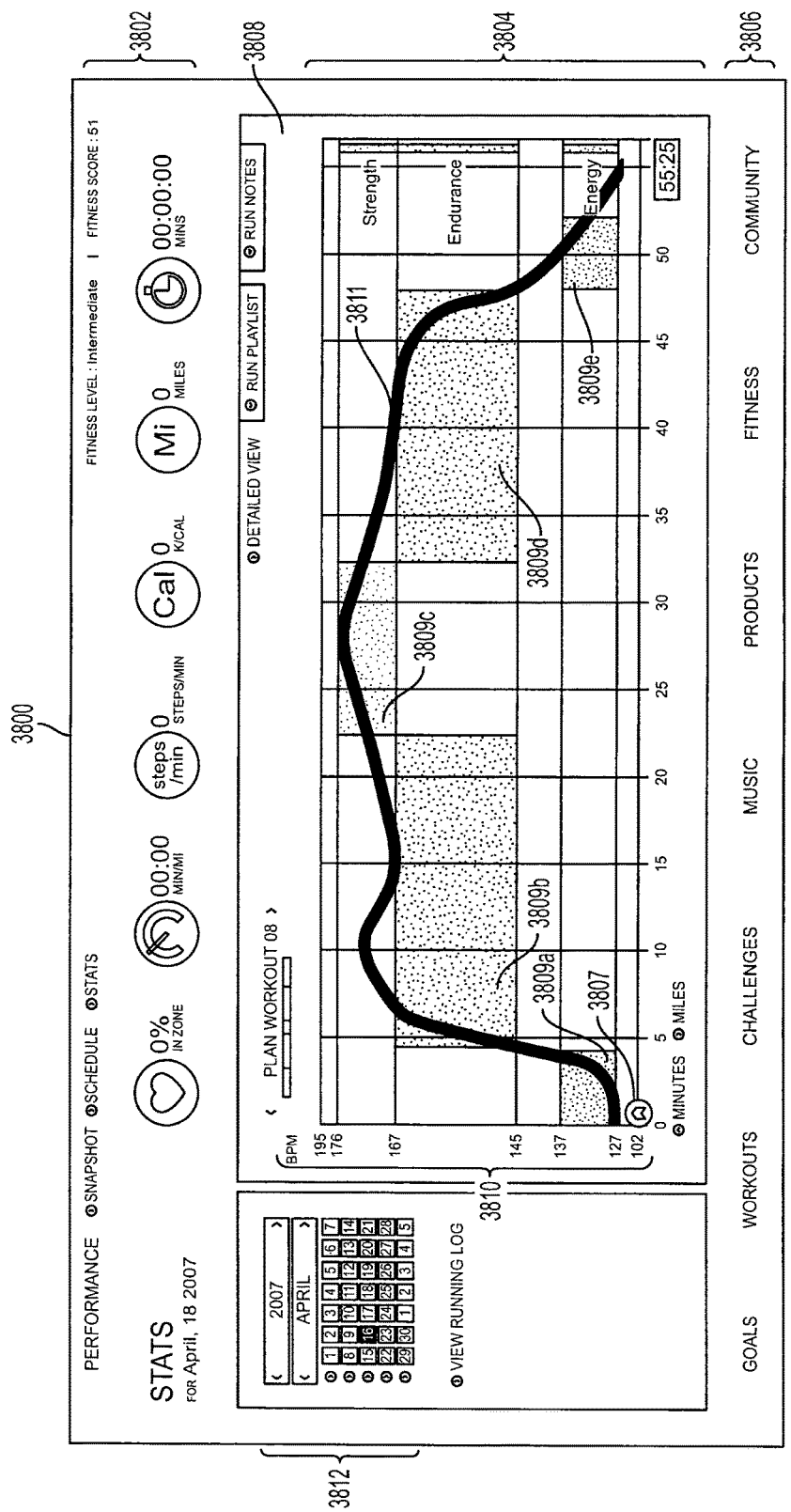

FIG. 38 is a diagram that illustrates virtual training features of a sports electronic training system according to an embodiment of the present invention.

Figure 39:
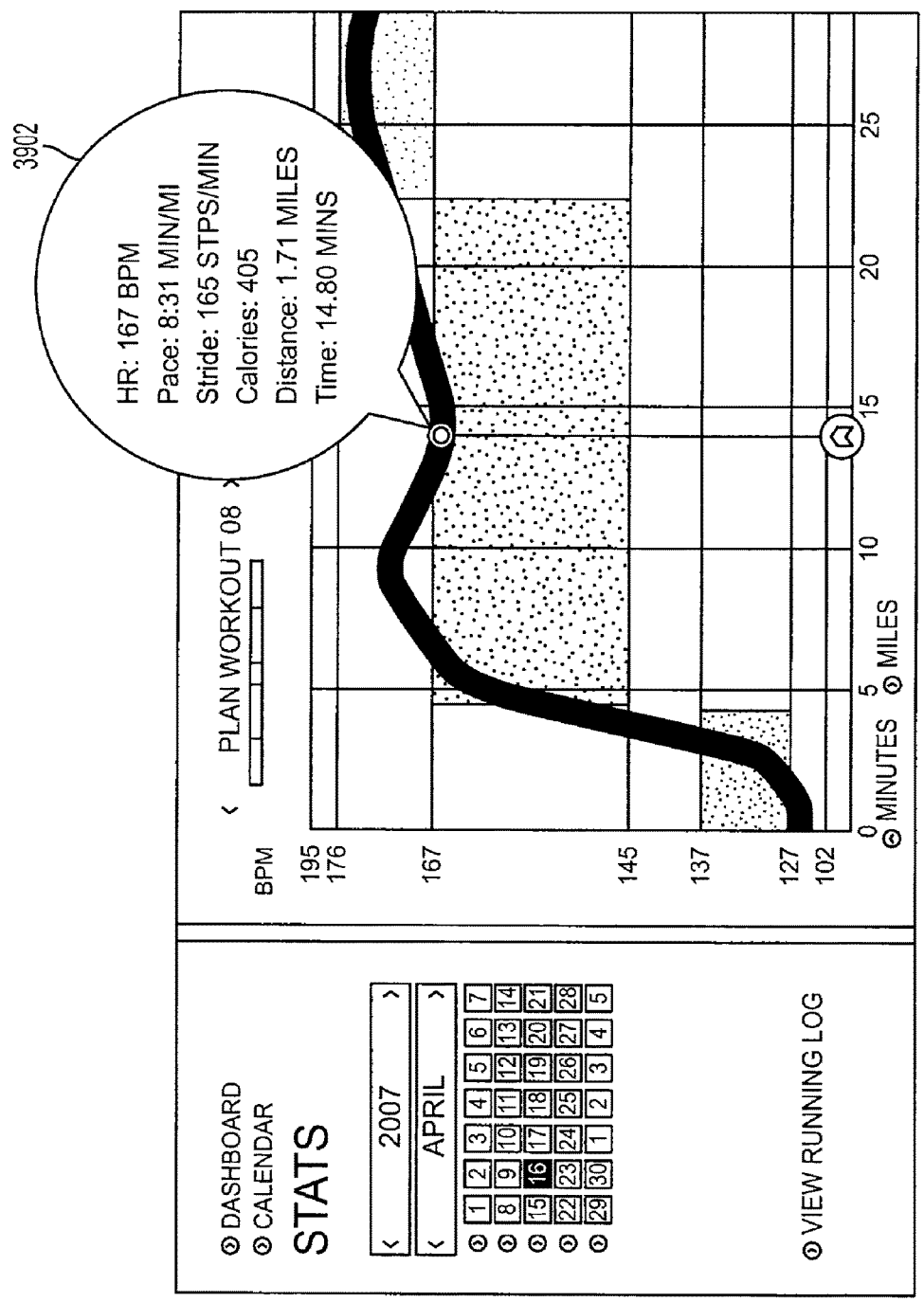

FIG. 39 is a diagram that illustrates virtual training features of a sports electronic training system according to an embodiment of the present invention.

Figure 40:
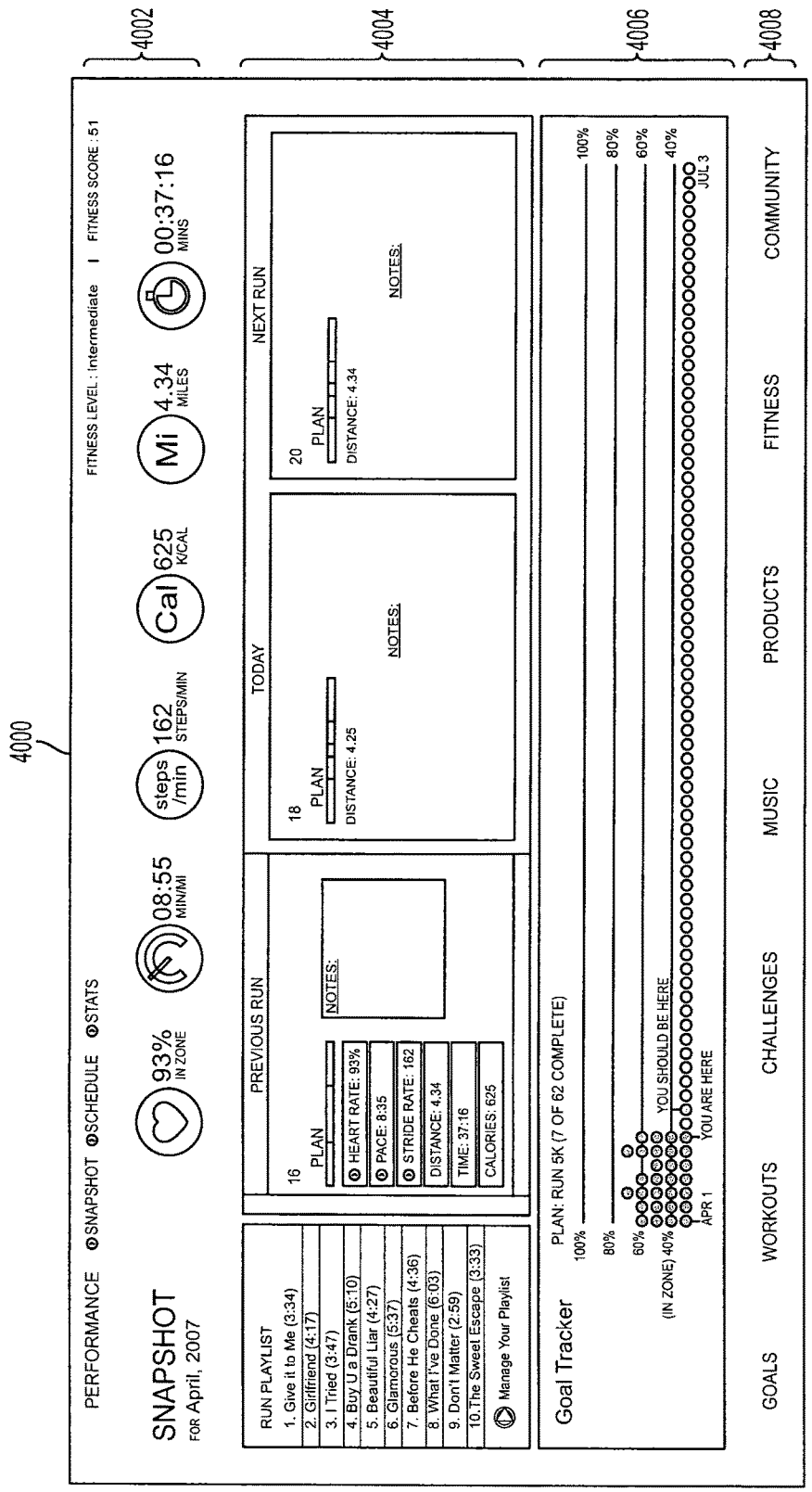

FIG. 40 is a diagram that illustrates virtual training features of a sports electronic training system according to an embodiment of the present invention.

Figure 41:
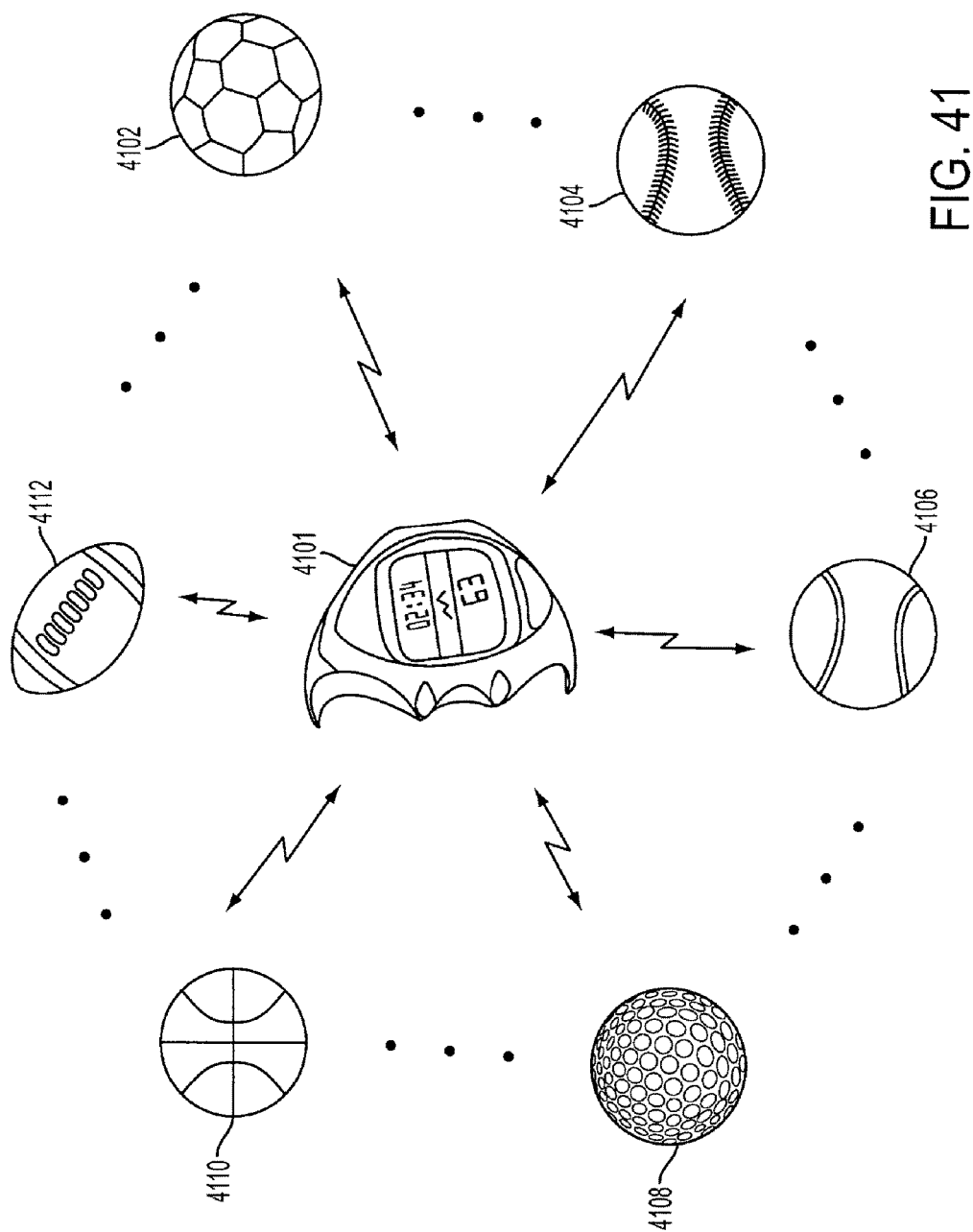

FIG. 41 is a diagram that illustrates sport balls having motion monitors that communicate with a portable electronic processing device according to an embodiment of the present invention.

Figure 42:
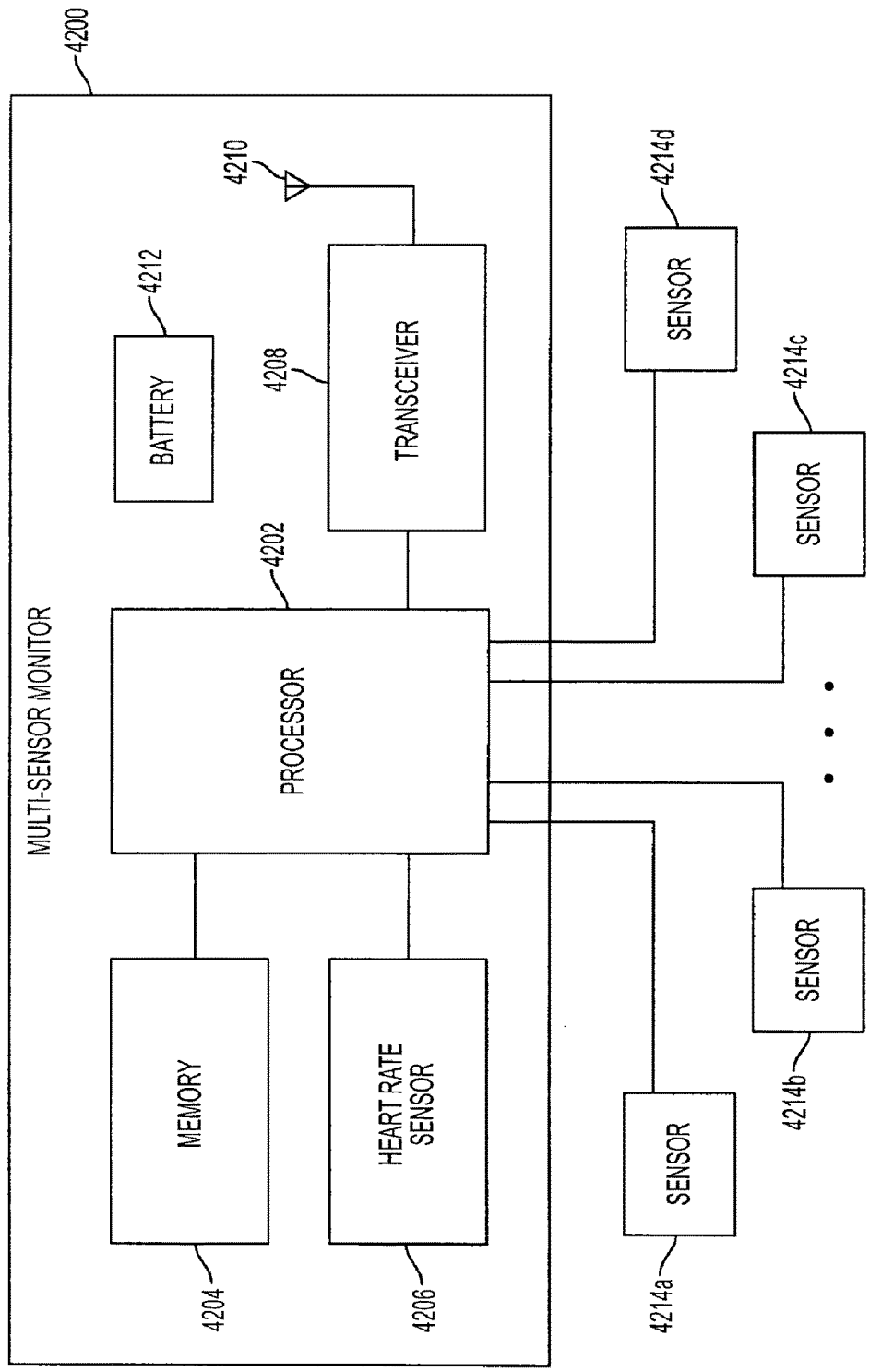
Figure 43:
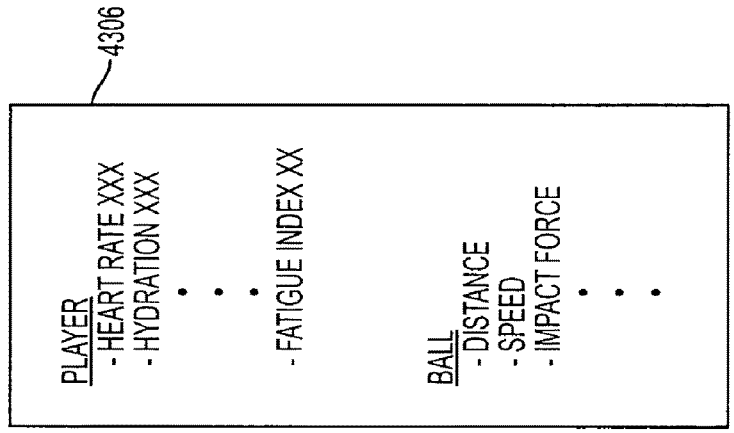
Figure 43:
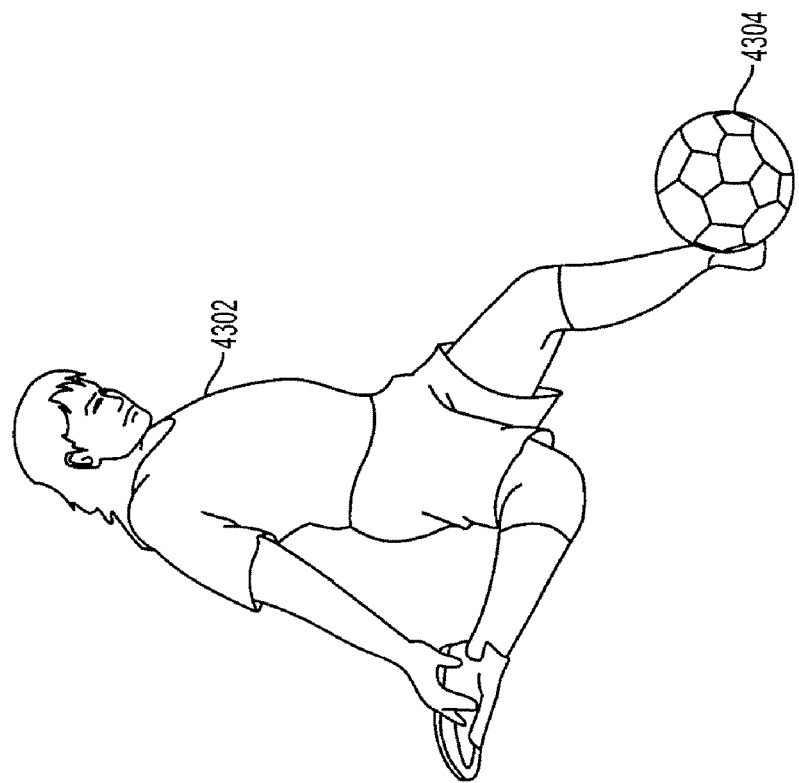

FIG. 42 is a diagram that illustrates a multi-sensor monitor according to an embodiment of the present invention FIG. 43 is a diagram that illustrates using components of the present invention to monitor a sports player and a sport ball.

Figure 44:
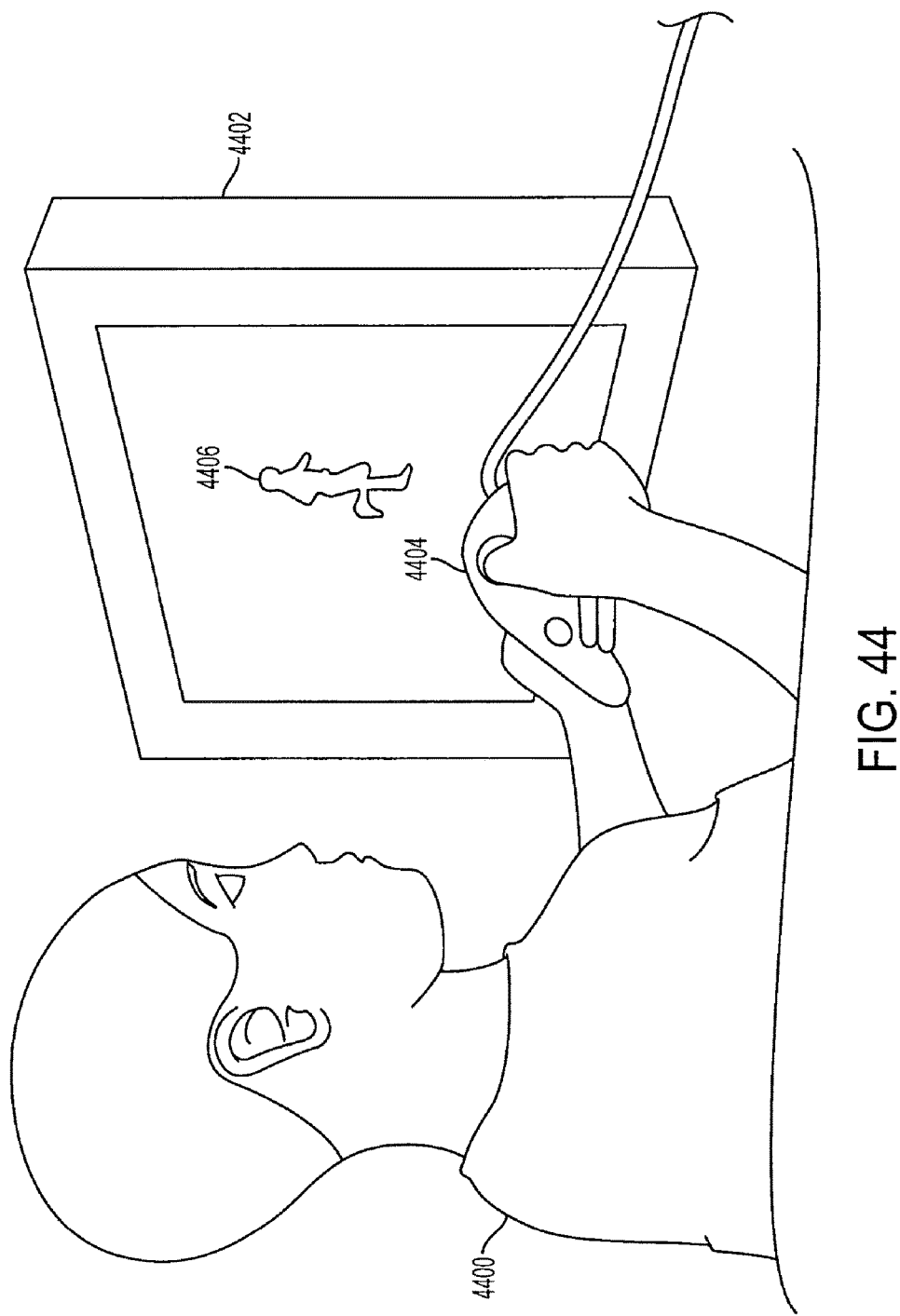
Figure 45:
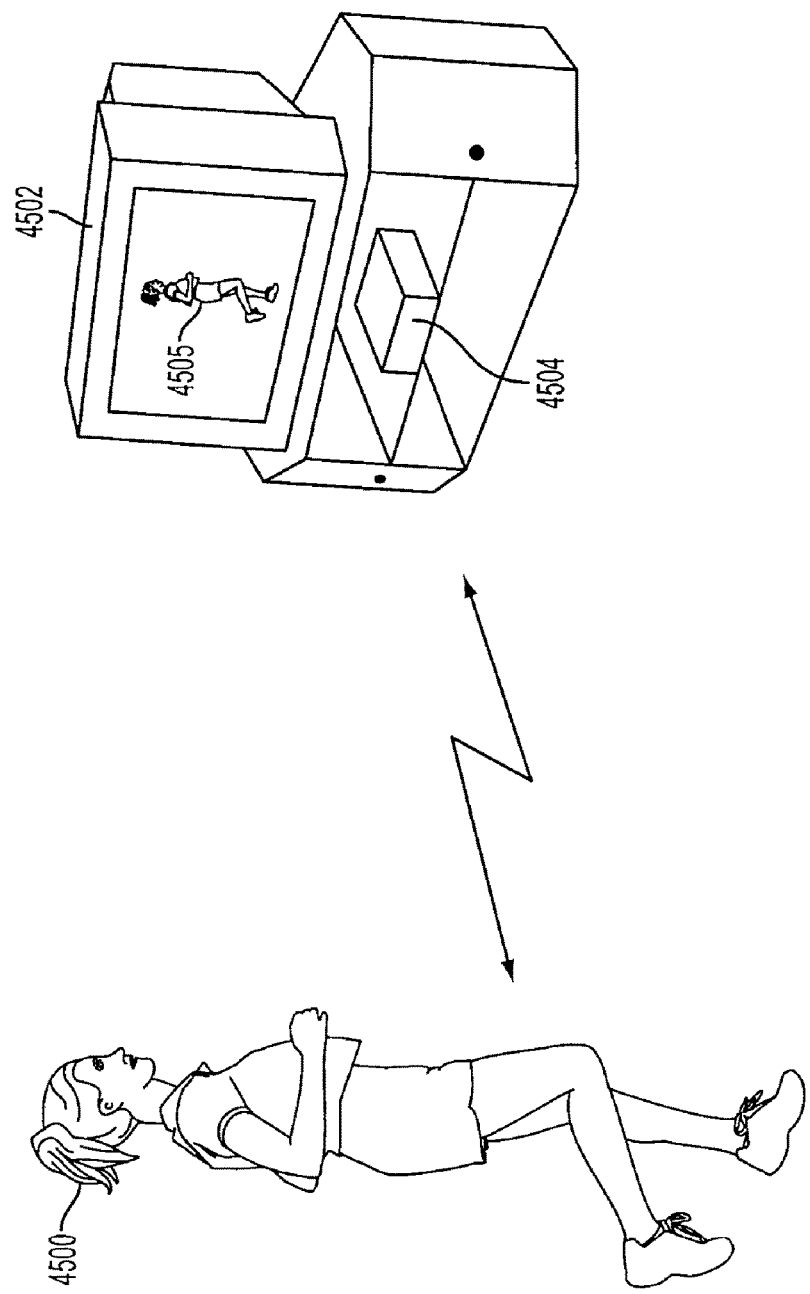

FIGS. 44 and 45 are diagrams that illustrate using components of the present invention for electronic gaming.

The present invention is described with reference to the accompanying drawings. The drawing in which an element first appears is typically indicated by the leftmost digit or digits in the corresponding reference number.

DETAILED DESCRIPTION OF THE INVENTION

The present invention provides a sports electronic training system, and applications thereof. In the detailed description of the invention that follows, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Figure 1:
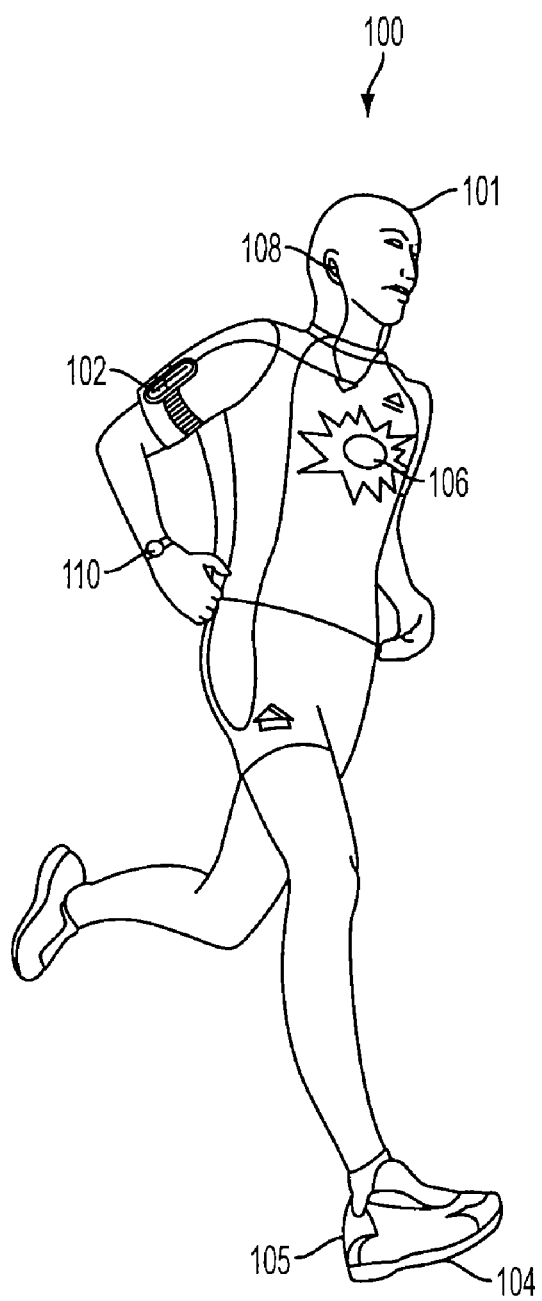
FIG. 1 is a diagram of a runner using a sports electronic training system according to an embodiment of the present invention.

FIG. 1 is a diagram of a runner 101 using a sports electronic training system 100 according to an embodiment of the present invention. As depicted in FIG. 1, in an embodiment, training system 100 includes a first portable electronic processing device 102, a motion monitor 104, a heart rate monitor 106, and a second portable electronic processing device 110. First portable electronic processing device 102, motion monitor 104, heart rate monitor 106, and second portable electronic processing device 110 communicate using a low-power wireless communications protocol and form part of a wireless personal area network (WPAN).

Portable electronic processing device 102 is shown worn on an arm of runner 101. In addition to being worn on an arm, portable electronic processing device 102 can be worn somewhere else on the runner's body such as, for example, on the runner's hip. Portable electronic processing device 102 can also be carried, for example, in a waist pack or a backpack.

In an embodiment, portable electronic processing device 102 is a device such as, for example, a mobile phone, a personal digital assistant (PDA) or a music file player (e.g., an MPEG-1 Audio Layer 3 (MP3) music file player) that includes a sports operating mode. Portable electronic processing device 102 typically acts as a WPAN receiver. It receives data from other components of training system 100 and provides training feedback to runner 101. In an embodiment, feedback is provided to runner 101 using earphones 108 that are plugged into portable electronic processing device 102. In one embodiment, portable electronic processing device 102 is used with wireless earphones (e.g., earphones that are capable of receiving wireless communications from portable electronic processing device 102).

Motion monitor 104 is shown as located in a shoe 105 worn by runner 101. In an embodiment, motion monitor 104 includes an accelerometer and determines performance parameters such as, for example, the speed, the pace, the stride rate, and the stride length of runner 101. Motion monitor 104 is also capable of determining, for example, the total distance traveled by runner 101 during a workout run. Motion monitor 104 typically acts as a WPAN transmitter.

In embodiments, motion monitor 104 is located in a location other than in shoe 105. For example, in an embodiment, motion monitor 104 is located on an exterior portion of a shoe. Furthermore, in embodiments, motion monitor 104 is located on other parts of a person's body such as, for example, on a person's hand, wrist, arm, hip, et cetera, to measure movement of the person.

Heart rate monitor 106 determines the heart rate of runner 101. In an embodiment, as depicted in FIG. 1, heart rate monitor 106 is incorporated into or attached to clothing worn by runner 101. In another embodiment, heart rate monitor 106 is worn by runner 101 using, for example, a chest strap. Heart rate monitor 106 typically acts as a WPAN transmitter.

Portable electronic processing device 110 is shown worn on a wrist of runner 101. In an embodiment, portable electronic processing device 110 is a device such as, for example, a watch that includes a sports operating mode. Portable electronic processing device 110 typically acts as a WPAN receiver. It receives data from other components of training system 100 and provides training feedback to runner 101. In an embodiment, feedback is provided to runner 101 visually using a display. In an embodiment, portable electronic processing device 110 acts as a transmitter and transmits information to components of training system 100.

FIG. 2A is a diagram further illustrating selected components of sports electronic training system 100 according to an embodiment of the present invention. These components include a mobile phone 202 having earphones 207 and a sports operating mode, a sports shirt 203 having an integral or attachable heart rate monitor 106a, a sports bra 204 having an integral or attachable heart rate monitor 106b, an athletic shoe 205 that includes a motion monitor 104, a heart rate monitor 106c integral or attached to a chest strap 206, and a sports watch 210.

As illustrated by FIG. 2A, sports electronic training system 100 is a modular system of interconnected and interactive components and products. These components and products may be acquired individually and over time as desired.

In an embodiment, mobile phone 202 includes all of the functionality typically available in a cell phone, and it is capable of playing music files (e.g., MP3 music files). In addition, mobile phone 202 includes a sports operating mode. When placed in sports operating mode, selected buttons and keys of mobile phone 202 are used to select sports mode functions. These sports mode functions are described in detail below, for example, with reference to FIGS. 13-33.

FIGS. 2B and 2C are more detailed diagrams of mobile phone 202. As shown in these figures, in an embodiment, mobile phone 202 is a flip-type mobile phone. FIG. 2B depicts mobile phone 202 in a closed position. FIG. 2C depicts mobile phone 202 in an open position.

As shown in FIG. 2B, mobile phone 202 has a user input control 215 in the middle of flip top 212 that includes four input options. User input control 215 is intended to be used primarily when mobile phone 202 is in a mode other than sports operating mode. Mobile phone 202 also has four large input buttons 220a-d. Input buttons 220a-d are active when mobile phone 202 is in sports operating mode and a rotating ring 230 is positioned in a sports lock position. The large input buttons 220a-d make it easy, for example, for runner 101 to provide input to mobile phone 202 without having to physically look at the input buttons 220a-d. This enables runner 101, for example, to wear mobile phone 202 on an arm and use the input buttons while running.

The operating mode of mobile phone 202 can be selected using a button 225 on a side of mobile phone 202. In an embodiment, pressing button 225 cycles mobile phone 202 through its various operating modes. Mobile phone 202 also includes an earphone jack 235. This permits mobile phone 202 to be used with earphones, for example, when runner 101 is exercising and/or listening to music.

As shown in FIG. 2C, a second user input control 250 is available when mobile phone 202 is in an open position. User input control 250 duplicates the user input features noted above. When mobile phone 202 is open, information can be provided to a user on a display 255.

In an embodiment, when mobile phone 202 is placed in sports operating mode (e.g., by pressing button 225), mobile phone 202 identifies and begins communicating with other components of sports electronic training system 100 to form a WPAN. This is accomplished by mobile phone 202 listening for transmissions, for example, from motion monitor 104, heart rate monitor 106, and watch 210. When mobile phone 202 receives a transmission from motion monitor 104 and/or heart rate monitor 106, for example, mobile phone 202 sends a return message that causes motion monitor 104 and/or heart rate monitor 106 to activate its sensor, if not already active, and to start transmitting performance data. Once established, the WPAN formed among the components of sports electronic training system 100 continues to operate until mobile phone 202 is placed in an operating mode other than sports operating mode. This causes mobile phone 202 to transmit a message to motion monitor 104 and/or heart rate monitor 106 that indicates to these devices that they may enter a low power mode and de-active their sensors in embodiments of these devices that include a low power mode of operation.

FIGS. 2D-F are diagrams of additional example portable electronic processing devices that have a sports operating mode according to an embodiment of the present invention.

FIG. 2D shows a mobile phone 270. Mobile phone 270 has a display 272 and a user input control 274 that is similar to user input control 250 described above.

FIG. 2E shows a portable electronic processing device 280 that includes a clip-on strap 282. Clip-on strap 282 permits portable electronic processing device 280 to be worn on an arm of a user, for example, during workouts. In an embodiment, a user can provide inputs to portable electronic processing device 280 by tapping on it when the device is in sports operating mode. For example, in an embodiment, tapping portable electronic processing device 280 twice when it is in sports operating mode activates a programmable soft key that prompts portable electronic processing device 280 to provide audible training feedback. As described in more detail below, the specific type of feedback provided is user-selectable. Additional programmable soft keys can be activated, for example, by tapping portable electronic processing device 280 three, four, or more times in a row. In one embodiment, tapping the device is used to record a change in a runner's direction (e.g., when a runner is running back-and-forth between points on a field).

FIG. 2F is a diagram of a portable electronic processing device 290. Portable electronic processing device 290 has a large display 292 that includes several touch-screen keys. A user provides inputs to portable electronic processing device 290 by touching one of the keys shown on display 292.

As illustrated by example portable electronic processing devices 270, 280, and 290, as well as other portable electronic processing devices described herein, the present invention is flexible and can be used with practically any portable electronic processing device. Accordingly, the present invention is not limited to only the devices described herein.

Referring to FIG. 2A again, athletic shoe 205 is preferably a shoe appropriate for the sport in which a user is engaged. In the case of runner 101, shoe 205 is preferably an athletic shoe built for running. In an embodiment, shoe 205 is specifically adapted to include motion monitor 104, for example, by having a recess in its sole that accepts motion monitor 104. Motion monitor 104 is preferably capable of being placed into the recess and removed from the recess by a user. This allows motion monitor 104 to be used, for example, with more than one pair of shoes.

In an embodiment, motion monitor 104 has two operating modes, an active mode and a low-power mode. In the active mode, motion monitor 104 periodically transmits a message that includes a device type identification value, a unique serial number identification value, and performance data based on input from an accelerometer. The device type identification value identifies, to a receiving device, the type of monitor from which the message was sent (e.g., a motion monitor 104 or a heart rate monitor 106). This enables the receiving device to know how the message is to be decoded. The unique serial number identification value enables the receiving device to determine whether the received message is from a device that is a part of the WPAN to which the receiving device belongs. The unique serial number identification value ensures, for example, that when multiple runners are running in a close group, mobile phone 202 only processes data from the motion monitor associated with one runner (e.g., the motion monitor that is a part of the WPAN controlled by mobile phone 202).

In low-power mode, the accelerometer and other non-essential components of motion monitor 104 are powered-down to conserve battery power. In this mode, motion monitor 104 still periodically transmits a message that contains a device type identification value and a unique serial number identification value. Because the accelerometer and other components are not functioning in low-power mode, no performance data is transmitted in low-power mode.

Immediately after each broadcast, whether in active mode or in low-power mode, motion monitor 104 turns on a receiver and listens for a message, for example, from mobile phone 202. If mobile phone 202 is in a mode other than sports mode, no message will be received and after a short period of time, motion monitor 104 can power-down its receiver until after its next transmission. If motion monitor 104 is in a low-power mode, and mobile phone 202 has been recently switched to sports operating mode, mobile phone 202 will send motion monitor 104 a message directing motion monitor 104 to switch from low-power mode to active mode. When motion monitor 104 receives this message, it will power up its components such as, for example, its accelerometer and start sending performance data as part of its periodic transmissions. Once in active mode, motion monitor 104 remains in active mode until it receives a message from mobile phone 202 telling motion monitor 104 it may return to a low-power mode.

In one embodiment, mobile phone 202 is required to periodically send a message to motion monitor 104 telling motion monitor 104 to remain in active mode. If after a predetermined period of time or number of transmissions by motion monitor 104, no such message is received from mobile phone 202, motion monitor 104 will assume that mobile phone 202 has been turned-off, and motion monitor 104 will switch to low-power mode.

In some embodiments of the present invention, communications protocols other than that described above are used. There are a number of known standard protocols and proprietary protocols that are suitable for implementing a WPAN. Accordingly, the present invention is not limited to using any particular protocol to communicate among the various components of sports electronic training system 100.

As shown in FIG. 2A, sports shirt 203 has an integral or attachable heart rate monitor 106a. Heart rate monitor 106a determines a heart rate for a wearer of sports shirt 203 and communicates this information, for example, to mobile phone 202. In an embodiment, heart rate monitor 106a communicates with mobile phone 202 in a manner similar to that described herein with regard to motion monitor 104.

Sports bra 204 also has an integral or attachable heart rate monitor 106b. Similar to heart rate monitor 106a of sports shirt 203, heart rate monitor 106b of sports bra 204 determines a heart rate for a wearer of sports bra 204 and communicates this information, for example, to mobile phone 202. In an embodiment, heart rate monitor 106b communicates with mobile phone 202 in a manner similar to that described herein with regard to motion monitor 104.

Heart rate monitor 106c is integral or attached to a chest strap 206. The monitor is worn around a user's chest in the conventional manner. Heart rate monitor 106c determines a heart rate for a wearer and communicates this information, for example, to mobile phone 202. In an embodiment, heart rate monitor 106c communicates with mobile phone 202 in a manner similar to that described herein with regard to motion monitor 104.

Sports watch 210 is similar to mobile phone 202 in that it has a sports operating mode in which it can receive messages from motion monitor 104 and/or heart rate monitor 106 and provide visual feedback to a user. Sports watch 210, however, typically does not have as much memory and/or processing power as mobile phone 202. Accordingly, sports watch 210 may not retain all of the data it receives from motion monitor 104 and/or heart rate monitor 106 during a workout for subsequent download to a computer, as described in more detail below. In an embodiment, sports watch 210 communicates with motion monitor 104 and/or heart rate monitor 106 in a manner similar to that described herein with regard to mobile phone 202.

In an embodiment, sports watch 210 acts as a controller for a portable electronic processing device such as, for example, a mobile phone, an MP3 music file player and/or a PDA. This allows the portable electronic processing device to be carried, for example, in a pocket or a backpack and still be fully controlled by sports watch 210 using wireless communications.

It should be noted that while watch 210 is described herein as a sports watch, the present invention is not limited to sports watches. Watches other than a sport watch can be used.

In an embodiment, a portable electronic processing device such as, for example, a mobile phone, an MP3 music file player and/or a PDA is controlled using soft keys/switches that are integrated into a garment (e.g., a running shirt or jacket). The garment allows the portable electronic processing device to be carried or worn underneath the garment and still be fully controlled by the garment. This is particularly beneficial, for example, in the winter when jackets are required for outdoor sport activities. In an embodiment, the garment also has an integrated display (e.g., on a sleeve in the example of a running jacket).

In one embodiment, the watchband of sports watch 210 has a moving display zone (e.g., one that moves along the band), which is always positioned for viewing by a wearer. The watchband can also include a pressure device to provide biofeedback to the wearer. In an embodiment, the feedback provided includes, for example, pressure pulsations that correspond to a stride rate goal. The wearer adjusts his or her stride rate to match the pressure pulsations. The pulsations are only provided, in one embodiment, when the wearer is running above or below the stride rate goal.

In embodiments of the present invention, forms of biofeedback other than pressure pulsations can be used to provide feedback. The biofeedback can also be applied to an area other than an individual's wrist.

In an embodiment, arrows displayed on a watchband of a sports watch indicate which way a wearer of the watch should run (e.g., the arrows provide navigation information to the wearer, for example, using satellite-based positioning system location data and mapping information). In another embodiment, a laser embodied in a component of the sports electronic training system projects a spot of light, for example, onto a runner's hand or arm, or on the ground in front of the runner, to indicate to the runner which way to run. In an embodiment, the projecting laser also provides performance information such as, for example, heart rate, pace, distance, et cetera. This information can be projected, for example, onto the ground in front of a runner.

FIG. 3A is a more detailed diagram of a first example portable electronic processing device 300 according to an embodiment of the present invention. In an embodiment, portable electronic processing device 300 corresponds to a mobile phone such as, for example, mobile phone 202. As shown in FIG. 3A, portable electronic processing device 300 includes a processor 302, memory 304, a user input control 306, a display 308, an audio unit 310, a transceiver 312, a cellular transceiver 316, an optional satellite-based positioning system receiver 305, a camera 309, and a battery 320.

Processor 302 is a conventional processor capable of implementing application programs stored in memory 304. Processor 302 is also capable of implementing digital signal processing algorithms. Processor 302 is coupled to memory 304, user input control 306, display 308, audio unit 310, transceiver 312, and cellular transceiver 316.

Memory 304 is used to store application program instructions and data. In an embodiment, memory 304 stores programs, for example, used to implement all of the functionality of a typical mobile phone as well as a program to play music files and one or more programs used to implement aspects of the functionality of sports electronic training system 100 described herein. In an embodiment, memory 304 includes both read only memory and random access memory.

User input control 306 is used by an individual to interact with portable electronic processing device 300. In an embodiment, user input control 306 includes a variety of input buttons and/or keys. The function of each of these buttons and/or keys is typically determined based on an operating mode of portable electronic processing device 300. In one embodiment, user input control 306 includes a touch pad or scroll pad and/or touch screen buttons.

Display 308 is used to display information to a user. In an embodiment, display 308 is a liquid crystal display.

Camera 309 is a small digital camera used to take digital photos. In one embodiment, camera 309 is a CCD camera. In another embodiment, camera 309 is a CMOS camera.

Audio unit 310 is used to process audio signals. In an embodiment, voice signals picked up using a microphone are converted to digital signals so that they can be operated upon, for example, by processor 302. Audio unit 310 also converts, for example, digital audio signals into amplified analog audio signals that can be used to drive one or more speakers. In an embodiment, audio unit 310 implements signal processing algorithms such as those available from Dolby Laboratories, Inc., which enhance the quality of music.

Transceiver 312 is a low-power transceiver used to communicate with other components of sports electronic training system 100. In an embodiment, transceiver 312 operates in an unlicensed frequency band such as 2.4 GHz. Transceiver 312 is coupled to an antenna 314. As used herein, the term transceiver means a combination of a transmitter and a receiver. In an embodiment, the transmitter and the receiver are integrated and form, for example, a part of an intergraded circuit.

Cellular transceiver 316 is used to send and receive, for example, voice cellular telephone signals. Transceiver 316 can also be used to exchange information with a computer network such as, for example, the Internet. Cellular transceiver 316 is coupled to an antenna 318. As used herein, the term cellular transceiver means a combination of a cellular transmitter and a cellular receiver. In an embodiment, the transmitter and the receiver are integrated together into a single device.

In one embodiment, cellular transceiver 316 is used to send data described herein to a location where it is analyzed, for example, by a professional trainer. The professional trainer can call or text message the individual and provide the individual real-time feedback based on the data. If the individuals wants to call the professional trainer, for example, during a workout, the individual can place a call to the professional trainer, for example, by tapping device 300 to place a call to a stored telephone number. In one embodiment, tapping device 300 sends a text message to the professional trainer requesting that the professional trainer call the individual.

Battery 320 is used to provide power to operate the various components of portable electronic processing device 300. In an embodiment, battery 320 is recharged periodically using a power adapter that plugs into a typical household power outlet. Battery 320 can also be a non-rechargeable battery.

In an embodiment, portable electronic processing device 300 also includes an optional satellite-based positioning system (e.g., global positioning system (GPS) or Galileo system) receiver 305. This enables portable electronic processing device 300 to determine its location anywhere on the earth. The satellite-based positioning system (e.g., GPS) receiver 305 is coupled to an antenna 307.

In an embodiment, GPS receiver 305 enables the portable electronic processing device, for example, to provide navigational instructions to a runner using the device. The directions for a running route can be down-loaded to the portable electronic processing device prior to a run and stored in memory 304. In addition to navigational instructions, attributes about the running route such as, for example, whether the route has sidewalks, is on a trail, is located within a safe neighborhood, et cetera, can also be down-loaded and viewed.

GPS receiver 305 can be used, in an embodiment, to track a route run by a runner. The route can be saved in memory 304 and viewed by the runner after the run. The route can also be shared with other runners, for example, by posting the route on a computer/web server for down-loading by other runners.

In an embodiment, GPS receiver 305 and information stored in the memory of portable electronic processing device 300 (or information received, e.g., from the internet using cellular transceiver 316) are used to provide navigational instructions, for example, to a runner. In an embodiment, the runner can enter into portable electronic processing device 300 that he or she would like to run five kilometers, for example, and the portable electronic processing device will automatically select/map-out an appropriate route and provide navigation instructions to the runner during the run. In an embodiment, the runner can specify both a start point and a stop point for the run. In an embodiment, only one point is specified, which serves as both the start point and the stop point. In an embodiment, the start and stop points are the point at which the runner is standing (e.g., as determined by GPS receiver 305) when the runner enters, for example, that he or she would like to run five kilometers.

In an embodiment, portable electronic processing device 300 includes a radio. The radio can be an AM only radio, an FM only radio, or both an AM and FM radio. In an embodiment, the radio is controlled using soft keys presented to a user on display 308.

In one embodiment, portable electronic processing device 300 includes optional sensors (not shown) for detecting selected weather related data such as, for example, temperature, humidity, ultra-violet radiation and/or barometric pressure. This data can be used, for example, to determine how an individual's performance is effected by environmental factors.

In one embodiment, a portable electronic processing device according to the present invention does not include a display. In this embodiment, information such as, for example, performance and/or feedback information is provided to a user audibly during a workout. The information can be display to the user, for example, after the workout using a computer display once the information has been transferred to the computer. In an embodiment, the information can be transferred to a second processing device such as, for example, a sports watch during the workout and displayed to the user during the workout on the display of the second processing device.

FIG. 3B is a diagram of an example portable electronic processing device 350 according to an embodiment of the present invention. In an embodiment, portable electronic processing device 350 corresponds to a device such as, for example, a PDA device, MP3 player, or an electronic watch having a sports operating mode. As shown in FIG. 3B, portable electronic processing device 350 includes a processor 352, memory 354, a user input control 356, a display 358, an audio unit 360, a transceiver 362, and a battery 366.

Processor 352 is a conventional processor capable of implementing application programs stored in memory 354. Processor 352 is also capable of implementing digital signal processing algorithms. Processor 352 is coupled to memory 354, user input control 356, display 358, audio unit 360, and transceiver 362.

Memory 354 is used to store application program instructions and data. In an embodiment, memory 354 stores programs, for example, used to implement all of the functionality of a typical PDA, MP3 player, or electronic watch and one or more programs used to implement aspects of the functionality of sports electronic training system 100 described herein. In an embodiment, memory 354 includes both read only memory and random access memory.

User input control 356 is used by an individual to interact with portable electronic processing device 350. In an embodiment, user input control 356 includes a variety of input buttons and/or keys. The function of each of these buttons and/or keys is typically determined based on an operating mode of portable electronic processing device 350. In one embodiment, user input control 356 includes a touch pad or scroll pad and/or touch screen buttons.

Display 358 is used to display information to a user. In an embodiment, display 358 is a liquid crystal display.

Audio unit 360 is used to process audio signals. In an embodiment, audio unit 360 converts, for example, digital audio signals into amplified analog audio signals that can be used to drive one or more speakers. In an embodiment, audio unit 360 implements signal processing algorithms such as those available from Dolby Laboratories, Inc., which enhance the quality of music.

Transceiver 362 is a low-power transceiver used to communicate with other components of sports electronic training system 100. In an embodiment, transceiver 362 operates in an unlicensed frequency band such as 2.4 GHz. Transceiver 362 is coupled to an antenna 364.

Battery 366 is used to provide power to operate the various components of portable electronic processing device 350. In an embodiment, battery 366 is recharged periodically using a power adapter that plugs into a typical household power outlet. Battery 366 can also be a non-rechargeable battery.

In embodiments, a portable electronic processing device according to the present invention can be formed, for example, by attaching a dongle (e.g., a small hardware device that protects software) to a conventional phone, a music file player, a personal digital assistant, et cetera. The dongle includes, for example, downloadable software that implements some or all of the sport functions described herein. In an embodiment, the software includes a sport user interface written in the Java programming language. In an embodiment, the software includes drivers, for example, that enable the software to be used with any ultra low power Bluetooth communications protocol compatible device. Other embodiments are compatible with other communications protocol compatible devices.

In an embodiment of the present invention, a portable electronic processing device according to the present invention is a dedicated device (rather than a device such as, for example, a phone, a music file player, or a personal digital assistant) that implements the sports electronic training functions described herein.

FIG. 4A is a diagram of an example motion monitor 400 according to an embodiment of the present invention. Motion monitor 400 represents one embodiment for the motion monitors described above. As shown in FIG. 4A, motion monitor 400 includes a processor 402, memory 404, an acceleration sensor 406, a transceiver 408, and a battery 410.

Processor 402 is a conventional processor such as, for example, a microcontroller capable of implementing application programs stored in memory 404. Processor 402 is coupled to memory 404, acceleration sensor 406, and transceiver 408.

Memory 404 is used to store application program instructions and data. In an embodiment, memory 404 stores programs, for example, used to generate performance data from data output by acceleration sensor 406. In an embodiment, memory 404 includes both read only memory and random access memory.

In an embodiment, acceleration sensor 406 is an electronic accelerometer that measures acceleration in one or more axes. The one or more axes provide a stream of acceleration data that correspond, for example, to the motion of a runner's foot whenever motion monitor 400 is attached to a runner's shoe.

Transceiver 408 is a low-power transceiver used to communicate with other components of sports electronic training system 100. In an embodiment, transceiver 408 operates in an unlicensed frequency band such as 2.4 GHz. Transceiver 408 is coupled to an antenna 412.

Battery 410 is used to provide power to operate the various components of motion monitor 400. In an embodiment, battery 410 is either a rechargeable battery or a non-rechargeable battery that must be periodically replaced (e.g. every one to two years or longer).

In an embodiment, processor 402 operates on data provided by acceleration sensor 406 to generate performance data such as, for example, the speed, the pace, the stride rate, the stride length, and the total distance traveled by a runner. The performance data is transmitted using transceiver 408 for reception by a portable electronic processing device such as, for example, portable electronic processing device 300 and/or portable electronic processing device 350.

In one embodiment, motion monitor 400 generates performance data as follows. Processor 402 low-pass filters and examines the stream of output values generated by one axis of acceleration sensor 406 (e.g., an axis aligned with the heel-to-toe axis of an individual) to identify a maximum acceleration value and/or a minimum acceleration value for each stride of an individual. The average speed of the individual during each stride is then calculated by processor 402 using an appropriate algorithm stored in memory 404. This is possible because the average speed of an individual (whether running or walking) is proportional to the maximum and minimum acceleration values that occur during each stride of the individual. Why this is so is illustrated, for example, by FIGS. 4B and 4C.

FIGS. 4B and 4C are diagrams that illustrate how motion monitor 400 determines performance data such as, for example, the speed, the pace, the stride rate, the stride length, and the total distance traveled by an individual in an embodiment of the present invention.

As shown in FIG. 4B, an individual's leg has a specific movement pattern during each stride relative to the direction in which the individual is traveling (e.g., direction X). At a time period 420, for example, the beginning of a stride, the foot of one leg of an individual is planted firmly on the ground and is not moving in the direction of travel. Since there is no movement of the foot, there is also no acceleration $A_X$ in the direction of travel. As the individual's hips and upper body move forward in the direction of travel at a speed $S_X$, the upper portion of the individual's leg begins to move forward at a time period 422 relative to the direction in which the individual is traveling, while the lower portion of the individual's leg begins to move backwards relative to the direction of travel. This generates a negative acceleration $A_X$ in the direction of travel that is detected by a first axis (e.g., the X axis) of acceleration sensor 406.

At a later point in time during the stride, time period 424 in FIG. 4B, the upper portion of the individual's leg is still moving forward relative to the direction of travel when the lower portion of the individual's leg begins to move forward relative to the direction of travel of the individual. This generates a positive acceleration $A_X$ in the direction of travel of the individual that is detected by the first axis of acceleration sensor 406.

At a time period 426 during the stride, the upper portion of the individual's leg has stopped moving forward relative to the direction of travel while the lower portion of the individual's leg is continuing to move forward relative to the direction of travel of the individual. This stage of the stride also generates a positive acceleration $A_X$ in the direction of travel of the individual that is detected by the axis of acceleration sensor 406.

Finally, at the end of the stride, time period 428 in FIG. 4B, the individual's foot is again firmly planted on the ground. There is no movement of the foot in the direction of travel at this time period, and the acceleration $A_X$ along the first axis is zero.

FIG. 4C illustrates an idealized, filtered output of acceleration sensor 406 of motion monitor 400 corresponding to the stride of an individual (e.g., whether running or walking). As depicted, there is a period of negative acceleration having a minimum acceleration value and a period of positive acceleration having a maximum acceleration value during each stride. Using this information, the average speed of the individual in the direction of travel during the stride is given, for example, by equation 1 below:

$$S_X = K_1 \{fx_1(A_{max}, T_3-T_2)\} + K_2 \quad \text{EQ. 1}$$

where $S_X$ is the average speed for the stride, $K_1$ is a proportionality constant, $fx_1$ is a function involving Amax (the maximum acceleration value generated during the stride processed through a low pass filter) and $T_3-T_2$ (the period of positive acceleration), and $K_2$ is an adjustment constant. The values $K_1$ and $K_2$ are empirical values that are determined experimentally, and in an embodiment they are different for different ranges of speed (e.g., one set of values is used if an individual is walking and another set of values is used if the individual is running). The function $fx_1$ is determined experimentally, and in embodiments can be a higher order (e.g., a second order or a third order) equation.

In one embodiment, the value(s) for $K_1$ and/or $K_2$ are initially determined, for example, based on an input length for a user's leg (e.g., measured from the knee to the heel) or an input height for the user (e.g., using an assumption that the length of the leg is some fraction of the height).

In an embodiment, the value(s) for $K_1$ and/or $K_2$ are determined and/or updated by having the user run a known distance and using this known distance to determine and/or update the value(s) for $K_1$ and/or $K_2$.

As noted herein, it is possible to determine the average speed for the stride using the minimum acceleration value. This is done, for example, using equation 2 below:

$$S_X = K_3 \{fx_2(A_{min}, T_2-T_1)\} + K_4 \quad \text{EQ. 2}$$

where $S_X$ is the average speed for the stride, $K_3$ is a proportionality constant, $fx_2$ is a function involving $A_{min}$ (the minimum acceleration value generated during the stride processed through a low pass filter) and $T_2-T_1$ (the period of negative acceleration), and $K_4$ is an adjustment constant. The values $K_3$ and $K_4$ and the function $fx_2$ are determined experimentally. In embodiments, the function $fx_2$ can be a higher order (e.g., a second order or a third order) equation.

In one embodiment, the average speed is calculated by combining equations 1 and 2 and forming a third equation for the average speed during a stride. This third equation is:

$$S_X = K_1 \{fx_1(A_{max}, (T_3-T_2))\} - K_3 \{fx_2(A_{min}, (T_2-T_1))\} + K_{2+4} \quad \text{EQ. 3}$$

where $S_X$ is the average speed for the stride, $K_1$ and $K_2$ are proportionality constants, $fx_1$ is a function involving Amax (the maximum acceleration value generated during the stride processed through a low pass filter) and $T_3-T_2$ (the period of positive acceleration), $fx_2$ is a function involving $A_{min}$ (the minimum acceleration value generated during the stride processed through a low pass filter) and $T_2-T_1$ (the period of negative acceleration), and $K_{2+4}$ is an adjustment constant. The values $K_1$, $K_3$ and $K_{2+4}$ and the functions $fx_1$ and $fx_2$ are determined experimentally. In embodiments, the functions $fx_1$ and $fx_2$ can be higher order (e.g., second order or third order) equations.

Using the information provided herein, it is possible to develop other algorithms for determining the average speed during a stride. For example, the output of more than one axes of acceleration sensor 406 can be used, in which the output values would be combined using, for example, a square root of the sum of the squares approach. Accordingly, the present invention is not limited to using just the algorithms described herein.

Once the average speed for each stride is calculated, calculating other performance parameters is possible. For example, the distance traveled during each stride (e.g., stride length) is given by equation 4 below:

$$D_X = S_X(T_3-T_1) \quad \text{EQ. 4}$$

where $D_X$ is the stride length, $S_X$ is the average speed during the stride, and $T_3-T_1$ is the time of a single stride. Stride rate is determined by dividing 1 minute by $T_3-T_1$ to determine the number of strides per minute. The total distance traveled by the individual is the sum of all stride lengths. Pace is calculated, for example, by inverting the average speed value and adjusting the unit to obtain a desired time per distance value (e.g., minutes per kilometer, minute per mile, et cetera).

It is to be noted that while the values for $K_1$ and $K_2$ can be determined and selected based on information provide by a user (e.g., by asking a user to provide the length of his or her leg or his or her height), it is desirable to have the individual walk or run a particular known distance and use this information to adjust the values for $K_1$ and $K_2$ (i.e., to calibrate motion monitor 400 for the particular user). Doing this leads to improved accuracy. Additionally, it may also be beneficial to have one set of K values that are used in an algorithm when a user is walking and another set of K values that are used when the user is running. Whether the user is walking or running can be determined, for example, using a threshold acceleration value. For example, if the maximum acceleration value detected is below a certain threshold, it is assumed that the user is walking. Otherwise, it is assumed the user is running.

In an embodiment, calibration of motion monitor 400 is performed using, for example, received GPS signals. The received GPS signals can be used, for example, to determine a distance that a user runs or walks during a workout.

In one embodiment, motion monitors according to the present invention are used to detect changes in an individual's direction of motion. For example, one or more motion monitors can be worn by a basketball player and used to track the basketball player's forwards and backwards motion as well as side-to-side motion. In an embodiment, every basketball player's position on a basketball court during a basketball game can be tracked using motion monitors and displayed, for example, for analysis by a coach. Motion monitors according to the present invention can also be worn by individuals and used to detect and/or track other motions such as, for example, motions associated with push-ups, pull-ups, weightlifting, diving, gymnastics, et cetera.

FIG. 5 is a diagram of an example heart rate monitor 500 according to an embodiment of the present invention. Heart rate monitor 500 represents one embodiment for the example heart rate monitors described above. As shown in FIG. 5, heart rate monitor 500 includes a processor 502, memory 504, a heart rate sensor 506, a transceiver 508, and a battery 512.

Processor 502 is a conventional processor such as, for example, a microcontroller capable of implementing application programs stored in memory 504. Processor 502 is coupled to memory 504, heart rate sensor 506, and transceiver 508.

Memory 504 is used to store application program instructions and data. In an embodiment, memory 504 stores programs, for example, used to generate heart rate data from data output by heart rate sensor 506. In an embodiment, memory 504 includes both read only memory and random access memory.

Heart rate sensor 506 is an electronic sensor that detects heart beats. This data is provided to processor 502 and used to determine a heart beat rate (e.g., number of beats per minute).

Transceiver 508 is a low-power transceiver used to communicate with other components of sports electronic training system 100. In an embodiment, transceiver 508 operates in an unlicensed frequency band such as 2.4 GHz. Transceiver 508 is coupled to an antenna 510.

Battery 512 is used to provide power to operate the various components of heart rate monitor 500. In an embodiment, battery 512 is either a rechargeable battery or a non-rechargeable battery that must be periodically replaced.

In one embodiment, heart rate can be monitored, for example, using portable electronic processing device 300 and earphones plugged into device 300. In this embodiment, the heart rate sensors are integral to the earphones, and because the earphones are worn on opposite sides of the user's heart, they can be used to detect heart beats. In another embodiment, heart rate is monitored using devices that clip onto a user's ear or a user's finger and determine heart rate by looking at blood flow. In embodiments, heart rate monitors can be used that clip onto products such as, for example, sunglasses.

FIG. 6A is a diagram of a shoe 600 having a motion monitor 602 inserted into a recess in sole 604 of shoe 600 according to an embodiment of the present invention. The recess positions motion monitor 602 in such a way that a surface of the motion monitor's housing is parallel to and in the plane of the top of sole 604. Placing motion monitor 602 in the recess of sole 604 is desirable because, in an embodiment, one of the acceleration sensor axis of motion monitor 602 is parallel to the plane of the motion monitor's housing surface, and placing the motion monitor in this orientation may provide greater accuracy than other orientations such as, for example, attaching motion monitor 602 to an external surface of shoe 600. In an embodiment, the recess in the sole that houses motion monitor 602 is located in the mid-foot region of shoe 600 (e.g., where there is a minimum of flex of shoe 600).

FIG. 6B is a diagram of a shoe 606 having motion monitor 602 mounted on an external portion of shoe 606. As shown in FIG. 6B, motion monitor 602 is mounted using a mounting device 608. Mounting device 608 is held onto the top of shoe 606, for example, using shoe laces. Mounting device 608 permits motion monitor 602 to be removed and inserted into the mounting device without taking the mounting device off of shoe 606.

FIG. 6C is a more detailed diagram of motion monitor 602 according to an embodiment of the present invention. In an embodiment, motion monitor 602 is enclosed in a hard plastic protective housing 620. A surface 621 of motion monitor 602 includes a mark 622 that is used to ensure proper orientation of motion monitor 602, for example, when it is inserted into a shoe. In an embodiment, mark 622 should be oriented facing towards the toe portion of the shoe. In other embodiments, however, the motion monitor will work properly regardless of orientation.

A second surface 624 of motion monitor 602 includes a removable cap 626. In an embodiment, removable cap 626 is removed by turning it less than a quarter turn in one direction. Removable cap 626 provides access to a battery 628, which can be removed and replace with a fully charged battery, as needed. In an embodiment, battery 628 is a button type battery.

FIG. 6D is a more detailed diagram of mounting device 608. In an embodiment, mounting device 608 is made of a semi-rigid plastic that allows motion monitor 602 to be snapped into mounting device 608 and firmly held in place. Mounting device 608 includes four clips 630a-d that hold motion monitor 602 in place. The mounting device can be placed on a shoe, for example, by slipping clips 630a and 630b under one or more shoe laces so that the shoe laces rest on surface 632 of mounting device 608. In an embodiment, the surface of mounting device 608 that rests on the shoe is textured to reduce any slippage that might otherwise occur.

FIG. 6E is a diagram of a motion monitor 602 that has a housing 639 and a winged-battery cap 640 for mounting the motion monitor on a shoe according to an embodiment of the present invention. The housing 639 and the winged-battery cap 640 have bayonet-type quick connect and disconnect threads that only require, for example, a one-quarter turn of housing 639 to securely fasten housing 639 to winged-battery cap 640.

FIG. 6F is a diagram that shows motion monitor 602 of FIG. 6E mounted on a shoe 642. The shoe laces of shoe 642 cross-over winged-battery cap 640 to hold motion monitor 602 in place.

FIG. 6G is a diagram of a housing 643 for motion monitor 602 that has a winged-battery cap 644 for mounting the motion monitor on a shoe according to an embodiment of the present invention. Housing 643 and winged-battery cap 644 are similar to housing 639 and winged-battery cap 640, except for the type of threads that is used to couple winged-battery cap 644 to housing 643. The threads used with housing 643 and winged-battery cap 644 require several turns to couple housing 643 to winged-battery cap 644.

FIG. 6H is a diagram that further illustrates how winged-battery cap 644 is screwed into housing 643.

FIG. 6I is a diagram of a winged-battery cap 646 for use, for example, with housing 643. Winged-battery cap 646 has ends with openings through which the laces of a shoe can be threaded. A similar winged-battery cap with bayonet-type quick connect and disconnect threads can be used with housing 639.

FIG. 6J is a diagram of a winged-battery cap 648 for use, for example, with housing 643. Winged-battery cap 648 has ends with two holes each through which the laces of a shoe can be threaded. A similar winged-battery cap with bayonet-type quick connect and disconnect threads can be used with housing 639.

FIG. 7 is a diagram of a heart rate monitor 700 with built-in sensors 702*a-b* for determining a user's percent body fat according to an embodiment of the present invention. In an embodiment, a percent body fat value is determined by having a user grasp sensors 702*a* and 702*b* with his or her hands. Using sensors 702*a* and 702*b*, a weak electrical current is passed through the user's body to determine the amount of fat tissue. The weak electrical current is not felt by the user. A processor within monitor 700 calculates the user's body fat percentage using a bioelectrical impedance method for determining body fat. Muscles, blood vessels and bones are body tissues having a high water content that conduct electricity easily. Body fat, however, is tissue that has little electric conductivity. In an embodiment, the formula used to determine a user's percent body fat takes into account, for example, measured electric resistance and the height, weight, age and gender of the user.

FIG. 8 is a diagram of a heart rate/percent body fat monitor 800 according to an embodiment of the present invention. Heart rate/percent body fat monitor 800 represents one embodiment for the heart rate monitor 700 with built in sensors for detecting body fat described above. As shown in FIG. 8, heart rate/percent body fat monitor 800 includes a processor 802, memory 804, a heart rate sensor 806, body fat monitoring circuitry 808, a transceiver 812, and a battery 816.

Processor 802 is a conventional processor such as, for example, a microcontroller capable of implementing application programs stored in memory 804. Processor 802 is coupled to memory 804, heart rate sensor 806, body fat monitoring circuitry 808, and transceiver 812.

Memory 804 is used to store application program instructions and data. In an embodiment, memory 804 stores programs, for example, used to process data from heart rate sensor 806 and body fat monitoring circuitry 808. In an embodiment, memory 804 includes both read only memory and random access memory.

Heart rate sensor 806 is an electronic sensor that detects heart beats. This data is provided to processor 802 and used to determine a heart beat rate (e.g., number of beats per minute).

Body fat monitoring circuitry 808 is responsible, for example, for generating a weak electrical current that is passed through the user's body and for measuring electric resistance. The weak current is passed through the user's body by having the user grasp sensors 810*a* and 810*b* with his or her hands. Based on the determined electrical resistance, a formula is used to calculate the user's percent body fat. In an embodiment, the formula takes into account, for example, measured electric resistance and the height, weight, age and gender of the user.

Transceiver 812 is a low-power transceiver used to communicate with other components of sports electronic training system 100. In an embodiment, transceiver 812 operates in an unlicensed frequency band such as 2.4 GHz. Transceiver 812 is coupled to an antenna 814.

Battery 816 is used to provide power to operate the various components of heart rate/percent body fat monitor 800. Battery 816 can be either a rechargeable battery or a non-rechargeable battery.

In embodiments of the present invention, as described above, various components of the sports electronic training system periodically transmit data to a portable electronic processing device during a workout. In other embodiments, data collected and/or generated by components of the sports electronic training system such as, for example, a motion monitor and/or a heart rate monitor store the data during the entire workout and transmit the data only after the workout is completed (e.g., during a synchronization session). This is particularly beneficial for certain sports and for instances in which a user chooses not to carry or wear a portable electronic processing device.

FIG. 9 is a diagram that illustrates a portable electronic processing device 900 interacting with a computer 910. In an embodiment, portable electronic processing device 900 (e.g., a cell phone) communicates with computer 910 (e.g., a personal computer) using wireless communications. In another embodiment, portable electronic processing device 900 communicates with computer 910 using wire communications, for example, by placing portable electronic processing device 900 in a docking unit that is attached to computer 910 using a communications wire plugged into a communications port of computer 910.

As shown in FIG. 9, portable electronic processing device 900 has a button 902 that when pressed places portable electronic processing device 900 into a sports operating mode according to an embodiment of the present invention. The sports operating mode and it various features are discussed in more detail below, for example, with reference to FIGS. 13-33.

In an embodiment, data collected by portable electronic processing device 900, for example, when it is in sports operating mode, is uploaded to computer 910 for long term storage. This data can include, for example, workout data, photos, et cetera. This frees up memory space in portable electronic processing device 900 so that it can collect additional data without having to overwrite previously collected data. A program running on computer 910 can be used to retrieve and interact with the uploaded data. In addition, as explained in more detail below, for example, with reference to FIGS. 34-40, computer 910 can download data such as workout routines, music, running routes, et cetera, to portable electronic processing device 900.

FIG. 10 is a diagram that illustrates a portable electronic processing device 1000 interacting with computer 910. In an embodiment, portable electronic processing device 1000 (e.g., a sports watch) communicates with computer 910 using wireless communications. In another embodiment, portable electronic processing device 1000 communicates with computer 910 using wire communications. In this embodiment, portable electronic processing device 1000 interacts with computer 910 using, for example, a universal serial bus (USB) cable or other type cable.

In an embodiment, data collected by portable electronic processing device 1000 is uploaded to computer 910 for long term storage. This data can include, for example, workout data. This frees up memory space in portable electronic processing device 1000 so that it can collect additional data without having to overwrite previously collected data. A program running on computer 910 can be used to retrieve and interact with the uploaded data. In addition, computer 910 can download data to portable electronic processing device 1000.

FIG. 11A is a diagram of portable electronic processing device 900 interacting with a computer/web server 1100 according to an embodiment of the present invention. As shown in FIG. 11A, portable electronic processing device 900 interacts with computer 910, which interacts with computer/web server 1100 using network 1102. In an embodiment, network 1102 is the Internet. The interaction between portable electronic processing device 900 and computer 910, and the interaction between computer 910 and computer/web server 1100 may occur at different times. For example, in an embodiment, a user may use computer 910 to log-in to computer/web server 1100 and upload and/or download data such as, for example, new workout routines and/or running routes. Any information downloaded during the log-in session can be subsequently downloaded to portable electronic processing device 900 after the log-in session is complete (e.g., just before a user's next workout session).

In an embodiment, portable electronic processing device 900 interacts with computer/web server 1100 using, for example, a universal mobile telecommunications system (UMTS) connection or a global system for mobile communications (GSM) connection. In this embodiment, at the end of a workout (e.g., after a stop workout command is input), data collected during a workout is transmitted (e.g., either automatically or on command) to computer/web server 1100 without having to log-on to computer 910. The UMTS and/or GSM connection can be used both to upload and download information from computer/web server 1100.

FIG. 11B is a diagram of portable electronic processing device 1000 interacting with computer/web server 1100 according to an embodiment of the present invention. As shown in FIG. 11B, portable electronic processing device 1000 interacts with computer 910, which interacts with computer/web server 1100 using network 1102. The interaction between portable electronic processing device 1000 and computer 910, and the interaction between computer 910 and computer/web server 1100 may occur at different times.

FIG. 12 is a diagram of an example portable electronic processing device 1200 interacting with various exercise machines according to an embodiment of the present invention. As shown in FIG. 12, in an embodiment, such exercise machines can include an exercise bike 1202, a rowing machine 1204, a stair climber 1206, an elliptical machine 1208, and/or a tread mill 1210.

Portable electronic processing device 1200 interacts with various exercise machines, for example, by receiving and storing data collected by the exercise machines. The data can include, for example, the distance run on the tread mill, the distance traveled on the exercise bike, or the distance rowed on the rowing machine. The data can also include, for example, the time spent exercising and/or the calories burnt while exercising. In embodiments, the exercise machines includes motion monitors such as, for example, one or more motion monitors similar to the ones described herein. These motion monitors are used to monitor parts of the exercise machines (e.g., pedal of an exercise bike and steps of a stair climbing machine) that move.

The data collected by the various exercise machines can be provided to portable electronic processing device 1200 using wireless communications or wired communications (e.g., by placing portable electronic processing device 1200 in a docking unit). In an embodiment, exercise routines for each of the various exercise machines, which are tailored to an individual's fitness level, can be provided/downloaded from computer/web server 1100 and loaded into portable electronic processing device 1200. These routines can then be provided to a particular exercise machine prior to a workout.

As described herein, embodiments of the portable electronic processing devices of the present invention include a sports operating mode. An embodiment of the sports operating mode, as well as exemplary display views for interacting with a portable electronic processing device in sports operating mode, are described below with reference to FIGS. 13-33.

FIG. 13 is a diagram of an example portable electronic processing device 1300 that includes a sports operating mode having virtual trainer functionality according to an embodiment of the present invention. Portable electronic processing device 1300 includes a display 1302 and display navigation buttons 1304*a-d*. An enter or select button 1306 is located in the middle of display navigation buttons 1304*a-d*.

As shown in FIG. 13, portable electronic processing device 1300 has a main display view 1310. Main display view 1310 includes a plurality of icons that can be selected, for example, using navigation buttons 1304*a-d* and select button 1306. Selecting an icon activates the functionality associated with the selected icon.

Main display view 1310 is shown in FIG. 13 as having at least four icons: a phonebook icon 1312, a trainer icon 1314, a files icon 1316, and a music icon 1318. Other icons are also contemplated and are included in embodiments of the present invention. These other icons include, for example, a telephone call log icon, a voice mail icon, a web search engine icon, a camera icon, a clock/alarm icon, a games icon, et cetera.

In embodiments, main display view 1310, as well as other display views described herein, include optional soft keys, for example, at the bottom of the display view. These soft keys (e.g., Select and/or Back) can be used to implement the functionality noted. The soft keys are selected, for example, using keys or buttons of portable electronic processing device 1300.

In an embodiment, selecting trainer icon 1314 brings up a trainer display view 1320.

Trainer display view 1320 includes a banner display area 1322 and main display area 1324. Banner display area 1322 indicates the present routine being implemented by portable electronic processing device 1300 (e.g., the trainer routine). As shown in main display area 1324, the trainer routine includes several subroutines that can be selected, for example, using icons 1326*a-e*. In an embodiment, these subroutines include a workout routine, a music routine, a photos routine, a calendar routine, and a settings routine. Other routines are included in other embodiments. A start icon 1326*f* is used to start a workout.

In an embodiment, the icons of trainer display view 1320 rotate either clockwise or counter clockwise when a user presses a navigation button, and the icon at the bottom of the display view is the active icon. In another embodiment, the icons do not rotate in response to user inputs.

FIG. 14A is a diagram that illustrates workout features of a sports electronic training system according to an embodiment of the present invention. The workout features are selected, for example, by selecting the workout icon 1326*a* of display view 1320.

In an embodiment, selecting workout icon 1326*a* brings up a workout display view 1402. Display view 1402 presents to a user a plurality of previously created workouts such as, for example, a morning run workout, a lunch run workout, et cetera. Display view 1402 also presents a create run option in case the user wants to create a workout not available for selection. A checkmark 1404 indicates the selected or default workout. An arrow 1406 is used to scroll through the various options when there are more options than can be displayed at one time.

Selecting the morning run workout brings up a display view 1410. Display view 1410 displays the details of the morning run workout and enables a user, for example, to select another workout or to edit the time and/or intensity of the selected workout.

In an embodiment, the name of a presently selected workout (e.g., "morning run") appears in a workout name field 1412 of display view 1410. If the user wishes to select another workout, the user can do this by using arrows associated with field 1412 to scroll through various other workouts until a desired workout appears in field 1412. Once a desired workout appears in field 1412, the user can view and/or edit the time of the workout and/or the endurance of the workout. A user changes the time of the workout by modifying the time shown in a time field 1414. The time can be varied by typing in a desired time or by scrolling through various time options using arrows associated with time field 1414. A user changes the intensity of the workout be varying the intensity displayed in an intensity field 1416. The intensity can be changed for example using arrows associated with intensity field 1416. In an embodiment, selectable options for the various fields of display view 1410 are presented using dropdown box rather than scroll arrows.

In an embodiment, display view 1410 includes a trainer checkbox 1418. Checking this box enables audio feedback to be provided to a user during a workout. Removing the check from trainer checkbox 1418 disables the audio feedback.

Referring to FIG. 14A, at the bottom of display view 1410 is a display area 1420 that enables a user to select another subroutine of the trainer routine. As shown in FIG. 14A, the subroutine shown in display area 1420 is the music subroutine. If another routine is desired, the arrows in display area 1420 can be used to scroll through the other available subroutines such as, for example, the photos subroutine, the calendar subroutine and the settings subroutine.

Selecting the music icon in display area 1420 brings up a music display view 1430. Display view 1430 is used to select the music to be played during a workout. Playable music includes, for example, music stored in one or more play lists or radio music.

A table that spans FIGS. 14B and 14C illustrates example audio feedback provided to a user during a workout. The table illustrates example feedback that is appropriate, for example, for a 60 minute workout/run at a strength (e.g., yellow) level of intensity. As described herein, workouts can be performed at different intensity levels, and in an embodiment, these levels are associated with various colors to facilitate providing feedback to a user. In an embodiment, an easy workout is associated with a color such as green or blue, an intermediate intensity workout is associated with yellow, and a hard workout is associated with red. Other colors can also be used. One benefit of using different colors to represent different workout intensities is that colored bars can be used to display a workout. Accordingly, a bar used to represent a workout having different intensity periods would be displayed as a bar having different colored segments.

In embodiments, the virtual trainer functionality of the present invention can influence a workout program, session or routine in real time. For example, in a situation in which a heart rate monitor is being used to monitor an individual's heart rate during a workout, the virtual trainer will monitor the heart rate data for signs of overtraining and when an overtraining situation is identified, the virtual trainer will change the workout, for example, to an easier run. In embodiments of the present invention, data from other sensors (e.g., a hydration sensor, a temperature sensor, etc.) can also be monitored for signs of overtraining, and when overtraining is detected, the virtual trainer will modify the work appropriately.

FIG. 15A is a diagram that illustrates first example customizable parameter displays for a sports electronic training system according to an embodiment of the present invention. As illustrated by FIG. 15A, a user can select what performance parameters are displayed and/or provided to the user as feedback during a workout.

In operation, once a user starts a workout, the trainer routine provides feedback to the user. This feedback can be visual feedback, for example, displayed on display 1302 of portable electronic processing device 1300 and/or audio feedback provided to the user using headphone plugged into an audio jack of portable electronic processing device 1300. The visual feedback can be continuously displayed and updated during the workout. The audio feedback is provided, for example, when a user taps portable electronic processing device 1300 twice.

As shown in FIG. 15A, a first example display 1502 shows an elapsed time since the start of the workout (e.g., 7 minutes and 42 seconds), a heart rate (e.g., 184 beats per minute), and a total distance run since the beginning of the workout (e.g., 1.6 km). As shown in example display 1504, if the user is not wearing a motion sensor on a shoe, the feedback display will not show a total distance run. Instead, it may display, for example, the text "Not Found" in place of a total distance run to indicate to the user that portable electronic processing device 1300 is not in communication with a motion sensor. As shown in example display 1506, if the user is not wearing a heart rate monitor, the feedback display will not show a total number of heart beats per minute value. Instead, it may display the text "Not Found" in place of a heart rate to indicate to the user that portable electronic processing device 1300 is not in communication with a heart rate monitor.

In embodiments, as illustrated by example display 1508, a user can change the feedback that is displayed, for example, by selecting a display icon and using arrow keys 1510 associated with the selected display icon to scroll through various optional display parameters and pick a desired parameter for display. In one embodiment, the parameters available for display include time, heart rate distance, calories, pace and/or stride rate. In other embodiments, other parameters are available.

FIG. 15B is a diagram that illustrates second example customizable parameter displays for a sports electronic training system according to an embodiment of the present invention. As illustrated by FIG. 15B, the second example parameter displays include in the top one-third of the display an elapsed time value. In the bottom two-thirds of the display area, a workout performance parameter goal is displayed such as, for example, a stride rate goal, a pace goal, a heart rate goal, or a distance goal. In an embodiment, a user can cycle through which goal is displayed by pressing a button on the portable electronic processing device.

Example display 1522 displays for a user elapsed time and a stride rate performance parameter goal. As illustrated in FIG. 15B, the stride rate goal for the depicted example workout is 180 steps per minute. A runner can determine whether he or she is meeting the workout goal by monitoring three indicators 1524, 1526, and 1528. If the runner is meeting the stride rate goal (e.g., the runner is meeting the goal within a selected number of steps per minute) during a workout, the middle indicator 1526 is illuminated. If the runner is exceeding the stride rate goal by more than a selected number of steps per minute (e.g., 5 steps per minute), the top indicator 1524 is illuminated as an indication to the runner to decrease the stride rate. If the runner is below the stride rate goal by more than a selected number of steps per minute (e.g., 5 steps per minute), the bottom indicator 1528 is illuminated as an indication to the runner to increase the stride rate.

In one embodiment, a user is provided with stride rate training feedback in the form of beeps in headphones worn by the user. The beeps correspond, for example, to the stride rate goal, and the user adjusts his or her stride rate to match the beeps. The beeps can be provided, for example, only when a change in stride rate is required (e.g., when the runner is running below or above a particular stride rate goal).

Example display 1530 displays for a user elapsed time and a workout pace goal. The pace goal for the depicted example workout is 7 minute and 30 seconds per mile. A runner can determine whether he or she is meeting the workout goal by monitoring the three indicators 1524, 1526, and 1528. As above, if the runner is meeting the pace goal during a workout, the middle indicator 1526 is illuminated. If the runner is exceeding the pace goal, the top indicator 1524 is illuminated as an indication to the runner to decrease the pace. If the runner is below the pace goal, the bottom indicator 1528 is illuminated as an indication to the runner to increase the pace.

Example display 1532 displays for a user elapsed time and a workout heart rate goal. The heart rate goal for the depicted example workout is 175 beats per minute. A runner can determine whether he or she is meeting the workout goal by monitoring the three indicators 1524, 1526, and 1528. As above, if the runner is meeting the heart rate goal during a workout, the middle indicator 1526 is illuminated. If the runner is exceeding the heart rate goal, the top indicator 1524 is illuminated. If the runner is below the heart rate goal, the bottom indicator 1528 is illuminated.

Example display 1534 displays for a user elapsed time and a workout distance goal. The elapsed time is depicted in the top one-third of display 1534. The distance goal is depicted in the bottom two-thirds of display 1534. In an embodiment, the distance goal is shown as a pie chart, which is filled-in in proportion to how much of the distance goal has been achieved. For example, if the runner has completed 25% of the distance goal, than one-quarter of the pie chart is filled-in as shown in FIG. 15B. A similar display can be used to depict completion, for example, of a calories goal.

FIG. 15C is a diagram that illustrates third example customizable parameter displays for a sports electronic training system according to an embodiment of the present invention. As illustrated by FIG. 15C, the third example parameter displays include in the top one-third of the display an elapsed time value. In the bottom two-thirds of the display area, a workout performance parameter goal is displayed such as, for example, a stride rate goal, a pace goal, a heart rate goal, or a calorie goal. In an embodiment, a user can cycle through which goal is displayed by pressing a button on the portable electronic processing device.

Example display 1542 displays for a user elapsed time and a stride rate performance parameter goal. As illustrated in FIG. 15C, the stride rate goal for the depicted example workout is 180 steps per minute. A runner can determine whether he or she is meeting the workout goal by monitoring two indicators 1544 and 1546. If the runner is exceeding the stride rate goal by more than a selected number of steps per minute (e.g., 5 steps per minute), the top indicator 1544 is illuminated as an indication to the runner to decrease the stride rate. If the runner is below the stride rate goal by more than a selected number of steps per minute (e.g., 5 steps per minute), the bottom indicator 1546 is illuminated as an indication to the runner to increase the stride rate. If the runner is meeting the stride rate goal (e.g., the runner is meeting the goal within a selected number of steps per minute) during a workout, neither indicator is illuminated.

Example display 1548 displays for a user elapsed time and a workout pace goal. The pace goal for the depicted example workout is 7 minute and 30 seconds per mile. A runner can determine whether he or she is meeting the workout goal by monitoring the two indicators 1544 and 1546 next to the pace goal. As above, if the runner is exceeding the pace goal, the top indicator 1544 is illuminated as an indication to the runner to decrease the pace. If the runner is below the pace goal, the bottom indicator 1546 is illuminated as an indication to the runner to increase the pace.

Example display 1550 displays for a user elapsed time and a workout heart rate goal. The heart rate goal for the depicted example workout is 175 beats per minute. A runner can determine whether he or she is meeting the workout goal by monitoring the two indicators 1544 and 1546. As above, if the runner is exceeding the heart rate goal, the top indicator 1544 is illuminated. If the runner is below the heart rate goal, the bottom indicator 1546 is illuminated.

Example display 1552 displays for a user elapsed time and a workout calories goal. The elapsed time is depicted in the top one-third of display 1552. The calories goal is depicted in the bottom two-thirds of display 1552. In an embodiment, the calories goal is shown as a pie chart, which is filled-in in proportion to how many of the desired calories have been burned so far during the workout. For example, if the runner has burned calories equal to 25% of the calories goal, than one-quarter of the pie chart is filled-in as shown in FIG. 15C. A similar display can be used to depict completion, for example, of a distance goal.

FIG. 15D is a diagram that illustrates fourth example customizable parameter displays for a sports electronic training system according to an embodiment of the present invention. As illustrated by FIG. 15D, the fourth example parameter displays include in the top one-third of the display an elapsed time value. In the bottom two-thirds of the display area, a workout performance parameter goal is displayed such as, for example, a stride rate goal, a pace goal, a heart rate goal, or a distance goal. In an embodiment, a user can cycle through which goal is displayed by pressing a button on the portable electronic processing device.

Example display 1562 displays for a user elapsed time and whether a workout stride rate performance parameter goal is being met. As illustrated in FIG. 15D, a runner can determine whether he or she is meeting the workout goal by monitoring three indicators 1564, 1566, and 1568. If the runner is meeting the stride rate goal (e.g., the runner is meeting the goal within a selected number of steps per minute) during a workout, the middle indicator 1566 is illuminated. If the runner is exceeding the stride rate goal by more than a selected number of steps per minute (e.g., 5 steps per minute), the right indicator 1568 is illuminated as an indication to the runner to decrease the stride rate. If the runner is below the stride rate goal by more than a selected number of steps per minute (e.g., 5 steps per minute), the left indicator 1564 is illuminated as an indication to the runner to increase the stride rate.

Example display 1570 displays for a user elapsed time and a workout pace goal. A runner can determine whether he or she is meeting the workout pace goal by monitoring the three indicators 1564, 1566, and 1568 in a manner similar to that described above.

Example display 1572 displays for a user elapsed time and a workout heart rate goal. A runner can determine whether he or she is meeting the workout heart rate goal by monitoring the three indicators 1564, 1566, and 1588. As above, if the runner is meeting the heart rate goal during a workout, the middle indicator 1566 is illuminated. If the runner is exceeding the heart rate goal, the right indicator 1568 is illuminated. If the runner is below the heart rate goal, the left indicator 1564 is illuminated.

Example display 1574 displays for a user elapsed time and a workout distance goal. The elapsed time is depicted in the top one-third of display 1574. The distance goal is depicted in the bottom two-thirds of display 1574. In an embodiment, the distance goal is shown as a pie chart, which is filled-in in proportion to how much of the distance goal has been achieved. For example, if the runner has completed 25% of the distance goal, than one-quarter of the pie chart is filled-in as shown in FIG. 15D. A similar display can be used to depict completion, for example, of a calories goal.

In one embodiment, a sports training system according to the present invention includes glasses. The glasses have color indications located within the field of view of the wearer that provide feedback to the wearer (e.g., a runner) about performance. For example, in one embodiment, three lights indicate zones of performance (e.g., on target performance, below target performance, and above target performance). In another embodiment, two colors indicate performance (e.g., below target performance and above target performance—no indicator light is used to indicate on target performance). The performance being monitored can relate, for example, to heart rate, stride rate, et cetera.

In an embodiment, a sports training system according to the present invention includes glasses that display text and/or graphical information (e.g., other than color indications) within the field of view of the wearer. This information provides feedback to the wearer, for example, about performance and/or navigation. In one embodiment, the graphical information includes, for example, navigation arrows that indicate to a runner which way the runner should run.

FIGS. 15E-F illustrate two tables (Table 1A and Table 1B) that can be used to calculate the number of calories burned (in kcal/min) while exercising according to an embodiment of the present invention. As shown in the tables, the calories burned is a function of whether a person is walking or running, how fast the person is walking or running, and the person's body weight. In an embodiment, these tables are used as look-up tables implemented by software running on a portable electronic processing device according to the present invention. Other tables can also be used. Thus, the present invention is not limited to using these tables.

FIG. 15G illustrates a Table 2 that can be used to calculate the number of calories burned while exercising according to another embodiment of the present invention. In this embodiment, the calories burned calculation is based on an individual's weight and metabolic equivalent units (METS) (e.g., the number of calories used per minute based on activity). In this embodiment, the calories burned per hour, for example, by an individual are equal to the individual's weight in kilograms multiplied by the appropriate METS valued from Table 2.

As shown in Table 2, in an embodiment, the METS value used to calculate calories burned is selected, for example, using an individual's fitness level (e.g., beginner, intermediate, or advanced) and/or a workout intensity (e.g., energy, endurance, strength, power, or leg strength) or percent heart rate. The criteria used to select a METS value in a particular embodiment may vary depending on how the calorie calculator is implement, for example, in software running on a portable electronic processing device. In an embodiment, if an individual has taken a fitness test and is working out using web created workouts, for example, the calories burned are calculated based on fitness level and workout intensity. If the individual creates a custom workout using the portable electronic processing device, the calorie calculator automatically defaults to using advanced heart rate ranges and METS values are selected independently of the individual's fitness level.

FIGS. 16-18 are diagrams that illustrate one method for creating a workout using a sports electronic training system according to an embodiment of the present invention. As shown in FIG. 16, the method begins by selecting the create run entry of workout display view 1402. In an embodiment, selecting the create run entry brings up a goal display view 1602. Display view 1602 list several workout goals such as, for example, time, distance, pace, calories, stride rate, et cetera. If a user selects a time goal, the selection brings up a time display view 1604 that list various times. A user can select one of the listed times, or the user can enter a time. In an embodiment, after the user selects or enters a time, the user is presented with an intensity display view 1606 that lists various workout intensity options. As shown in FIG. 16, in an embodiment, the intensity workout options are energy, endurance, strength, power, and none. Energy is the least strenuous intensity option and power is the most strenuous intensity option.

As shown in FIG. 17, if the user selects a distance goal at display view 1602, a display view 1702 is presented to the user, which lists various distances for selection. The user can select one of the presented distances or enter another distance.

As shown in FIG. 18, if the user selects a pace goal at display view 1602, a display view 1802 is presented to the user, which includes a units field 1804 and a pace field 1806. The user can select a desired unit (e.g., min/km) and a desired pace (e.g., 4:30) using arrows associated with each field. The user can also enter a desired pace. In an embodiment, as shown in FIG. 18, after the user has made all of the selections for a workout, the user is presented with a soft key save option in display area 1808.

In an embodiment, display views similar to the ones described herein are provided to the user if the user selects a calories goal or a stride rate goal. The edit run entry of display view 1402 brings up a list of previously created workouts, which the user can select and edit.

FIG. 19 is a diagram that illustrates music features of a sports electronic training system according to an embodiment of the present invention. In an embodiment, if a user selects music icon 1326b at trainer display view 1320, a music display view 1430 appears. Display view 1430 lists a plurality of music options that the user can select. These options include, for example, tempo songs, a radio, music play lists, motivational songs, recently played songs, most played songs, an artists list, an albums list, et cetera.

If the user selects the tempo entry at display view 1430, a display view 1902 appears. Display view 1902 lists several groups of songs having a tempo matched to a particular workout intensity. These intensities are energy, endurance, strength, and power. The user can also make an automatic selection, which will change the tempo of the music being played, for example, to match a user's stride rate, heart rate, or an intensity index based on a combination of these and/or other performance parameters.

If the user selects the radio entry at display view 1430, a display view 1904 appears. Display view 1904 includes a radio reception indication bar 1906, a frequency tuning field 1908, and a display area 1910 that lists recently played radio frequencies. In an embodiment, the user tunes the radio to a desired frequency by entering a desired frequency, by using tuning arrows associated with frequency tuning field 1908, or by highlighting and selecting a frequency in display area 1910.

In embodiments, the radio is both an AM radio and an FM radio. Either the AM or FM radio is selected using a soft key located in a display area 1912.

If the user selects the play lists entry at display view 1430, a display view 1920 appears. At display view 1920, the user can select a previously compiled play list from among a variety of play lists. If there are more play lists than can be shown on the display, an arrow is used to scroll through the various play lists.

Selecting one of the other music options at display view 1430 brings up other display views, similar to the ones described herein, which enables the user to make appropriate music selections.

FIG. 20 is a diagram that illustrates photo features of a sports electronic training system according to an embodiment of the present invention. If a user selects the photos icon 1326c at display view 1320, a photos display view 2002 appears. Display view 2002 presents a list of photos taken with a camera that is integrated, for example, into portable electronic processing device 1300 (e.g., a cell phone camera). The list of photos includes a name for each photo and a date that each photo was taken.

In an embodiment, the user selects a particular photo 2004 by highlighting the associated photo entry in display view 2002, for example, using navigation buttons and pressing an enter or select button. The selected photo 2004 is then displayed along with its name and an options soft key in an area 2005 of the display.

Selecting the options soft key in display area 2005 brings up a display view 2006. Display view 2006 lists a variety of things that the user can do with photo 2004. For example, the user can display a full screen view of photo 2004, the user can assign photo 2004 to a particular workout, or the user can delete photo 2004. In embodiments, other options are also available. These options can include, for example, changing the zoom level of the photo and/or performing other image processing operations.

If the user selects the assign to a workout option at display view 2006, a display view 2008 appears. Display view 2008 lists various workouts stored, for example, in a memory of portable electronic processing device 1300. To assign photo 2004 to one of the listed workouts, the user scrolls through the list of workouts and selects a particular workout. Selecting the workout assigns photo 2004 to the workout. Once the photo is assigned to the workout, an icon appears next to the name of the workout to indicate that there is at least one photo associated with the workout.

FIG. 21 is a diagram that illustrates calendar features of a sports electronic training system according to an embodiment of the present invention. As shown in FIG. 21, if a user selects the calendar icon 1326d at display view 1320, a calendar display view 2102 appears. Calendar display view 2102 presents the user with a view of a calendar and a date field 2104 at the top of the calendar. The user can select a particular date, for example, by using arrows associated with date field 2104 to change the displayed date, or by highlighting a particular date on the calendar using navigation buttons and pressing on a select or enter button.

Selecting a particular date at display view 2102 brings up an options display view 2106. In an embodiment, display view 2106 permits a user, for example, to view workout(s) associated with the selected date, assign a workout to the selected date, or delete a saved workout for the selected date. In an embodiment, the user can also retrieve a list of workouts at display view 2106. Selecting the workout list option at display view 2106 brings up a display view 2108, which lists workouts saved in a memory of the portable electronic processing device.

In an embodiment, as shown in FIG. 22, if the user selects the assign workout option at display view 2106, a display view 2202 appears. Display view 2202 includes a field 2204 that lists a workout name, a repeat checkbox 2206, days of the week checkboxes 2208, and a repeat until date field 2210.

Display view 2202 is used to assign particular workouts to future dates. For example, to assign a workout titled lunch run, a user uses the arrows associated with field 2204 to scroll through various workouts until lunch run appears in field 2204. If the selected workout is to be assigned to multiple days, the repeat checkbox 2206 is check. This will cause the selected workout to be assigned to the days of the week checked using checkboxes 2208, for example, from the date shown in display view 2106 until the date entered into repeat until date field 2210.

If the user wishes to see the goals of the workout shown in field 2204 at display view 2202, the user can press an enter or select button to bring up display view 2220. Display view 2220 displays the name of the workout in a field 2222, and the goals of the workout in a field 2224 and a field 2226. As shown in FIG. 22, the goals for the lunch run are to run for 30 minutes at an endurance intensity. Arrows associated with fields 2224 and 2226 can be used to change the goals for the workout.

In an embodiment, the user can use arrows associated with field 2222 to scroll through other workouts and see the goals for the workouts. For example, if the user uses the arrows associated with field 2222 to scroll to an intervals workout, display view 2230 appears. Display view 2230 includes fields 2232, 2234, 2236 and a visual indicator of the workout 2238. Field 2232 displays the name of the selected workout. Fields 2234 and 2236 display the goals of the workout. For example, as shown in FIG. 22, the goals for the intervals workout are to run 5 km at two different workout intensities. The two intensities are alternated every minute for the entire 5 km. Both the distance goal and the interval times can be changed at display view 2230 using, for example, the arrows associated with fields 2234 and 2236.

As shown in FIG. 23, if a user selects the view workout option at display view 2106, a display view 2302 appears. Display view 2302 shows the workout assigned to a selected date and, if the workout has been completed, a soft key in display area 2303 that can be used to view the results of the workout.

Selecting the view results soft key at display view 2302 brings up a display view 2304. Display view 2304 displays the results for a selected workout (e.g., a workout completed on 3 Jun. 2006). In an embodiment, the workout results include the duration of the workout, the distance traveled during the workout, an average heart rate for the workout, a maximum heart rate for the workout, an average pace for the workout, the calories burnt during the workout, and an average stride rate for the workout. Other values can also be displayed, and in an embodiment are user selectable.

FIG. 24 is a diagram that illustrates the selection of settings for a portable electronic processing device according to an embodiment of the present invention. As shown in FIG. 24, if a user selects settings icon 1326*e* at display view 1320, a settings display view 2402 appears. Settings display view 2402 includes several options that a user can select, for example, by using navigation buttons to highlight a desired option and then pressing an enter or select button. When the units option 2404 is selected, an units display view 2406 appears.

Units display view 2406 includes a distance field 2408 and a weight field 2410. In an embodiment, the selectable distance units includes miles and kilometers. The desired distance unit can be selected using arrows associated with distance field 2408. The selectable weight units include pounds and kilograms. The desired weight unit can be selected using arrows associated with weight field 2410.

FIG. 25 is a diagram that illustrates one method for inputting and updating personal data for a sports electronic training system according to an embodiment of the present invention. As shown in FIG. 25, if a user selects the personal data option at display view 2402, a personal data display view 2502 appears. In an embodiment, personal data display view 2502 includes the following data fields: a gender field 2504, a date of birth field 2506, a weight field 2508, a rest heart rate field 2510, and a maximum heart rate field 2512. The user enters data into each of these fields as appropriate.

In an embodiment, some of the fields are populated automatically, for example, by a heart rate monitor in communications with the portable electronic processing device during an assessment session or workout. A soft key in display area 2514 can be used to start the assessment session. In one embodiment, the data in weight field 2508 is communicated to the portable electronic processing device by a weight scale in wireless communications with the portable electronic processing device.

In embodiments, the personal data display view includes additional data fields such as, for example, a weight field, a height field, and/or a body mass index (BMI) field or a percent body fat field. In an embodiment, a BMI value or percent body fat value is generated for each workout and stored together with other workout information. This allows a user, for example, to display and track BMI or percent body fat values and work towards a BMI or percent body fat goal.

In an embodiment, a percent body fat value is generated at the beginning of each workout using heart rate monitor 700. The percent body fat value can be obtained by having the user hold heart rate monitor 700 before putting it on to obtain a hand-to-hand impedance measurement. In another embodiment, the percent body fat value is obtain while the user is wearing heart rate monitor 700. In still another embodiment, the percent body value is generated using a foot-to-foot impedance measurement, which can be obtained, for example, by having the user stand on the sensors of heart rate monitor 700, a weight scale having built in sensors that can measure foot-to-foot impedance, or some other object such as, for example, a door mat having sensors that can measure foot-to-foot impedance and/or a persons weight. In one embodiment, the weight, BMI and/or percent body fat fields of the personal data display view are automatically updated with information from the weight scale or other object.

In embodiments, the personal data stored in the portable electronic processing device is password protected. Thus, when a user selects the personal data option at display view 2402, a display view 2520 appears. Display view 2520 includes a password field 2522. In order to gain assess to display view 2502, a user must enter a proper password into password field 2522.

FIG. 26 is a diagram that illustrates one method for assessing a fitness level with a sports electronic training system according to an embodiment of the present invention. The assessment begins, for example, when a user of a portable electronic processing device, such as device 1300, selects an assess fitness key.

As shown in FIG. 26, in an embodiment, a user is presented with a display view 2602 at the beginning of a new fitness assessment. Display view 2602 displays a saved fitness number and an associated fitness level for the user, if they exist. Display view 2602 also displays a prompt to start the new fitness assessment. When the user selects the start new assessment option, a display view 2604 appears.

Display view 2604 instructs the user to complete, for example, 1.6 km as quickly as possible and to tap the portable electronic processing device twice after completing the 1.6 km. In an embodiment, these directions are also provided to the user orally using a speaker or headphones attached to a headphone jack of the portable electronic processing device.

At the end of the new assessment, data relating to the assessment are presented on a display view 2606. The presented data include personal data for the user such as the user's gender, age and weight. This data is typically obtained from the user using a personal data display view 2502. Data collected during the assessment such as, for example, the time it took the user to complete 1.6 km, the user's maximum heart rate during the assessment, and the user's heart rate 1 minute after completing the 1.6 km are also shown. The data is used to calculate a new fitness number and fitness level for the user. The new fitness number and fitness level are included in display view 2606. Soft keys at the bottom of display view 2606 can be used to either save the data associated with the new assessment or to cancel the data without saving it.

In an embodiment, the fitness number (F) for a male user is calculated using equation 5 below:

$$F=132.853-0.0769W-0.3877A+6.315-3.2649T-0.1565(MHR/1.065)-10+0.1(MHR/1.065-HR1) \quad \text{EQ. 5}$$

where W equals weight in pounds; A equals age in years; T equals time in minutes; MHR equals maximum heart rate during assessment in beats per minute; and HR1 equals heart rate 1 minute after the user completed the 1.6 km in beats per minute.

In an embodiment, the fitness number (F) for a female user is calculated using equation 6 below:

$$F=132.853-0.0769W-0.3877A-3.2649T-0.1565(MHR/1.065)-15+0.1(MHR/1.065-HR1) \quad \text{EQ. 6}$$

where W equals weight in pounds; A equals age in years; T equals time in minutes; MHR equals maximum heart rate during assessment in beats per minute; and HR1 equals heart rate 1 minute after the user completed the 1.6 km in beats per minute.

In one embodiment, the present invention analyzes each workout completed by the user and automatically uses the workout data to update the user's fitness level and fitness number rather than wait for the user to elect to perform a new fitness assessment.

FIG. 27 is a diagram of an example Fitness Level table used to determine a fitness level according to an embodiment of the present invention. To determine a fitness level, one first determines whether the person for whom the fitness level is being determined is a male or a female. Next, one looks up the calculated fitness number for the individual in the row corresponding to the age of the individual. The fitness level is then read from the column in which the fitness number is located. For example, using the Fitness Level table, a 25 year old male having a calculated fitness number of 57 is assessed as having a fitness level of intermediate (Int) 2. A 37 year old female having a calculated fitness number of 30 is assessed as having a fitness level of beginner (Begin) 1.

In one embodiment, a fitness level for an individual is determined by asking the individual a series of questions. These questions are as follows:
1. Do you run, exercise or play sports on a regular basis?
2. Do you walk a total of at least 30 minutes a day?
3. How many days a week do you run, exercise or play sports?
4. About how long do you run, exercise or play sports on each day?

Based on the answers to these questions, a fitness level is assigned to the individual.

For example, in an embodiment, a user is asked question 1. If the user answers no to question 1, the user is asked question 2. If the user answers no to question 1 and no to question 2, the user is assessed to have a fitness level of beginner 1. If the user answers no to question 1 and yes to question 2, the user is assessed to have a fitness level of beginner 2.

In an embodiment, if a user answer yes to question 1, the user is asked questions 3 and 4. The responses to questions 3 and 4 are used to determine a fitness level for the user. For example, if the user indicates that he exercises three days per week, for about 45 minutes each day, these two responses would be combined to determine that the user exercise for a total of 135 minutes per week. The total time spent running, exercising or playing sports each week is then compared to the times in the fitness table below to determine a fitness level for the individual. For the example of 135 minutes per week, the user would be assessed a fitness level of intermediate 3.

| Fitness Level Assessment Table | | | | | | |
|---|---|---|---|---|---|---|
| Fitness Level | Begin 1 | Begin 2 | Int 1 | Int 2 | Int 3 | Adv |
| Minutes spent running, exercising or playing sports per week | ≤40 | ≤60 | ≤100 | ≤130 | ≤160 | >160 |

As described herein, in embodiments of the present invention, the assessed fitness level of an individual is used to develop a workout/exercise plan tailored to the fitness level of the individual and aimed at assisting the individual to achieve one or more specific fitness or exercise goals.

FIG. 28 is a diagram that illustrates component identification features of a sports electronic training system according to an embodiment of the present invention. As shown in FIG. 28, if a user selects the components option at display view 2402, a components display view 2802 appears.

Display view 2802 includes a motion monitor field 2804, a heart rate monitor field 2806, and a watch field 2808. These fields are used to store the unique serial number identification values transmitted by components of a sports electronic training system according to the present invention. The stored serial number identification values are used by the portable electronic processing device to determine whether a received message is to be stored and processed or to be ignored. The display view can also include other fields that are used to store serial number identification values transmitted by other components of the sports electronic training system described herein.

As described above, in an embodiment, each component of sports electronic training system 100 communicates with a portable electronic processing device such as, for example, device 300 by periodically transmitting a message to the device that includes both a device type identification value and a unique serial number identification value. The device type identification value identifies a particular component, for example, as a motion monitor, a heart rate monitor or a watch. Knowing the device type enables the portable electronic processing device, for example, to decode message data. Accordingly, the portable electronic processing device knows to decode data from a heart rate monitor as heart beats per minute and to decode data from a motion monitor, for example, as average velocity, distance traveled, pace, et cetera. The unique serial number identification value transmitted by a component enables the portable electronic processing device to identify whether a received message is from a component belonging to the same WPAN as the portable electronic processing device or whether the received message belongs, for example, to a WPAN of another nearby runner.

As shown in FIG. 28, the stored serial number identification value for the motion monitor is 124425. This value can be manually entered by a user, or it can be automatically detected and stored by the portable electronic processing device. In FIG. 28, field 2806 is shown displaying the text searching to indicate that the portable electronic processing device is in the process of trying to locate a nearby heart rate monitor and associate it to the WPAN. If a heart rate monitor is not found within a particular period of time, the user is presented with a display view 2810. This display view queries the user as to whether the search for a heart rate monitor should be repeated or discontinued. The user input to the query is made by using soft keys located in display area 2812.

Field 2808 of display view 2802 displays the text none to indicate that the portable electronic processing device should not look for a watch nor associate with a watch. A user might enter none in field 2808, for example, if the user has not yet purchased a sports watch. This would enable the portable electronic processing device to forgo trying to associate with a watch each time the portable electronic processing device is switched to sport operating mode.

FIG. 29 is a diagram that illustrates setting telephone features of a sports electronic training system according to an embodiment of the present invention. In embodiments of the present invention, in which the portable electronic processing device is a mobile phone, selecting the telephone option at display view 2402 brings up display view 2902. Display view 2902 includes two fields 2904 and 2906. If a user wishes to receive telephone calls while the mobile phone is in sports operating mode, the user enters yes in field 2904. If the user does not wish to receive telephone calls, the user enters no in field 2904. If the user wishes to receive telephone calls when the mobile phone is in sports operating mode, field 2906 is used to set the ring tone for the mobile phone. This ring tone is the ring tone for the mobile phone when the mobile phone is in sports operating mode.

FIGS. 30-32 are diagrams that illustrate setting virtual trainer features of a sports electronic training system according to an embodiment of the present invention. As shown in FIG. 30, if a user selects the trainer option at display view 2402, a trainer display view 3002 appears.

Display view 3002 includes three options: a voice option, a feedback interval option, and a feedback content option. Selecting the voice option brings up a display view 3004. In an embodiment, display view 3004 includes a plurality of checkboxes that are used to select a language for the virtual trainer. If a user selects the checkbox for English, for example, the virtual trainer will provide feedback to a user in English. After a language selection is made, a user is presented with a display view 3006. Display view 3006 is used to select, for example, the voice quality for the virtual trainer. In an embodiment, a user has a choice of a male voice, a female voice, and the voices, for example, of famous people such as sports stars. In an embodiment, other voices (e.g., voices of famous actors, etc.) can be downloaded from the computer/web server and used for the virtual trainer.

If a user selects the feedback interval option at display view 3002, a display view 3102 appears, as illustrated in FIG. 31. Display view 3102 is used to select when audio feedback is provided to a user. In embodiments, the available intervals include, for example, between songs, at every milestone, and no feedback. If the user selects the option to receive feedback at every milestone, the user is presented with display views that permit the user to select miles stones. Display view 3104, for example, permits a user to select distance milestones. Other display views permit the user to select other milestones such as time milestones. In an embodiment, a user can receive feedback at anytime, for example, by tapping the portable electronic processing device a selected number of times, or by pressing a switch on the headphone cords, or by pressing a blind access button on the portable electronic processing device. In an embodiment, feedback is requested by voice control using, for example, a microphone built into the portable electronic processing device. In one embodiment, each time the user states feedback, or another word or phrase, immediate audible feedback is provided to the user.

If a user selects the feedback content option at display view 3002, a display view 3202 appears, as illustrated in FIG. 32. Display view 3202 is used to select what feedback is provided to the user at each feedback interval. In an embodiment, display view 3202 includes a plurality of checkboxes, wherein each checkbox is associated with a particular performance parameter. The user selects the feedback content by marking one or more of the available checkboxes.

A table that illustrates example audio feedback provided to a user in accordance with an embodiment of the present invention is provided in FIGS. 14B and 14C. In embodiments, the feedback examples provided in the table are modified to provide feedback in accordance with the feedback content selected by a user, for example, using display view 3202.

In one embodiment, the virtual trainer analyzes the effectiveness of feedback provided to a user (e.g., whether the feedback is motivating a runner to improve performance) and is able to modify its personality (e.g., one or more of the trainer settings described herein) over time to provide more effective feedback to the user. This self-adapting feature of the present invention enables the virtual trainer to maximize the effectiveness of training feedback provided by the virtual trainer.

As shown in FIG. 33, in an embodiment, the portable electronic processing device can operate as a pedometer. If a user selects the pedometer option at display view 2402, a pedometer display view 3302 appears. The information for the pedometer can come, for example, from a motion monitor 104 or an accelerometer or other sensor integrated into the portable electronic processing device.

In an embodiment, display view 3302 includes a checkbox that permits a user to select whether a step counter is to be displayed on the portable electronic processing device's wallpaper or main display view. Display view 3302 also includes a step counter field 3308 and a step counter reset time field 3306. The reset time entered in field 3306 is the time at which the step counter will be reset to zero. In an embodiment, the reset time can be manually entered by a user, or it can be entered, for example, using arrows associated with field 3306.

Display view 3310 is an example main display view for one embodiment of a portable electronic processing device according to the present invention (e.g., a mobile phone embodiment). Display view 3310 is shown displaying a pedometer step counter field 3308.

In an embodiment of the present invention, an accelerometer mounted, for example, on a wristband or in a watch is used to measure daily activity level for an individual. The wristband or watchband changes color to indicate to the wearer whether the wearer is meeting an activity goal for day. In an embodiment, the color of the wristband or watchband changes color as an indication to the wearer that the wearer should increase his or her activity level (e.g., the wearer should use stairs instead of taking an elevator).

FIGS. 34-36 are diagrams that illustrate music features of a sports electronic training system according to an embodiment of the present invention. In an embodiment, a user can log into a music program running on a computer/web server as illustrated in FIG. 11A. When the user logs in, the user is presented with a display view such as, for example, display view 3402 in FIG. 34.

Display view 3402 enables a user to select music to be played on a portable electronic processing device according to the present invention during a workout. The music can be selected based on and/or matched to particular stride rates and ranges of stride rates. As described herein, stride rate is a measure of the number of steps an individual completes, for example, in one minute. Maintaining a constant stride rate when running, for example, is important to efficient running. Individuals vary their running speed by the energy they put into their stride. The rhythm of a runner's run can be enhanced and guided by selecting and playing music matched to a particular stride rate.

As shown in FIG. 34, display view 3402 includes a viewing area 3406 and 3408. Viewing area 3406 is used by a user to locate and retrieve music based on stride rate. Viewing area 3408 is used by a user to select stride rates and stride rate ranges, and to match music to the selected stride rates and stride rate ranges.

In an embodiment, as shown in FIG. 34, viewing area 3408 includes a stride rates bar 3410 and six stride rate matching tabs 3412a-f. Also located in viewing area 3410 is a match button 3414. In order to locate and match music to particular stride rates, a user moves the stride rate matching tabs 3412 to establish five stride rate ranges. In FIG. 34, the stride rate matching tabs have been positioned to form stride rate ranges of 60-95 steps per minute, 95-115 steps per minute, 115-150 steps per minute, 150-170 steps per minute, and 170-210 steps per minute. After the stride rate matching tabs are set, the user activates a music matching function, for example, by clicking on match button 3414 with a computer mouse. The music matching function searches through a music library or music database and places, for example, music files or pointers to music files (e.g., MP3 music files) in folders located in viewing area 3406 of display view

3402. To retrieve the music, the user goes to the files in viewing area 3402 and downloads the files to a portable electronic processing device according to the present invention.

In an embodiment, the music matching function analyzes music files stored in a music library and determines a beats per minute value for each music file. The beats per minute value for a music file is stored with a music file, for example, in a header field. The music matching function compares the beats per minute value for music files with stride rate values and, if there is a match, the music file, or a pointer thereto, is placed in an appropriate stride music file. In an embodiment, the music function searches music files stored, for example, on the user's home computer to identify music files having a particular beats per minute value. In another embodiment, the music function searches commercial music libraries, for example, located on web servers operated by music vendors, and the user is able to purchase music files at the completion of the matching process.

In embodiments of the present invention, the music matching function matches music to stride rates such that the beats per minute value of the music file is a ratio of the stride rate value. For example, the music beat may match every second footstep or every third footstep of a runner, as illustrated in FIG. 36, rather than simply match the beat to every footstep.

Referring to FIG. 34, after the music matching has been performed, the user is able to retrieve and download the matched music from the stride music files located in view area 3406 of display view 3402. In an embodiment, some or all of the music files may already be downloaded, in which case only the play list (e.g., play list commands) and any needed music files are downloaded.

If the user wishes to change one or more of the stride rate matching tabs, for example, to locate a broader variety of music for a particular stride rate range, the user can readjust the one or more stride rate matching tabs as desired and activate the music matching function again by clicking on match button 3414. In an embodiment, the music matching function determines the minimal amount of searching and matching necessary to accommodate the adjustments made by the user, and it only performs this minimal amount of searching and matching in order to save processing time. In an embodiment, the stride rate matching tabs can be set in a way to have a stride rate range which is limited to one particular stride rate.

FIG. 35 is a diagram that further illustrates display view 3402 according to an embodiment of the present invention. As illustrated in FIG. 35, when a user starts to move one of the stride rate matching tabs (e.g., tab 3412*d*), a list of music matched to the stride rate displayed on the tab (e.g., 150) is displayed in viewing area 3408. The music list 3420 shown in FIG. 35 includes four songs matched to a stride rate of 150 steps per minute. The song by artist Taylor is matched to every second step, while the song by artist White is matched to every third step. The other two songs are matched to every footstep. An arrow 3422 at the bottom of music list 3420 is used to scroll through additional songs matched to a stride rate of 150 steps per minute. In an embodiment, clicking on match button 3414 re-activates the music matching function, and the music matching function performs any additional searching and/or matching necessary to accommodate adjustments made by the user to the stride rate matching tabs 3412.

FIGS. 37-40 are diagrams that further illustrate virtual training features of a sports electronic training system according to an embodiment of the present invention. As described herein, a portable electronic processing device such as, for example, device 1300 can share data and information with programs running, for example, on a computer/web server. This ability to share data and information enhances the functionality of the present invention.

FIG. 37 is a diagram that illustrates a performance schedule display view 3700 for a training program running on a computer/web server. In an embodiment, the training program assists individuals in developing exercise programs appropriate for their individual fitness levels and their specific fitness or exercise goals. The training program enables individuals to store, retrieve and exchange data and information relevant to their individual fitness.

As shown in FIG. 37, display view 3700 includes a header display area 3702, a main display area 3704, and a footer display area 3706. Header display area 3702 includes links to other display views such as, for example, a performance snapshot display view 4000 (see FIG. 40) and a performance stats display view 3800 (see FIG. 38). A user can bring up a desired display view, for example, by clicking on one of the links provided using a computer input pointing device (e.g., a computer mouse). In an embodiment, header display area 3702 also displays a user's stored fitness level and fitness number/fitness score as well as performance values for the user's last stored workout.

Main display area 3704 includes a calendar that depicts a user's workout schedule. The calendar view is user selectable so that the user can view workouts, for example, for a selected month, for a selected week, or for a selected day. As shown in FIG. 37, each workout can be identified by a workout name and/or a bar that depicts the intensity of the workout.

In an embodiment, the calendar view includes both planned workouts and completed workouts. If a user wishes to view a particular workout, the user can bring up a detailed display view for the workout, for example, by clicking on the workout using a computer input pointing device. Navigation controls 3708 enable a user to change, for example, the calendar year and month displayed.

Footer display 3706 includes links to additional display views such as, for example, a goals display view, a workouts display view, a challenges display view, a music display view, a products display view, a fitness display view and/or a community display view.

In an embodiment, the goals display view displays an individual's planned workouts, the number of planned workouts completed, and the number of planned workouts remaining to be completed. The display view also provides indication(s) about whether the individual is meeting the specified goals for the completed workouts. An example of the type of information that is provided is shown in display area 4006 of FIG. 40. The goals display view also includes features to permit the user to change goals and set new goals.

The workouts display view displays, in an embodiment, all of the various information relating to workouts created by a user. This information is described above, for example, with references to FIGS. 13-33. In an embodiment, the workouts display view presents details about workouts graphically as illustrated, for example, in display 3808 of FIG. 38.

The challenges display view displays, in an embodiment, information relating to challenges such as on-line virtual races, et cetera. The challenges enable a user to compete against himself or herself (e.g., ghost running), against family and friends and/or against anyone else, anywhere in the world, having access, for example, to the Internet. In an embodiment, the challenges allow for the calculation and use of handicap scores that allow individuals at different performance levels to compete against one another. In an embodiment, the display view enables the user to create, view, and join challenges, and to view the results of completed challenges.

The music display view displays, in an embodiment, information about music, the user's play lists, et cetera. In an embodiment, it enables the user to select and download music to a portable electronic processing device such as, for example, device 1300. Example music display views are described above with reference, for example, to FIGS. 34-36.

The products display view displays, in an embodiment, information about the various components and products that make up a sports electronic training system according to embodiments of the present invention. In an embodiment, it includes articles relating to various features of products (e.g., product reviews, brochures, data sheets, user manuals, et cetera) as well as information about how to obtain products (e.g., on-line ordering information). This information aids a user in selection of products that are best suited to the user's needs and desires. In an embodiment, the products display view also includes an ability to send and receive technical support messages relating to various products that make up a sports electronic training system according to embodiments of the present invention.

In one embodiment, a user can elect to share information stored on the computer/web server with various entities, which enables the elected entities to provide information about various products to the user. In an embodiment, the products display view is customizable so that it displays only information elected to be received by the user.

The fitness display view displays, in an embodiment, fitness information such as, for example, health and nutritional information. In an embodiment, the fitness display view includes information about various sports in which a user might engage such as, for example, running, soccer, basketball, et cetera. In an embodiment, the fitness display view is customizable so that it displays information elected to be received by the user.

The community display view displays, in an embodiment, information about, and links to, various on-line communities. For example, in an embodiment, the community display view provides information about and links to an on-line running community that hosts runner databases, running calculators, upcoming running events, running club links, et cetera. The community view display also can include information about and links to other on-line communities relating to other sports. In an embodiment, the community display view is customizable so that it displays information elected to be received by the user.

In an embodiment, the fitness level and/or fitness number displayed in header display area 3702 is used to determine information content provided to user, for example, when the user selects the products display view and/or the fitness display view.

FIG. 38 is a diagram that illustrates a performance stats display view 3800 for the training program. Display view 3800 is similar to display view 3700 with regards to the information displayed in header display area 3802 and in footer display area 3806.

In an embodiment, display view 3800 includes a workout display 3808 in main display area 3804. Workout display 3808 displays both the workout goals for a selected workout and workout stats for the selected workout, if the workout has been completed. The workout goals are depicted by workout time and intensity boxes 3809*a-e*. In an embodiment, the intensity of each workout box 3809 corresponds to a particular heart beats per minute target range, as shown in area 3810 of display area 3804. The workout stats are depicted by line 3811. In an embodiment, the workout shown in display area 3804 can be changed using the calendar and navigation buttons located in display area 3812.

As shown in FIG. 38, a movable caret 3807 is located in display area 3804. Moving display caret 3807 so that it corresponds to a particular moment during a completed workout brings up a display balloon 3902 (see FIG. 39) that displays performance parameters for the particular moment. In an embodiment, the displayed performance parameters include heart rate, pace, stride rate, calories, distance, and time.

FIG. 40 is a diagram that illustrates a performance snapshot display view 4000 for the training program. Display view 4000 is similar to display view 3700 with regards to the information displayed in header display area 4002 and in footer display area 4008.

In an embodiment, display view 4000 displays stats for the last workout completed on a calendar page located in display area 4004. Also shown on calendar page(s) in display area 4004 is information about upcoming planned workouts. In an embodiment, a window is also provided that enables a user to manage music play lists.

In one embodiment, display view 4000 includes a goal tracker display in a display area 4006. The goal tracker display displays an individual's planned workouts, the number of planned workouts completed, and the number of planned workouts remaining to be completed. The goal tracker display provides indication(s) about whether the individual is meeting the specified goals for the completed workouts. In one embodiment, an individual is periodically prompted to input and/or update personal information (e.g., weight) to determine whether the individual is meeting specific fitness goals (e.g., a weight loss goal).

In one embodiment, the trainer program downloads software to a portable electronic processing device when the device is synchronized to the trainer program. This software prompts a user (e.g., a runner) to answer specific questions during a workout such as, for example, how the user is feeling (e.g., tired, legs hurt, etc.). The answers to the questions are uploaded when the device is resynchronized to the trainer program, and the answers are correlated to measured performance/body parameters and used to provide individual training feedback to the user (e.g., feedback relating to speed, distance, gait, etc.). In an embodiment, the answers are transferred to a professional trainer (i.e., a person) who reviews and analyses the answers and provides professional feedback to the user (e.g., by e-mail, text message, telephone call, etc.)

In an embodiment, the trainer program periodically sends positive feedback (e.g., outside of a workout period) to motivate an individual and to encourage the individual to progress to a next fitness level. The feedback can be provided to the individual by sending the individual a mobile phone text message, an e-mail at work, et cetera.

In embodiments of the present invention, the display views associated with various features of the present invention such as, for example, the trainer program and the portable electronic processing devices described herein can be configured by a user to display desired information in a format chosen by the user. Accordingly, the present invention is not limited to the example display views presented above.

In embodiments, the sports electronic training system, and applications thereof, described herein have features that are beneficial to many different industries. For example, the data collected, processed and stored by the present invention can be used by the fitness industry, the health/medical industry, the insurance industry, et cetera. Accordingly, the present invention should not be limited to any particular industry such as, for example, the sports industry.

FIG. 41 is a diagram that illustrates intelligent sport balls having accelerometers or motion monitors. In embodiments, the sports balls communicate with a portable electronic processing device 4101 according to an embodiment of the present invention. The sport balls include, for example, a soccer ball 4102, a baseball 4104, a tennis ball 4106, a golf ball 4108, a basketball 4110, and a football 4112.

In an embodiment, an accelerometer, a sensor, or a motion monitor is included in each of the sport balls to measure, for example, how far and how fast the sport ball travels when it is kicked, hit and/or thrown. As used herein, the term sensor means a device that can include a storage (e.g., memory) and a processor. This information is communicated wirelessly to portable electronic processing device 4101 and displayed on a display. In embodiments, other miniature sensors such as, for example, a pressure sensor, an altimeter, a magnetic field sensor, et cetera, are included in the sport balls to collect additional information that is transmitted to portable electronic processing device 4101 for display. This information is used to determine, for example, how much force was applied to kick, hit and/or throw the sport ball, how high the sport ball went when it was kicked, hit and/or thrown, whether the sport ball crossed a goal line, et cetera. Other parameters about a ball that can be determined and displayed include the ball's spin, air time, arc, et cetera. In embodiments, the accelerometer, motion monitor and/or other sensors are mounted or located, for example, within the ball, in the center of the ball (e.g., using a mounting or suspension system), or in an outer surface of the ball. In an embodiment, the accelerometer is formed using multiple accelerometers arranged, for example, so that they create a plane.

In an embodiment, a sport ball such as, for example, a soccer ball according to the present invention contains circuitry for communicating with nearby devices and for storing data received from nearby devices. For example, in the case of a soccer ball, each player wears shoes having identification devices (e.g., identification chips, radio-frequency identification (RFID) tags, etc.) that transmit a unique identification value to the ball each time one of the player's shoes comes into contact with the ball. Similarly, each goaltender or goalkeeper wears gloves having identification devices that transmit a unique identification value to the ball each time one of the goal tender's gloves comes into contact with the ball. In this way, the ball receives and stores data during a training session or a game that can be downloaded and reviewed/analyzed after the training session or the game. The data stored by the ball is a record, for example, of when and how often each player came into contact with the ball.

In addition to storing data, for example, about when and how often each player came into contact with the ball during a training session or a game, the ball can also store information in the case of the soccer ball, for example, regarding how hard a player kicked the ball, how far the ball was kicked by a player, how much spin a player imparted to the ball when the ball was kicked, the arc of the ball, how many times the ball was passed, how many time the ball was thrown, et cetera. In this way, the data stored by the ball is a more complete record of the training session or game, and the additional data can be downloaded and review/analyzed, for example, after the training session or game.

In embodiments, a sport ball of the present invention is used independently of other devices described herein. For example, there is no requirement for any data to be transmitted to the sport ball by another device such as a motion monitor attached to a soccer boot. There is also no requirement for the sport ball to interact with a portable electronic processing device such as, for example, a mobile phone, an MP3 music file player, or a PDA. In embodiments, the ball includes memory that stores data (e.g., data about how hard the ball was kicked, how far the ball traveled, how fast the ball traveled, how much spin was imparted to the ball, how many times the ball was passed, how many time the ball was thrown, etc.) collected by the ball's sensor(s)/monitor(s). This data can be downloaded to a computer, for example, when the ball is not being used. In an embodiment, the data is downloaded and stored on a web server that is compatible with the various other sports electronic training system features described herein.

In an embodiment, when a sport ball changes motion, for example, due to a kick, a sensor or motion monitor in the sport ball generates a response signal. In an embodiment, the algorithm(s) used by the sport ball to generate values described herein (e.g., how hard the ball was kicked, how far the ball will travel, the arc of the ball, et cetera) are chosen so that the values can be generated shortly after a player contacts the ball. For example, an algorithm used to determine how far a soccer ball will travel after being kicked is preferably based on an impact force and an initial trajectory of the ball (e.g., determined using a tri-axial accelerometer or a plurality of accelerometers) rather than a flight time of the ball. In this way, how far the ball will travel is known before the ball travels, for example, more than some nominal distance.

In an embodiment, in addition to using a soccer ball, for example, to record data about a training session or game, each player can wear sensors/motion monitors that record data about the player. For example, a motion monitor in a player's shoe(s) can monitor movement of the player about the playing field and receive data from the soccer ball each time the player comes into contact with the ball. In an embodiment, the motion monitor keeps track, for example, of the player's forward, sideways, and backward running distance and speed. In addition, the motion monitor receives data from the ball during the training session or game regarding how many times the player came into contact with the ball, how hard the player kicked the ball, how far the ball was kicked by the player, how much spin the player imparted to the ball when the ball was kicked, the arc of the ball, et cetera. This data can be generated by the ball and transmitted to a motion monitor in the player's shoe, for example, before the ball is beyond the transmission range of the ball's transceiver circuitry. In an embodiment, the recorded/stored data about a player is downloaded and review/analyzed after the training session or game.

In an embodiment, sensors/motion monitors worn by or associated with a soccer player, for example, may be used to determine one or more of the values described herein with regard to the soccer ball and vice versa. Thus, the present invention is not limited to having a particular value described herein be generated only by a sport ball or only by sensors/motion monitor worn by or associated with, for example, a soccer player.

In embodiments, a sport ball according to the present invention transmits data such as, for example, how hard the ball was kicked, how far the ball will/has traveled, the arc of the ball, et cetera to a watch or other portable electronic processing device according to the present invention. This information can then be viewed in real time or near real time, for example, on the watch display. The information can also be downloaded from the watch or other portable electronic processing device and stored on a web server that is compatible with the various other sports electronic training system features described herein.

In an embodiment, when the only acceleration vector acting on a sport ball is the gravity vector, the ball is considered to be at rest, and the time period for collecting and processing data for the ball (e.g., relating to a particular kick, hit and/or throw) can be reset.

In embodiments, the information from the sensor(s) in the sport balls can be received by any portable electronic processing device compatible with an embodiment of a sports training system described herein.

FIG. 42 is a diagram that illustrates a multi-sensor monitor 4200 according to an embodiment of the present invention. Multi-sensor monitor 4200 includes a processor 4202, memory 4204, a heart rate sensor 4206, a transceiver 4208, an antenna 4210, a battery 4212, and a plurality of sensors 4214.

Processor 4202 is a conventional processor such as, for example, a microcontroller capable of implementing application programs stored in memory 4204. Processor 4202 is coupled to memory 4204, heart rate sensor 4206, transceiver 4208, and the plurality of sensors 4212.

Memory 4204 is used to store application program instructions and data. In an embodiment, memory 4204 stores programs, for example, used to generate performance data from data output by heart rate sensor 4206 and the plurality of sensors 4214. In an embodiment, memory 4204 includes both read only memory and random access memory.

In an embodiment, heart rate sensor 4206 is an electronic sensor that detects heart beats. This data is provided to processor 4202 and used to determine a heart beat rate (e.g., number of beats per minute).

Transceiver 4208 is a low-power transceiver used to communicate with other components of a sports electronic training system according to embodiments of the present invention. In an embodiment, transceiver 4208 operates in an unlicensed frequency band such as 2.4 GHz. Transceiver 4208 is coupled to an antenna 4210.

Battery 4212 is used to provide power to operate the various components of multi-sensor monitor 4200. In an embodiment, battery 4212 is a non-rechargeable battery that must be periodically replaced. Battery 4212 can also be a rechargeable battery.

Sensors 4214 are sensors that measure parameters associated with the performance of an individual. Such sensors include, for example, temperature sensors, hydration/moisture sensors, salination sensors, ionization/deionization sensors, oxygen sensors, motion sensors/accelerometers, altimeters, et cetera.

In an embodiment, multi-sensor monitor 4200 is built into sports clothing and used to measure parameters for an individual engaged in a sporting event. The sporting event can include, for example, a track and field event such as a race, or a team sport such as a soccer game, a basketball game, et cetera. Information collected by multi-sensor monitor 4200 is transmitted wirelessly, for example, to a monitoring device that displays the information to a coach or other individual tasked with monitoring the performance of one or more individuals. When the information collected from an individual indicates that an individual participating in a team sport is not performing at an expected performance level and needs a rest period, the individual can be taken out of the game for a rest. In an embodiment, information from sensors such as, for example, hydration/moisture, ionization/deionization and/or saltation sensors are used to determine and recommend special drinks or special food to the individual (e.g., to be consumed during a long term workout such as a marathon or soccer game, or after the workout).

In an embodiment, multi-sensor monitor 4200 is used with intelligent clothing to control the clothing. For example, in one embodiment, multi-sensor monitor 4200 operates controls that activate heating and/or ventilating feature of clothes. These features can include turning on and off heaters, and inflating or deflating air bladders within the clothing to allow, for example, more or less ventilation. In an embodiment, sensors of multi-sensor monitor 4200 detect and use the presence of moisture, or a lack of moisture, as an indicator to determine whether more or less ventilation is demanded. In an embodiment, temperature sensors on the inside and the outside of a garment are used to determine a temperature difference, which together with other information such as, for example, weather information are used to influence and/or control the ventilation/heating properties of the garment.

In an embodiment, a portable electronic processing device according to the present invention is used to control the compression of a garment (e.g., which is important in swimming to increase blood flow) and/or to control the support/stability function of a garment (e.g., using integrated support elements such as thermoplastic urethane bands). In an embodiment, a portable electronic processing device according to the present invention is used to control various parameters of an article of footwear. This includes, for example, cushioning, stability, the closure system, active or passive ventilation, traction properties, pronation/supination control, intelligent ribs on soccer boots, et cetera.

In an embodiment, garments worn by an athlete, for example, contain integrated sensors to detect movement of the athlete's upper body and posture of the body. The output of these sensors are used to provide feedback to the athlete, for example, regarding how to change body movement and/or posture in a sport like golf, gymnastics or figure skating, where upper body movement and posture are important. For example, the feedback provided to a golfer would let the golfer know how upper body movement is changing or not changing during swings.

In an embodiment, sensors are placed and/or built into a shoe to measure, for example, a runner's running form and gait cycle (e.g., sensors are placed and/or built into the heel, midsole, and toe of the shoe). Additional sensors/motion monitors can also be placed on the runner's knee and hip, for example, to obtain more information about the runner's running form. The information collected by the sensors/motion monitors is analyzed by the virtual trainer of the present invention and used to provide feedback to the runner regarding how the runner can improve his or her running form and/or gait cycle. In an embodiment, sensors/motion monitors worn by a runner are used to determine running biomechanics. This is accomplished, for example, by analyzing the outputs of the sensors/motion monitors worn on various parts of a runners body to determine the runner's rotational and translational movements/accelerations.

In one embodiment, retailers are provided with advanced sensor products and/or equipment described herein, which they rent and/or provide to individuals to evaluate the individuals. The evaluation results are then used, for example, by the retailers to sell products (e.g., shoes) to the individuals that are tailored to their personal needs (e.g., shoe properties that match a runner's running form).

FIG. 43 is a diagram that illustrates using components of the present invention to monitor a sports player 4302 and a sport ball 4304. Sports player 4302 is wearing sports clothing that includes a built in multi-sensor monitor 4200. Monitor 4200 collects information about sports player 4302 and transmits this information to a device that displays the information on a display 4306. Sport ball 4304 also includes one or more monitors, as described above. Information collected by these monitors is transmitted to one or more devices and displayed on a display, such as for example display 4306.

In an embodiment, the information displayed for sports player 4302 includes heart rate information, hydration information, temperature information, motion information, et cetera. In one embodiment, information collected by the sensors of multi-sensor monitor 4200 is combined to produce a fatigue/performance index value. The index value can be monitored to indicate at what level sports player 4302 is performing or capable of performing. The fatigue/performance index value can be monitored over time and compared to the sports player's actual performance in games to determine how well sport player 4302 is capable of performing for a given range of fatigue/performance index values.

In one embodiment, the present invention is used to monitor the performance of a boxer. Monitors in the gloves of the boxer, for example, measure the boxer's punching speed and power. Motion monitors can also be used to track and record data about the boxer's hand movements and form, and training feedback can be provided to the boxer based on an analyzes of the recorded data.

In one embodiment, the present invention is used to monitor the performance of a swimmer. Motion monitors, for example, on an arm and/or leg of the swimmer monitor the number of strokes performed by the swimmer, and the swimmer's speed, laps, swimming form; pace, et cetera. Goggles with color indications provide feedback to the swimmer about performance. For example, in one embodiment, three lights indicate zones of performance (e.g., on target performance, below target performance, and above target performance). In another embodiment, two colors indicate performance (below target performance and above target performance—no indicator light is used to indicate on target performance).

In one embodiment, one or more sensors such as, for example, a miniature pressure altitude sensor are used to monitor and to measure jumps, leaps, et cetera, of an individual. This information can be combined with other information described herein and analyzed to provide training feedback to the individual.

In an embodiment, information transmitted for sports players participating in a game can be encrypted so that only authorized individuals can receive and display the information.

As illustrated by FIGS. 44 and 45, in embodiments of the present invention, components of the sports electronic training system described herein are used to interact with electronic games. In an embodiment, illustrated by FIG. 44, an individual uses the sports electronic training system components described herein, for example, to gain credits and/or reward points for exercising that can be downloaded to an electronic game (e.g., to build up the health, fitness, and strength of an avatar or digitally created character or digitally created character). In another embodiment, illustrated by FIG. 45, an individual uses the sports electronic training system components described herein, for example, to interact directly with an electronic game.

FIG. 44 illustrates an individual 4400 using a display 4402 and a gaming device 4404 to play an electronic game. The game includes an avatar or digitally created character 4406. As used herein, the term digitally created character is broader than the term avatar. As used herein, the term digitally created character means any computer game character or electronic personality, for example, to include what is commonly referred to in the computer gaming art as an avatar. In order for the avatar or digitally created character to build up, for example, health, fitness, and strength, and thereby make the game more interesting and/or appealing to individual 4400, individual 4400 must collect health, fitness, and strength points by exercising. The individual collects these points by using various components of the sports electronic training system described herein to monitor and record his exercise. After an exercise workout, individual 4400 can download points, for example, from a portable electronic processing device according to the present invention to the electronic game.

In an embodiment, information that can be used to effect the avatar or digitally created character is gathered, for example, by playing in a real soccer game or performing other real physical activities and storing the information in a memory. The information is then brought back and downloaded to a gaming device or electronic game, for example, either wirelessly or using a docking station. The downloaded information is then used to effect, for example, the strength, power, health, et cetera of the avatar or digitally created character. In one embodiment, the information is gathered, stored, and brought back using a sport ball according to the present invention. In an embodiment, the information can be downloaded and stored on a web server that is compatible with the various other sports electronic training system features described herein, and retrieved from the web server for use with an electronic game.

In an embodiment, the more individual 4400 exercises using components such as, for example, motion monitor(s) and/or a heart rate monitor according to the present invention to monitor and record the exercise, the more health, fitness, and strength points individual 4400 earns for use with the electronic game. Because the health, fitness and/or strength points earned are proportional to the amount of exercise performed by individual 4400, individual 4400 is motivated to exercise and to be physically active.

In an embodiment, the virtual trainer of the present invention provides feedback to individual 4400 while individual 4400 is exercising. The feedback encourages and/or helps the individual increase and/or maximize the number of health, fitness and/or strength points that are earned.

FIG. 45 illustrates an embodiment of the present invention in which an individual 4500 uses various components of the sports electronic training system described herein to directly interact in real time with an electronic game. As illustrated by FIG. 45, individual 4500 is running in place in order to control movement of an avatar or digitally created character 4506. In embodiments, the activity level of individual 4500 effects the individual's game score.

In an embodiment, the electronic game is played using a television 4502 and a gaming console 4504. Movement of the avatar or digitally created character 4506 is influenced based on the movement of individual 4500, which is monitored in an embodiment using the sensors/motion monitors and/or one or more portable electronic processing devices of the present invention described herein. The components of the sports electronic training system used by individual 4500 communicate, either directly or through a portable electronic processing device, with gaming console 4504. In an embodiment, the portable electronic processing device communicates with gaming console 4504 either wirelessly or by using a docking port.

In an embodiment, wearable sensors (e.g., other than ones that monitor movement of the feet of individual 4500) are used to capture movement of individual 4500. In an embodiment, these wearable sensors are integrated, for example, into garments and/or joint sleeves worn by individual 4500 while playing the electronic game. In embodiments, performance data or a combination of physiologic and performance data are used within a game.

In embodiments of the present invention, an electronic game or at least a session thereof is played/displayed on one of the many sports electronic training system displays described herein (e.g., on a display of a portable electronic processing device, on the inside lenses of glasses, on a display integrated into a garment sleeve, et cetera). Earphones and/or a speaker of a portable electronic processing device are used to provide audio for the electronic game. As such, the game is not required to be played, for example, exclusively in a computer room or in a living room of a house or an apartment.

The present invention has been described above by way of exemplary embodiments.

Accordingly, the present invention should not be limited by any of the above-described exemplary embodiments, but should be defined only in accordance with the following claims and their equivalences.

What is claimed is:

1. An article of footwear, comprising:
    a sole, the sole comprising a bottom surface for contacting the ground and a top surface, the sole including a heel region, a forefoot region and a midfoot region, wherein the sole defines a recess in the midfoot region of the sole;
    a motion monitor housing comprising a hard plastic and having a first housing surface, wherein the first housing surface is disposed substantially parallel to the top surface of the sole; and
    a motion monitor disposed in the motion monitor housing, the motion monitor comprising an accelerometer, a memory, a personal area network transceiver, and a battery,
    wherein the accelerometer is configured to measure acceleration in more than one axis,
    wherein the accelerometer is further configured to provide a stream of acceleration data that corresponds to the motion of a foot of a user when the user engages in a locomotion activity while wearing the article of footwear, wherein the motion monitor is configured to filter the stream of acceleration data, and wherein the memory is configured to store a program used to generate performance data from the filtered acceleration data, and
    wherein the motion monitor is configured to store data collected during the locomotion activity in the memory, and to transmit the stored data to a mobile phone via the personal area network transceiver only after the locomotion activity is completed in response to first receiving a message from the mobile phone via the personal area network transceiver that the mobile phone is ready to receive the performance data, and wherein the motion monitor is further configured to operate in a first state at a relatively lower power consumption level and a second state at a relatively higher power consumption level.

2. The article of footwear of claim 1, wherein the first housing surface is disposed in a plane formed by a surface of the sole.

3. The article of footwear of claim 2, wherein the plane is formed by the top surface of the sole.

4. The article of footwear of claim 1, wherein the motion monitor housing comprises a mark configured to ensure proper orientation of the motion monitor within the recess.

5. The article of footwear of claim 1, wherein the motion monitor is configured to function properly regardless of its orientation within the recess.

6. The article of footwear of claim 1, wherein an axis of motion of the accelerometer is parallel to the first housing surface.

7. The article of footwear of claim 1, wherein the performance data includes information about the performance of the user who engages in the locomotion activity while wearing the article of footwear, wherein the information comprises duration and step number data.

8. The article of footwear of claim 7, wherein the duration data comprises the total duration of the user's monitored activity.

9. The article of footwear of claim 7, wherein the step number data comprises the total number of steps taken by the user during the user's activity.

10. The article of footwear of claim 1, wherein the performance data includes information about the performance of the user who engages in the locomotion activity while wearing the article of footwear, wherein the information comprises one of speed and pace data.

11. The article of footwear of claim 1, wherein the performance data includes information about the performance of the user who engages in the locomotion activity while wearing the article of footwear, wherein the information comprises the distance the user covered during the activity.

12. The article of footwear of claim 1, wherein the second state corresponds to the motion monitor operating in an active mode in which performance data may be transmitted, and wherein the first state corresponds to the motion monitor operating in a low power mode in which identification information is transmitted but performance data is not transmitted.

13. The article of footwear of claim 1, wherein the second state corresponds to the motion monitor transmitting performance data to the mobile phone via the personal area network transceiver.

14. The article of footwear of claim 1, wherein the second state corresponds to the motion monitor recording acceleration data in the memory that corresponds to the motion of the user's foot when the user engages in the locomotion activity while wearing the article of footwear.

15. The article of footwear of claim 1, wherein the motion monitor is configured to determine whether the user who engages in the locomotion activity while wearing the article of footwear is walking or running.

16. The article of footwear of claim 15, wherein the determination of whether the user is walking or running is based on whether a maximum acceleration value detected is below a predetermined threshold.

17. The article of footwear of claim 1, wherein the sole comprises a midsole.

18. The article of footwear of claim 1, wherein the motion monitor is configured to filter the stream of acceleration data to identify a maximum acceleration value for each stride of the user.

19. The article of footwear of claim 1, wherein the program further generates time data, and wherein the time data comprises the time that the user who engages in the locomotion activity conducted the locomotion activity.

20. The article of footwear of claim 1, wherein the motion monitor is configured to low-pass filter the stream of acceleration data.

* * * * *